US006964957B2

(12) United States Patent
Abreo et al.

(10) Patent No.: US 6,964,957 B2
(45) Date of Patent: Nov. 15, 2005

(54) FUSED PYRAZOLE COMPOUNDS, PHARMACEUTICAL COMPOSITIONS, AND METHODS FOR MODULATING OR INHIBITING ERAB OR HADH2 ACTIVITY

(75) Inventors: Melwyn A. Abreo, Jamul, CA (US); Jerry J. Meng, San Diego, CA (US); Charles S. Agree, San Diego, CA (US)

(73) Assignee: Agouron Pharmaceuticals, Inc., La Jolla, CA (US)

( * ) Notice: Subject to any disclaimer, the term of this patent is extended or adjusted under 35 U.S.C. 154(b) by 138 days.

(21) Appl. No.: 09/931,166

(22) Filed: Aug. 17, 2001

(65) Prior Publication Data

US 2002/0065292 A1 May 30, 2002

Related U.S. Application Data

(60) Provisional application No. 60/226,123, filed on Aug. 18, 2000.

(51) Int. Cl.[7] .................... C07D 487/04; C07D 471/04; A61K 31/519; A61K 31/437
(52) U.S. Cl. ............................ 514/217.06; 514/217.07; 514/252.16; 514/253.04; 514/262.1; 514/303; 540/599; 540/600; 544/262; 544/362; 546/119
(58) Field of Search ................. 514/217.05, 217.07, 514/252.16, 253.04, 262.1, 303; 540/599, 600; 544/262, 362; 546/119

(56) References Cited

U.S. PATENT DOCUMENTS

| | | | |
|---|---|---|---|
| 3,165,520 A | 1/1965 | Schmidt et al. | |
| 4,666,908 A | 5/1987 | Hamilton | |
| 5,047,404 A | 9/1991 | Coates et al. | |
| 5,272,147 A | 12/1993 | Bell et al. | |
| 5,294,611 A | 3/1994 | Venkatesan et al. | |
| 5,294,612 A | 3/1994 | Bacon et al. | 514/234.2 |
| 5,426,107 A | 6/1995 | Bell et al. | |
| 5,541,187 A | 7/1996 | Bacon et al. | |
| 5,656,627 A | 8/1997 | Bemis et al. | |
| 5,656,629 A | 8/1997 | Bacon et al. | |
| 5,707,998 A | 1/1998 | Takase et al. | |
| 6,194,410 B1 | 2/2001 | Bos et al. | |
| 6,197,774 B1 | 3/2001 | Yamada et al. | |
| 6,207,829 B1 | 3/2001 | Dunn et al. | |
| 6,262,302 B1 | 7/2001 | Wu et al. | |

FOREIGN PATENT DOCUMENTS

| | | |
|---|---|---|
| EP | 0 463 756 | 2/1992 |
| EP | 0 526 004 | 3/1993 |
| WO | WO 94/28902 | 12/1994 |
| WO | WO 95/34563 | 12/1995 |
| WO | WO 96/16644 | 6/1996 |
| WO | WO 98/40484 | 9/1998 |
| WO | WO 98/49166 | 11/1998 |
| WO | WO 99/18987 | 4/1999 |
| WO | WO 99/30710 | 6/1999 |
| WO | WO 00/24742 | 5/2000 |
| WO | WO 00/76969 | 12/2000 |
| WO | WO 00/76987 | 12/2000 |
| WO | WO 00/76988 | 12/2000 |
| WO | WO 01/12598 | 2/2001 |

OTHER PUBLICATIONS

G. Y. Wen, S. Y. Yang, W. Kaczmarski, X. Y. He and K. S. pappas, Brain Research, vol. 954, Issue 1, Nov. 1, 2002, pp. 115–122.*
Rob Ofman, Jos P. N. Ruiter, Marike Feenstra, Marinus Duran,1Bwee Tien Poll–The, Johannes Zschocke, Regina Ensenauer, Willy Lehnert, Jörn Oliver Sass, Wolfgang Sperl, and Ronald J. A. Wanders, Am. J. Hum. Genet., 72:1300–1307, 2003.*
Wolff, Manfred E. "Burger's Medicinal Chemistry, 5ed, Part I", John Wiley & Sons, 1995, pp. 975–977*
Banker, G.S. et al, "Modern Pharmaceutics, 3ed.", Marcel Dekker, New York, 1996, pp. 451 and 596.*
International Search Report, PCT/US 01/41795, filed Aug. 17, 2001 (mailed Jan. 11, 2002).
Auzzi et al., Boll. Chim. Farm., 112, 521–8 (1973).
Bagshawe, Drug Dev. Res., 34, 220–230 (1995).
Bergmann, R. et al., J. Med. Chem., 33, 492–504 (1990).
Bergmann et al., J. Chem. Soc., 1 (11), 2795–802 (1979).
Bertolini et al., J. Med. Chem., 40, 2011–2016 (1997).
Binstock et al., Methods Enzymol. 71, 403–411 (1981).
Bodor, Advances in Drug Res., 13, 255–331 (1984.
Buck, J. et al, J. Chem. Soc., Perkin Trans. 1(1), 67–73 (1992).
Bundgaard, Design of Prodrugs (Elsevier Press 1985).
Dear et al., J. Chromatogr. B, 748, 281–293 (2000).
Fukuyama et al., Tetrahedron Letters, 26, No. 51, 6292 (1985).
Ganem et al, Chemtracts: Org. Chem., 1(5), 413–14 (1988).
Glenner, et al., Biochem. Biophys. Res. Commun., 120:885–890 (1984).
Hagiwara et al., J. Chem. Soc., Chem. Commun., 1351–1353 (1987).
He et al., J. Bio. Chem. vol. 273. No. 17, pp. 10741–10746 (1998).

(Continued)

Primary Examiner—Thomas C. McKenzie
(74) Attorney, Agent, or Firm—Peter C. Richardson; Bryan C. Zielinski; Galina M. Yakovleva

(57) ABSTRACT

Pyrazole compounds represented by the formula:

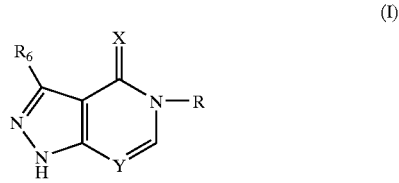

(I)

are described. The pyrazole compounds and pharmaceutical compositions containing them may be used in inhibiting ERAB or HADH2 activity and in treating ERAB, HADH2 or amyloid-β mediated diseases and conditions.

49 Claims, No Drawings

OTHER PUBLICATIONS

He et al., *J. Biol. Chem.*, 274(21), pp. 15014–15019(1999).
Hwu et al., *J. Org. Chem.*, 52, 188–191 (1987).
Kang et al., *Nature*, vol. 325, pp. 733–736 (1987).
Koziara, A. et al., *Synthesis*, 527–529 (1979).
Kuzuya et al., *Nippon Kagaku Kaishi*, 12, 1746–53 (1986).
Ladduwahetty, *Contemp. Org. Synth.*, 4(4), 309–325 (1997).
Larsen, *Design and Application of Prodrugs, Drug Design and Development* (Krogsgaard–Larsen et al., eds., Harwood Academic Publishers, (1991).
Masui et al, M., Chemtracts:*Org. Chem.*, I(5), 385–7 (1988).
Petitou et al., *Tetrahedron Letters*, 29, No. 12, 1389–1390 (1988).
Prox et al., *Xenobiol*, vol. 3, No. 2, 103–112 (1973).
Oppermann et al., *FEBS Lett*, 451(3), pp. 238–242 (1999).
Schultz et al., *Stereosel. React. Met.–Act. Mol., Proc. Symp.*, $2^{nd}$ (1995), Meeting Date 1994, 45–48. Publisher: Vieweg, Wiesbaden, Germany: Roush, *Chemstracts*.
Secrist et al., *J. Med. Chem.*,(1993)36(13), 1847–1854.
Selkoe, *Annual Review of Neuroscience*, vol. 17, pp. 489–517 (1994).
Shan et al., *J. Pharm. Sci.*, 86 (7), 765–767 (1997).
Sieburth et al, *J. Org. Chem.*, 64(3), 950–953 (1999).
Small et al., *Journal of Neurochemistry*, vol. 73, No. 2, pp. 443–449 (1999).
Sorato, C., *Chemtracts: Org. Chem.*, 2(4), 255–7 (1989).
Spraul et al.,*J. Pharmaceutical & Biomedical Analysis*, vol. 10, No. 8, 601–605 (1992).
Still et al., *J. Org. Chem.*, 43, No. 14, 2923–2925 (1978).
Storey et al., *Neuropathology And Applied Neurobiology*, vol. 25, pp. 81–97 (1999).
T. Greene and P. Wuts, Protecting Groups in Chemical Synthesis, Index (3rd ed.), John Wiley & Sons, NY (1999).
Walters et al., *Tetrahedron Lett.*, 36(42), 7575–8 (1995).
Wilson et al., *Journal of Neuropathology And Experimental Neurology*, vol. 58, No. 8,pp. 787–794 (1999).
Yamawaki, *Chem. Lett.*, 1143–1146 (1981).
Yan et al., *J. Biol. Chem.*, vol. 274, No. 4, pp. 2145–2156 (1999).
Yan et al., *Nature*, vol. 389, pp. 689–695 (1997).
Yao e tal., *Bioorg. Med. Chem. Lett.*, 8(6), 699–704(1988).

* cited by examiner

FUSED PYRAZOLE COMPOUNDS, PHARMACEUTICAL COMPOSITIONS, AND METHODS FOR MODULATING OR INHIBITING ERAB OR HADH2 ACTIVITY

CROSS REFERENCES TO RELATED APPLICATION

This application claims the benefit of U.S. Provisional Application Ser. No. 60/226,123, filed Aug. 18, 2000.

FIELD OF THE INVENTION

The present invention generally relates to pyrazole compounds, compositions comprising pyrazole compounds, and methods for modulating or inhibiting ERAB or HADH2 activity using those compounds and compositions. The present invention also generally relates to therapeutic compounds, compositions, and methods for treating ERAB, HADH2 or amyloid-β mediated conditions and diseases. Additionally, the present invention relates to therapeutic compounds, compositions, and methods for treating neurodegenerative diseases and certain cancers.

BACKGROUND OF THE INVENTION

Many conditions and diseases are believed to be associated with, induced, and/or mediated by the amyloid-β peptide ("Aβ" or "amyloid-β"), a proteolytic fragment of the integral membrane glycoprotein, amyloid-β precursor protein (APP) [Kang et al., *Nature*, vol. 325, pp. 733–736 (1987)]. Examples of such diseases, conditions and/or cancers include progressive neurodegenerative disease, such as Alzheimer's disease ("AD") or related Aβ-mediated dementia, and certain cancers, such as breast and endometrium cancers [see He et al., *J. Biol. Chem.*, 274(21), pp 15014–15019(1999)].

Aβ has been identified as a 39–43 amino acid peptide having a molecular weight of about 4.2 kD, which peptide is substantially homologous to the form of the protein described by Glenner, et al., *Biochem. Biophys. Res. Commun.*, 120:885–890 (1984), including mutations and post-translational modifications of the normal .beta.-amyloid peptide. Aβ peptide has been described in U.S. Pat. No. 6,262,302 as an approximately 39–43 amino acid fragment of a large membrane-spanning glycoprotein, referred to as the Aβ precursor protein (APP).

Aβ may interact with certain intracellular proteins and that interaction could lead to cytotoxic events. Examples of intracellular proteins believed to interact with Aβ are Endoplasmic Reticulum-associated Amyloid-β-peptide binding protein ("ERAB") and L-3-Hydroxyacyl-CoA Dehydrogenase Type II ("HADH2").

As used herein, "ERAB" refers to Endoplasmic Reticulum-associated Amyloid-β-peptide binding protein. ERAB has been identified as a dehydrogenase enzyme capable of binding Aβ [Yan et al., *Nature*, Vol. 389, pp. 689–95 (1997)]. As used herein, "HADH2" refers to L-3-Hydroxyacyl-Co Dehydrogenase Type II. HADH2, believed to be identical to ERAB, has been independently identified as a new L-3-hydroxyacyl-CoA dehydrogenase with an apparent role in the mitochondrial fatty acid β-oxidation pathway [He et al., *J. Bio. Chem.* Vol. 273. No. 17, pp. 10741–10746 (1998)]. The terms "ERAB", "HADH2" and "HADH" are interchangeably used in the art to indicate the amyloid-β binding protein. Throughout the application, the term "ERAB or HADH2" is used to indicate the ERAB and HADH2 protein, as well as the ERAB and HADH2 gene.

ERAB or HADH2 is an $NAD^+$ dependent dehydrogenase which catalyzes the reversible oxidation of L-3-hydroxyacyl-coA. The human short chain L-3-hydroxyacyl-CoA dehydrogenase gene is organized into six exons and five introns and maps to chromosome Xp11.2 [He et al., *J. Biol. Chem*, Vol. 273, pp. 10741–6 (1998)]. Sequence comparisons show that ERAB or HADH2 belongs to the short-chain dehydrogenase/reductase ("SDR") family of enzymes. ERAB or HADH2 has been cloned, expressed, purified, and characterized from human brain [He et al., *J. Biol. Chem.*, Vol. 273, pp. 10741–6 (1998)]. ERAB or HADH2 messenger RNA is expressed ubiquitously in normal human tissues. It is highest in liver and heart but ERAB or HADH2 is also expressed in normal brain.

Experimental evidence suggests that ERAB or HADH2 interacts with the Aβ peptide and can mediate its cytotoxicity. For example, ERAB or HADH2, normally found in the endoplasmic reticulum and mitochondria, has been shown to become redistributed to the plasma membrane fraction of cells in the presence of Aβ peptide [Yan et al., *Nature*, vol. 389, pp. 689–95 (1997)]. Likewise, it has been shown that the cytotoxic effects of Aβ on neuroblastoma cells in culture can be blocked by anti-ERAB or anti-HADH2 antibodies. Cells that overexpress ERAB or HADH2 and Aβ show elevated markers of cytotoxicity and cell stress compared to mock transfected controls; conversely, cells overexpressing catalytically inactive mutants of ERAB or HADH2 were no more insensitive than controls which overexpressed Aβ alone [Yan et al., *J. Biol. Chem.*, vol. 274, pp. 2145–56 (1999)]. Further, the interaction of Aβ and ERAB or HADH2 links oxidoreductase activity with both apoptosis and amyloid toxicity [Spermann et al., *FEBS Lett*, 451(3), pp. 238–242 (1999)]. Thus, ERAB or HADH2 appears to mediate the intraneuronal toxicity of Aβ by acting on inappropriate substrates, possibly generating toxic aldehydes [Yan et al., *J. Biol. Chem.*, vol. 274, pp. 2145–56 (1999)].

Alzheimer's disease ("AD") is a progressive neurodegenerative disease of the brain resulting in diminished cognitive abilities, dementia, and ultimately death. AD can be diagnosed by a trained clinician through, for example, the patient history, physical examination, tests that measure memory and language skills, genetic testing, and magnetic resonance imaging (MRI).

A strong link has been established between the development of AD and the accumulation of "Aβ" outside of nerve cells in the brain [Storey et al., *Neuropathology And Applied Neurobiology*, vol. 25, pp. 81–97 (1999); Selkoe, *Annual Review of Neuroscience*, vol. 17, pp. 489–517 (1994); Small et al., *Journal of Neurochemistry*, vol. 73, pp. 443–9 (1999)]. Aβ is also the principal component of the extracellular plaques that are diagnostic of AD and species of the peptide have been shown to be engaged by intracellular targets [Yan et al., *Nature*, vol. 389, pp. 689–95 (1997)]. Aggregated Aβ appears to be toxic to neuronal cells in culture. Aβ has been reported to cause apoptotic (neuronal) cell death in vitro through the generation of nitric oxide and other free radicals. Aβ has also been reported as accumulating to form plaques both inside and outside nerve cells [Wilson et al., *Journal of Neuropathology And Experimental Neurology*, vol. 58, pp. 787–94 (1999)]. These plaques are believed to be strongly associated with the dementia caused by AD. There are several different ways that these plaques can damage the brain. One way they can cause damage is by disrupting the calcium channels. They can also create free radicals, which then damage the brain. When the plaques form between the nerve cells in the brain, microglia, a type of immune cell, can cause an inflammation leading to even more neurological damage.

In a normal brain, ERAB or HADH2 antigen is present at low levels, being predominantly localized in neurons. However, in neurons affected in AD, ERAB or HADH2 is found to be overexpressed relative to non-AD age matched controls, especially near deposits of Aβ [Yan et al., *Nature*, vol. 389, pp. 689–95 (1997)]. It has also been suggested that ERAB or HADH2 contributes to Aβ-associated pathogenesis of AD by reducing neuroprotective estrogen levels in the brain, based on the finding that the enzyme can also utilize estrogen as a substrate [Yan et al., *J. Biol. Chem.*, vol. 274, pp. 2145–56 (1999); He et al., *J. Biol. Chem.*, vol. 274, pp. 15014–9 (1998)].

Accordingly, compounds and compositions that modulate or inhibit ERAB or HADH2 activity find therapeutic utility in the treatment of ERAB or HADH2 mediated conditions and diseases. In addition to any therapeutic application, such ERAB or HADH2 inhibitors or modulators are useful in delineating the role of the ERAB or HADH2 enzyme in both normal cellular function and in Aβ pathogenesis.

Various pyrazole or pyrimidine derivatives have been reported for their pharmacological activity. For example, European Patent Publication Nos. EP 0 463 756 A1 and EP 0 526 004 A1, and U.S. Pat. Nos. 5,272,147 and 5,426,107 diclose certain pyrazol-[4,3-d]pyrimidine-7-one compounds that are reported to be selective cGMP PDE inhibitors. International publication Nos. WO96/16644, WO94/28902 and WO98/49166 disclose use of certain pyrazolo[4,3-d]pyrimidine-7-one compounds in treatment of impotence. U.S. Pat. No. 6,207,829 discloses a method for producing certain pyrazolo[4,3-d]pyrimidine-7-one and its intermediates. U.S. Pat. No. 6,197,774 reports certain pyrimidine derivatives that inhibit the formation of nitrogen monoxide, and their use in treatment of allergic diseases. U.S. Pat. No. 6,194,410 describes certain pyrazolopyrimidines and pyrazolotriazines having a sulphanyl group, that are reported to show selective affinity to 5HT-6 receptors and as being suitable for use in the treatment of central nervous disorders such as psychoses or schizophrenia. U.S. Pat. No. 4,666,908 discloses certain 5-substituted pyrazolo[4,3-d]pyrimidine-7-one compounds. U.S. Pat. Nos. 5,047,404, 5,707,998, and 5,294,611 describe certain fused pyrimidine derivatives, and quinazoline and quinazolinone compounds, respectively. U.S. Pat. Nos. 5,294,612, 5,656,629 and 5,541,187 disclose certain pyrazolo[4,3-d]pyrimidin-4-one compounds having substituents at the 6-position for treating cardiovascular diseases. U.S. Pat. No. 3,165,520 discloses certain coronary dilating pyrazolo-[3,4-d]-pyrimidine compounds.

WO 00/76969 reports a method of treating AD using certain isoindoline derivatives. WO 00/76987 and 00/76988 report a method of treating AD using certain thiazolidine derivatives.

WO 98/40484 discloses an isolated nucleic acid encoding an ERAB or HADH2, and a method for treating a neurodegenerative condition by administering an ERAB or HADH2 inhibiting agent in an amount effective to inhibit ERAB or HADH2 polypeptide binding to Aβ. WO 99/18987 discloses an isolated peptide of V-domain of a receptor for advance glycation end product (RAGE) and its use for inhibiting the interaction of Aβ with the RAGE to treat degeneration of a neuronal cell. WO 01/12598 discloses a method for inhibiting the binding of a β-sheet fibril, such as amyloid fibril to RAGE on the surface of a cell, by using a fragment of RAGE.

SUMMARY OF THE INVENTION

In one general aspect, the invention is directed to compounds represented by the following formula I:

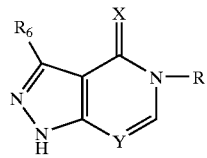

(I)

wherein:
X is O or S;
Y is N or CH;
$R_6$ is H or OH; and
R is

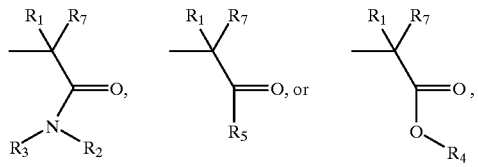

wherein:
$R_1$ is hydrogen or an alkyl, alkenyl, alkynyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;

$R_2$ and $R_3$ are each independently hydrogen or an alkyl, alkenyl, alkoxy, aryl, heteroaryl, cycloalkyl, or heterocycloalkyl group, or $R_2$ and $R_3$ together with the N atom to which they are attached form a 4- to 10-membered heterocycloalkyl or heteroaryl group containing at least one N, S or O heteroatom, where the alkyl, alkenyl, alkoxy, aryl, heteroaryl, cycloalkyl, or heterocycloalkyl group is unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;

$R_4$ is hydrogen or an alkyl, alkenyl, cycloalkyl, heterocycloalkyl, aryl or heteroaryl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$OR_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;

$R_5$ is hydrogen or an alkyl, alkenyl, alkynyl, cycloalkyl, heterocycloalkyl, aryl or heteroaryl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above; and $R_7$ is hydrogen or a $C_1$-$C_3$ alkyl, hydroxy or $C_1$-$C_3$ alkoxy group.

In one preferred embodiment, $R_2$ and $R_3$ together with the N atom to which they are attached form

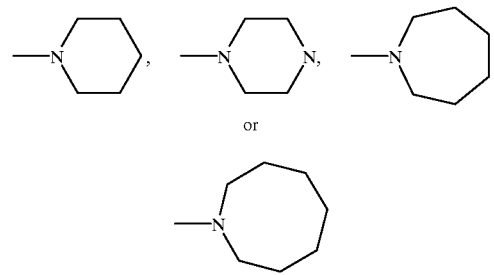

unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above.

In another preferred embodiment, the invention is directed to compounds represented by the formula I:

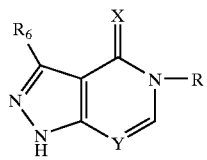

(I)

wherein R is

and wherein
(1) X is O or S;
Y is CH;
$R_6$ is H or OH;
$R_1$ is hydrogen or an alkyl, alkenyl, alkynyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_cSR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —$CSO$—$R_c$, —$CSO_2$—$R_c$, —$NR_c$—CS—$R_d$, —O—CS—$R_c$, —O—$CSO$—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—$CSO$—$R_d$, $NR_c$—CS—$R_d$, —SH, —S—$R_b$, and —$PO_2$—$OR_c$, where alkyl, heteroalkyl, alkenyl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;
$R_7$ is hydrogen or a $C_1$–$C_3$ alkyl, hydroxy or $C_1$–$C_3$ alkoxy group; and
$R_8$ is hydrogen or an alkyl, alkenyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —$CSO$—$R_c$, —$CSO_2$—$R_c$, —$NR_c$—CS—$R_d$, —O—CS—$R_c$, —O—$CSO$—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—$CSO$—$R_d$, $NR_c$—CS—$R_d$, —SH, —S—$R_b$, and —$PO_2$—$OR_c$, where alkyl, heteroalkyl, alkenyl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;

(2) X is O or S;
   Y is N;
   $R_6$ is OH;
   $R_1$ is hydrogen or an alkyl, alkenyl, alkynyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —$CSO$—$R_c$, —$CSO_2$—$R_c$, —$NR_c$—CS—$R_d$, —O—CS—$R_c$, —O—$CSO$—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—$CSO$—$R_d$, $NR_c$—CS—$R_d$, —SH, —S—$R_b$, and —$PO_2$—$OR_c$, where alkyl, heteroalkyl, alkenyl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;
   $R_7$ is hydrogen or a $C_1$–$C_3$ alkyl, hydroxy or $C_1$–$C_3$ alkoxy group; and
   $R_8$ is hydrogen or an alkyl, alkenyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —$CSO$—$R_c$, —$CSO_2$—$R_c$, —$NR_c$—CS—$R_d$, —O—CS—$R_c$, —O—$CSO$—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—$CSO$—$R_d$, $NR_d$—CS—$R_d$, —SH, —S—$R_b$, and —$PO_2$—$OR_c$, where alkyl, heteroalkyl, alkenyl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;

(3) X is S;
   Y is N;
   $R_6$ is H or OH;
   $R_1$ is an alkyl, alkenyl, alkynyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where alkyl, heteroalkyl, alkenyl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;

$R_7$ is hydrogen or a $C_1$–$C_3$ alkyl, hydroxy or $C_1$–$C_3$ alkoxy group; and $R_8$ is hydrogen or an alkyl, alkenyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where alkyl, heteroalkyl, alkenyl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above; or (4) X is O;

Y is N;

$R_6$ is H;

$R_1$ is an alkyl, alkenyl, alkynyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where alkyl, heteroalkyl, alkenyl, and alkynyl, $R_b$ is selected from the group consisting of alkyl, heteroalkyl, haloalkyl, alkenyl, alkynyl, —CO—

$R_c$, —CO—O$R_c$, —O—CO—O—$R_c$, —O—CO—$R_c$, —N$R_c$—CO—$R_d$, —CO—N$R_d R_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —CO$R_f$, —COO$R_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—O$R_c$, —N$R_d R_e$, —CO—N$R_d R_e$, —CO—O$R_c$, —CO—$R_c$, —N$R_c$—CO—N$R_d R_e$, —C—CO—O$R_c$, —N$R_c$—CO—$R_d$, —O—CO—O—$R_c$, O—CO—N$R_d R_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;

$R_7$ is hydrogen or a $C_1$–$C_3$ alkyl, hydroxy or $C_1$–$C_3$ alkoxy group; and $R_8$ is an alkenyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—O$R_c$, —CN, —$(CH_2)_z$—CN where z is an integer from 0 to 4, halogen, —OH, —O—$R_a$—O—, —O$R_b$, —CO—$R_c$, O—CO—$R_c$, CO—O$R_c$, —O—CO—O$R_c$, —O—CO—O—CO—$R_c$, —O—O$R_c$, =O, =S, $SO_2$—$R_c$, —SO—$R_c$, —N$R_d R_e$, —CO—N$R_d R_e$, —O—CO—N$R_d R_e$, —N$R_c$—CO—N$R_d R_e$, —N$R_c$—CO—$R_e$, N$R_c$—CO—O$R_e$, —CO—N$R_c$—CO—$R_d$, —O—$SO_2$—$R_c$, —O—SO—$R_c$, —O—S—$R_c$, —S—CO—$R_c$, —SO—CO—O$R_c$, —$SO_2$—CO—O$R_c$, —O—$SO_3$, —N$R_c$—S$R_d$, —N$R_c$—SO—$R_d$, N$R_c$—$SO_2$—$R_d$, —CO—S$R_c$, —CO—SO—$R_c$, CO—$SO_2$—$R_c$, —CS—$R_c$, —CSO—$R_c$, —$CSO_2$—$R_c$, —N$R_c$—CS—$R_d$, —O—CS—$R_c$, —O—CSO—$R_c$, O—$CSO_2$—$R_c$, —$SO_2$—N$R_d R_e$, —SO—N$R_d R_e$, —S—N$R_d R_e$, —N$R_d$—$CSO_2$—$R_d$, —N$R_c$—CSO—$R_d$, N$R_c$—CS—$R_d$, —SH, —S—$R_b$, and —$PO_2$—O$R_c$, where alkyl, heteroalkyl, alkenyl, and alkynyl, $R_b$ is selected from the group consisting of alkyl, heteroalkyl, haloalkyl, alkenyl, alkynyl, —CO—$R_c$, —CO—O$R_c$, —O—CO—O—$R_c$, —O—CO—$R_c$, —N$R_c$—CO—$R_d$, —CO—N$R_d R_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —CO$R_f$, —COO$R_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—O$R_c$, —N$R_d R_e$, —CO—N$R_d R_e$, —CO—O$R_c$, —CO—$R_c$, —NR—CO—N$R_d R_e$, —C—CO—O$R_c$, —N$R_c$—CO—$R_d$, —O—CO—O—$R_c$, O—CO—N$R_d R_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above.

The invention is also directed to pharmaceutically acceptable prodrugs, pharmaceutically active metabolites, and pharmaceutically acceptable salts of the compounds of Formula I as well as pharmaceutically acceptable salts of such active metabolites. The compounds of Formula I, salts, prodrugs, metabolites and salts thereof are collectively referred to as "ERAB or HADH2 inhibiting agents."

The invention further provides a method of modulating or inhibiting ERAB or HADH2 activity comprising administering a therapeutically effective amount of one or more ERAB or HADH2 inhibiting agents to a patient in need thereof.

The present invention also relates to a method of treating ERAB, HADH2 or amyloid-β mediated diseases, such as certain cancers and progressive neurodegenerative diseases, comprising administering therapeutically effective amounts of one or more ERAB or HADH2 inhibiting agents to apatient in need of such treatment.

The present invention also relates to a method of treating ERAB or HADH2-mediated neuronal dysfunction or cytotoxicity in the Aβ-rich environment present in, for example, AD or related Aβ-mediated dementia, comprising administering therapeutically effective amounts of one or more ERAB or HADH2 inhibiting agent(s) to a patient in need of such treatment.

Another aspect of the invention includes combination therapies for treating amyloid-β mediated or ERAB or HADH2 mediated diseases or conditions comprising administering the ERAB or HADH2 inhibiting agents of the invention in combination with other known treatments for amyloid-β mediated or ERAB or HADH2 mediated diseases.

There is also provided, in accordance with the invention, a pharmaceutical composition containing one or more ERAB or HADH2 inhibiting agents and a pharmaceutically acceptable carrier, diluent or vehicle.

Additional aspects, features, embodiments and advantages of the present invention will be apparent from the description that follows, or may be learned from practicing or using the present invention.

DETAILED DESCRIPTION OF THE INVENTION

As used herein, diseases and conditions mediated by ERAB, HADR2 or amyloid-β are understood to include, for example, neurodegenerative diseases, such as Alzheimer's disease ("AD") or related Aβ-mediated dementia, and certain cancers, such as breast and endometrium cancers (see He et al., *J. Biol. Chem.*, 274(21), 15014–15019 (1999)).

In accordance with a convention used in the art, the symbol

represents a methyl group,

represents an ethyl group,

represents a cyclopentyl group, etc.

The terms "comprising" and "including" are used herein in their open, non-limiting sense.

The term "alkyl" as used herein refers to straight- and branched-chain alkyl groups having from one to twelve carbon atoms. Exemplary alkyl groups include methyl (Me), ethyl, n-propyl, isopropyl, butyl, isobutyl, secbutyl, tert-butyl (tBu), pentyl, isopentyl, tert-pentyl, hexyl, isohexyl, and the like.

The term "heteroalkyl" as used herein refers to straight- and branched-chain alkyl groups having from one to twelve atoms containing one or more hebroatoms selected from S, O, and N.

The term "alkenyl" refers to straight- and branched-chain alkenyl groups having from two to twelve carbon atoms. Illustrative alkenyl groups include prop-2-enyl, but-2-enyl, but-3-enyl, 2-methylprop-2-enyl, hex-2-enyl, and the like. The term "allyloxy" refers to an alkenyl group as defined above which is $CH_2=CHCH_2-O-$.

The term "alkynyl" refers to straight- and branched-chain alkynyl groups having from two to twelve carbon atoms. Illustrative alkynyl groups include prop-2-ynyl, but-2-ynyl, but-3-ynyl, 2-methylbut-2-ynyl, hex-2-ynyl, and the like.

The term "aryl" (Ar) refers to monocyclic and polycyclic aromatic ring structures containing only carbon and hydrogen. Illustrative examples of aryl groups include the following moieties:

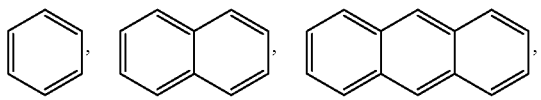

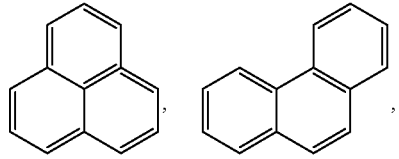

and the like.

The term "heteroaryl" (heteroAr) refers to monocyclic and polycyclic aromatic ring structures which include one or more heteroatoms selected from nitrogen, oxygen and sulfur. The polycyclic heteroaryl group may be fused or non-fused. Illustrative examples of aryl groups include the following moieties:

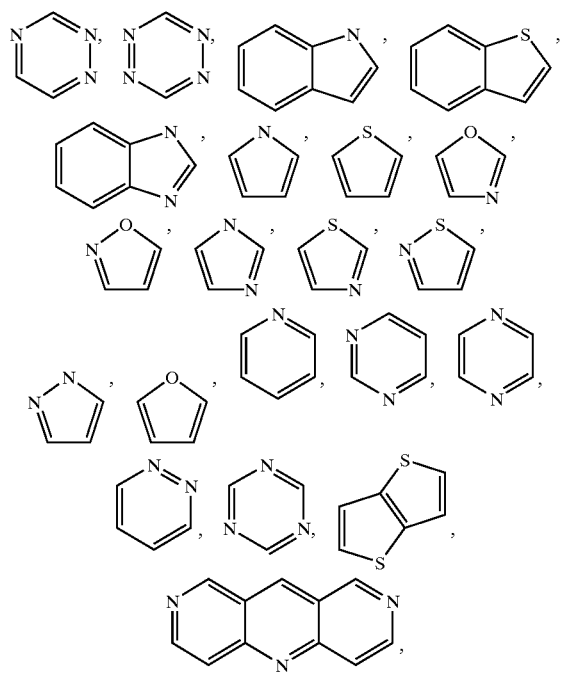

and the like.

The term "cycloalkyl" refers to saturated carbocycles having from three to twelve carbon atoms, including bicyclic and tricyclic cycloalkyl structures. Illustrative examples of cycloalkyl groups include the following moieties:

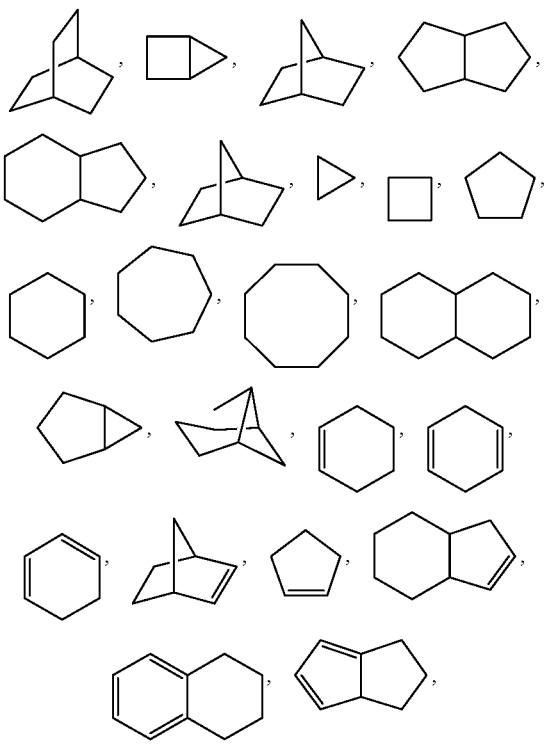

and the like.

A "heterocycloalkyl" group refers to a monocyclic or polycyclic radical which may be saturated or unsaturated and contains from three to twelve ring atoms selected from carbon and heteroatoms, preferably 4 or 5 ring carbon atoms, and at least one heteroatom selected from nitrogen, oxygen and sulfur. The radicals may be fused with an aryl or heteroaryl. Illustrative examples of heterocycloalkyl groups include,

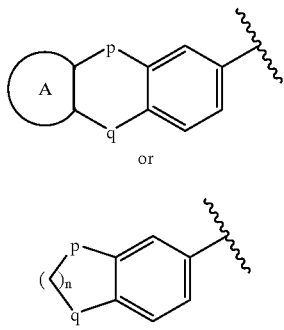

where A is an aryl or heteroaryl group, p and q are each independently O, N, or S (all combinations) and n is 1, 2, 3, or 4.

Additional illustrative examples of heterocycloalkyl groups include,

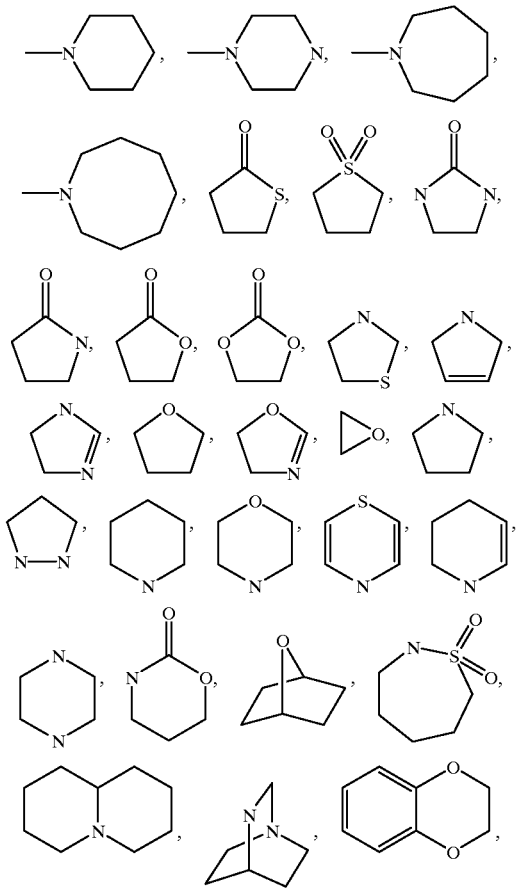

and the like.

The term "alkoxy" refers to the radical —O—R where R is an alkyl as defined above. Examples of alkoxy groups include methoxy, ethoxy, propoxy, and the like.

The term "halogen" represents chlorine, fluorine, bromine or iodine. The term "halo" represents chloro, fluoro, bromo or iodo. The term "haloalkyl" refers to an alkyl group as defined above containing one or more chloro, fluoro, bromo or iodo atoms (or combinations thereof). The term "haloaryl" refers to an aryl group as defined above containing one or more chloro, fluoro, bromo or iodo atoms (or combinations thereof). The term "halocycloalkyl" refers to a cylcoalkyl group as defined above containing one or more chloro, fluoro, bromo or iodo atoms (or combinations thereof). The term "haloheterocycloalkyl" refers to a heterocycloalkyl group as defined above containing one or more chloro, fluoro, bromo or iodo atoms (or combinations thereof).

The term "alcohol" refers to the radical —R—OH where R is alkyl, alkenyl, alkynyl, Ar, heteroaryl, heterocycloalkyl, or cycloalkyl as defined above. Examples of alcohols include methanol, ethanol, propanol, phenol and the like.

The term "acyl" represents —C(O)R, —C(O)OR, —OC(O)R or —OC(O)OR where R is alkyl, alkenyl, alkynyl, Ar, heteroaryl, heterocycloalkyl, or cycloalkyl as defined as above.

The term "amide" refers to the radical —C(O)N(R')(R") where R' and R" are each independently selected from hydrogen, —OH and alkyl, alkenyl, alkynyl, alkoxy, cycloalkyl, heterocycloalkyl, heteroaryl, aryl groups as defined above; or R' and R" cyclize together with the nitrogen to form a heterocycloalkyl or heteroaryl as defined above.

The term "substituted" as used herein means that the group in question may bear one or more substituents. If the substituents themselves are not compatible with the synthetic methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are known to those skilled in the art; examples of which may be found in T. Greene and P. Wuts, Protecting Groups in Chemical Synthesis (3rd ed.), John Wiley & Sons, NY (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

Preferred compounds of the invention include the following compounds, as well as any other compound(s) described in the Examples below:

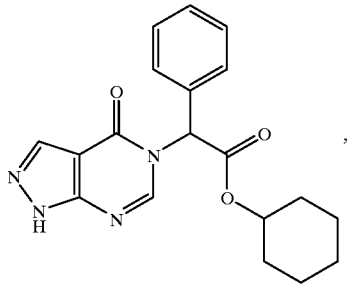

-continued
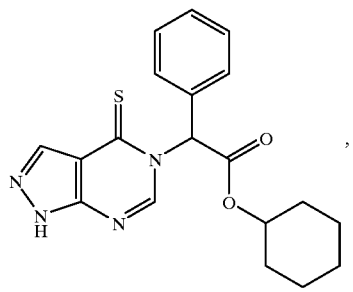
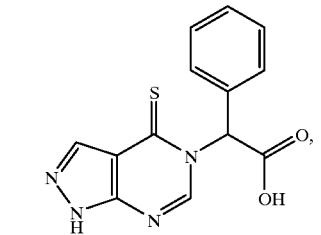
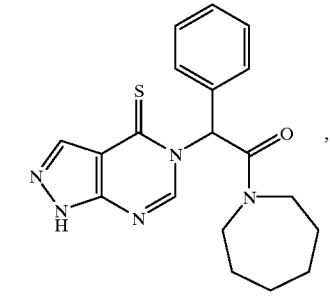
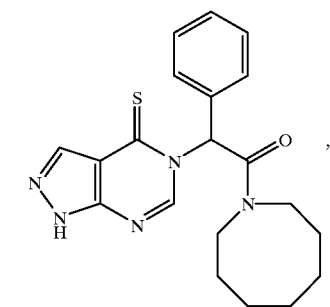
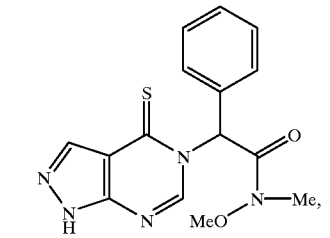
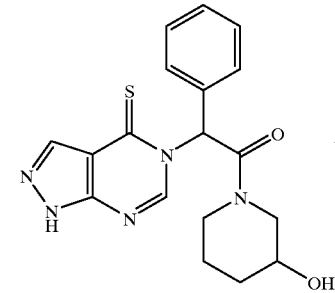
-continued
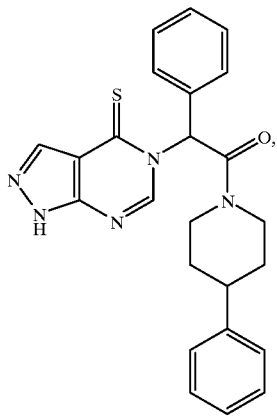
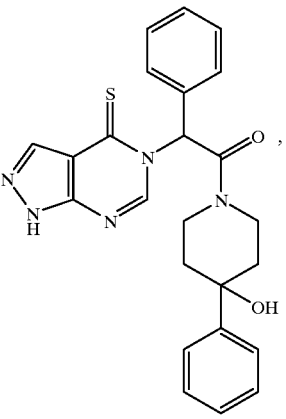
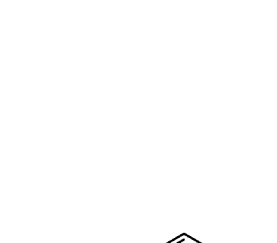
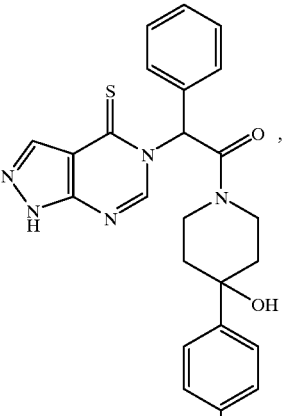

-continued
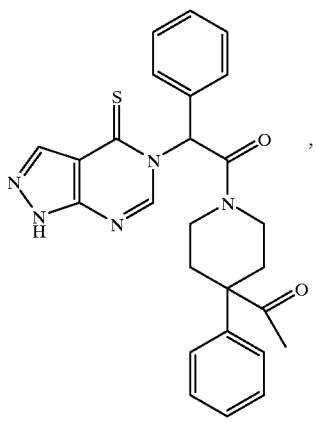
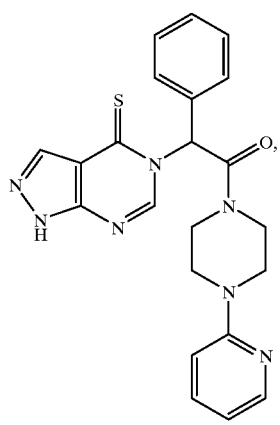
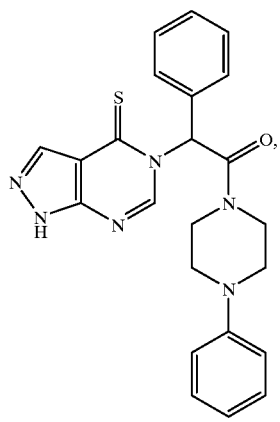
-continued
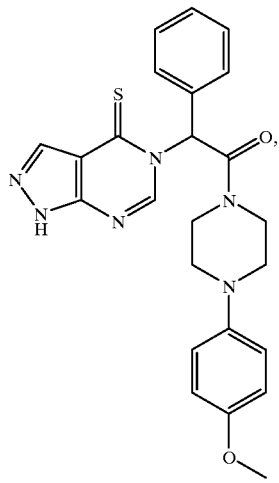
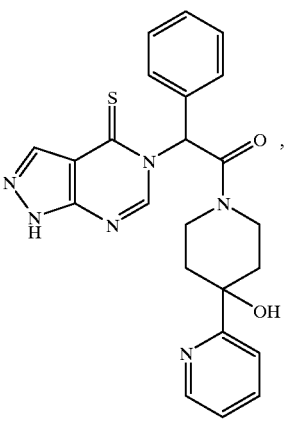
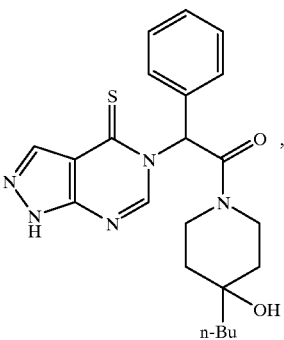
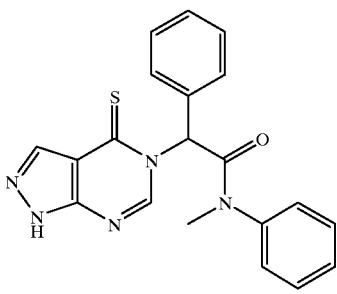

-continued
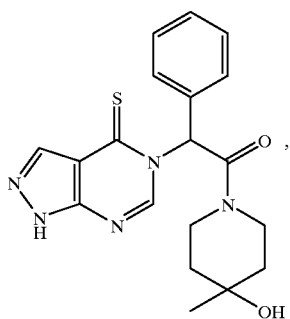
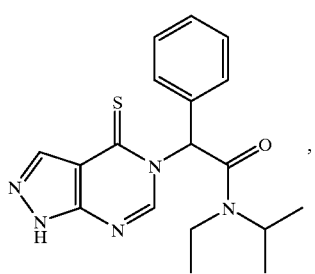
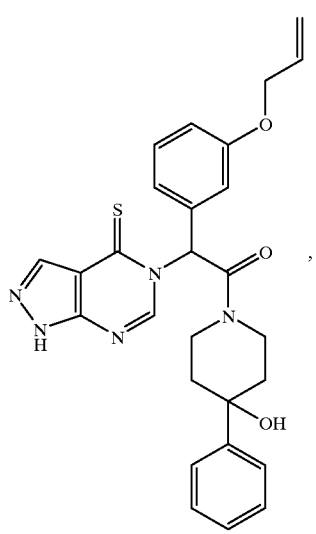
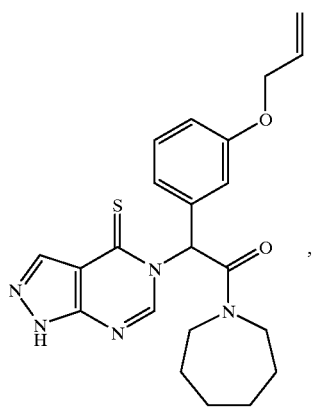
-continued
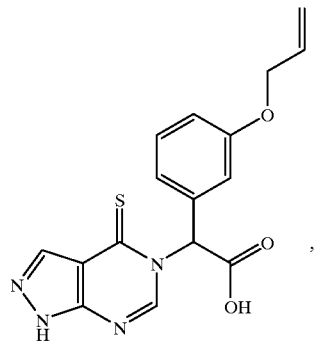
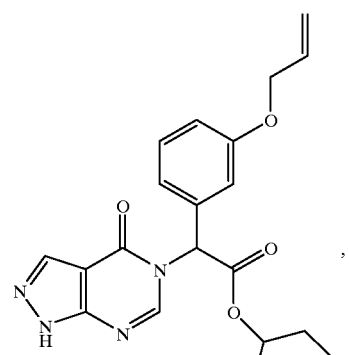
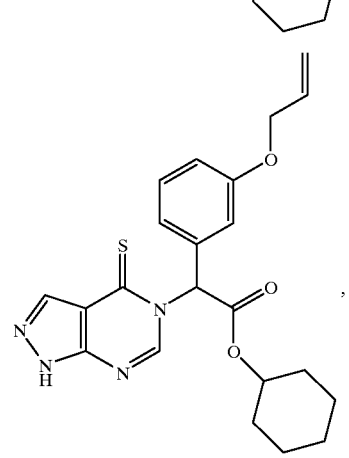
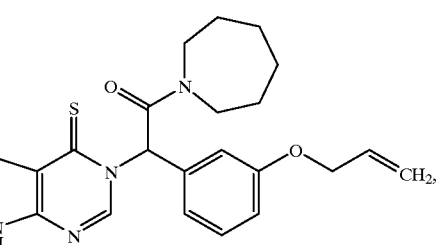
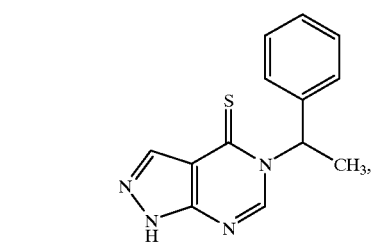

-continued
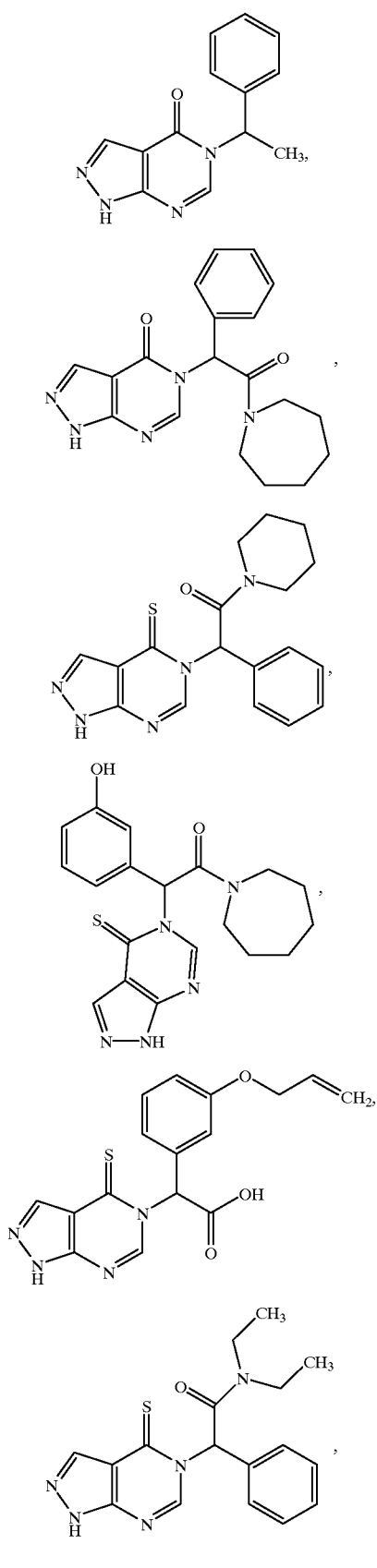
-continued
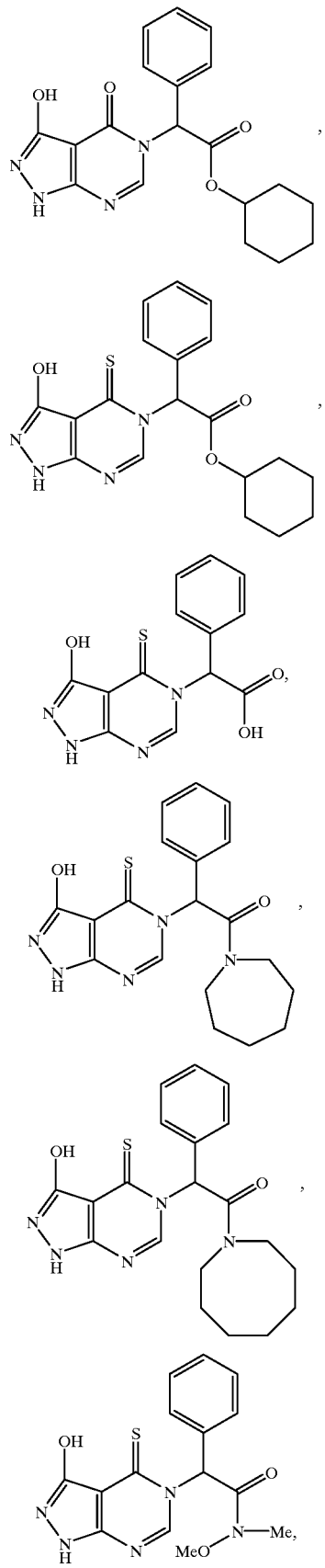

-continued
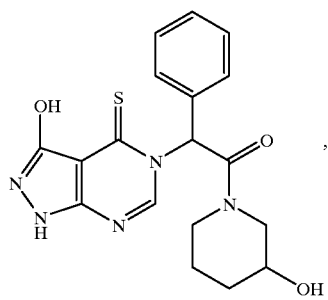
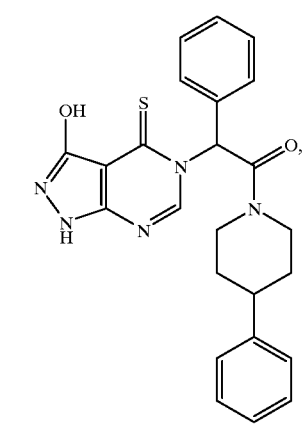
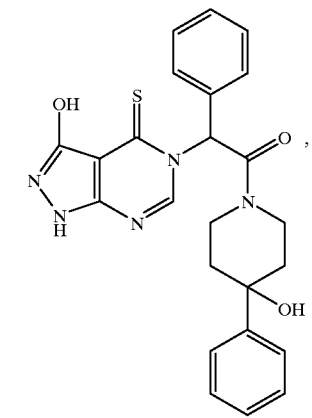
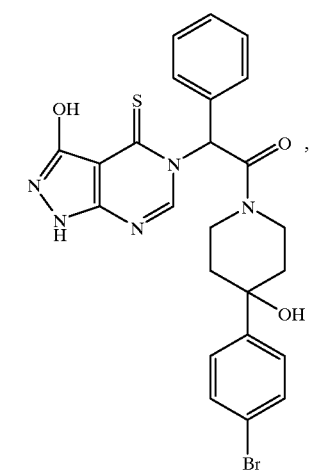
-continued
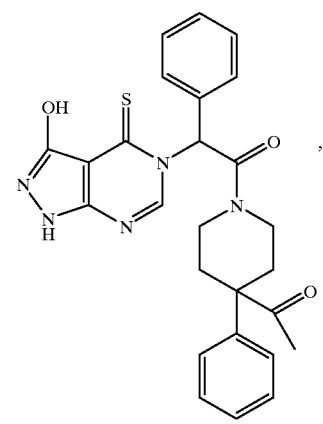
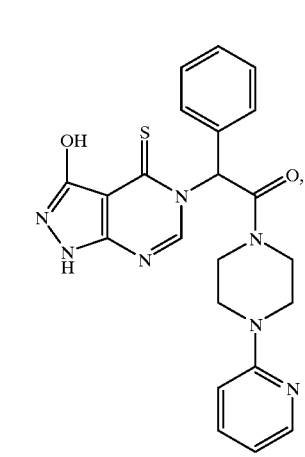
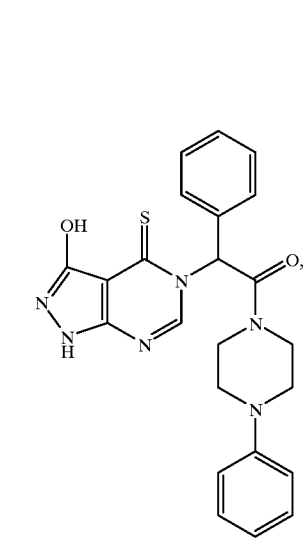

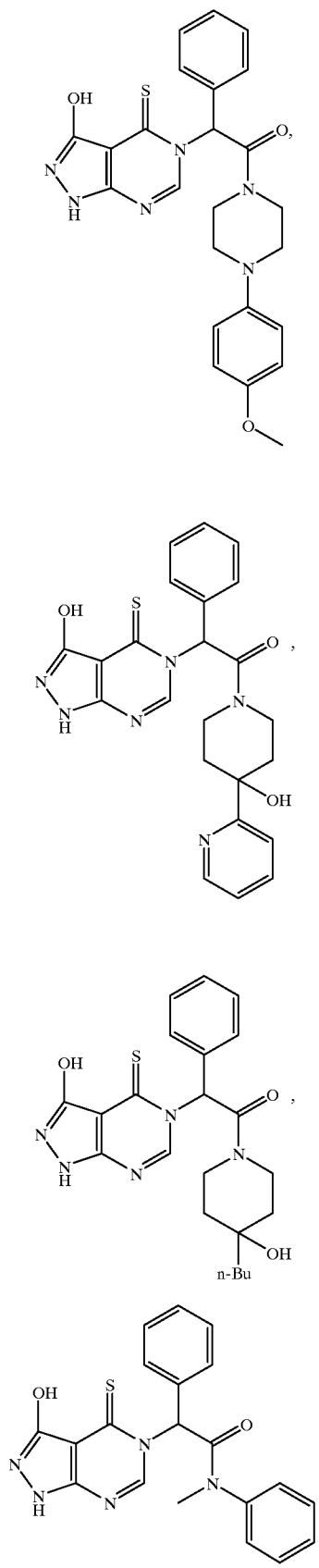
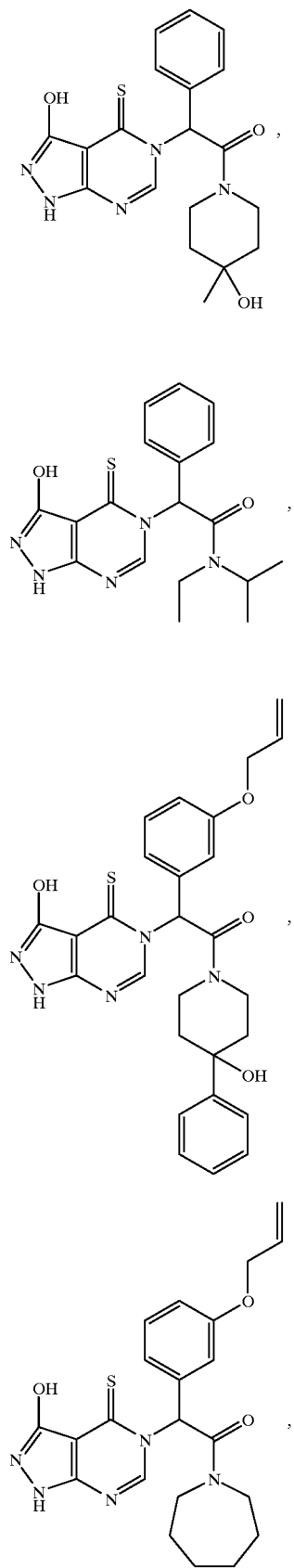

-continued
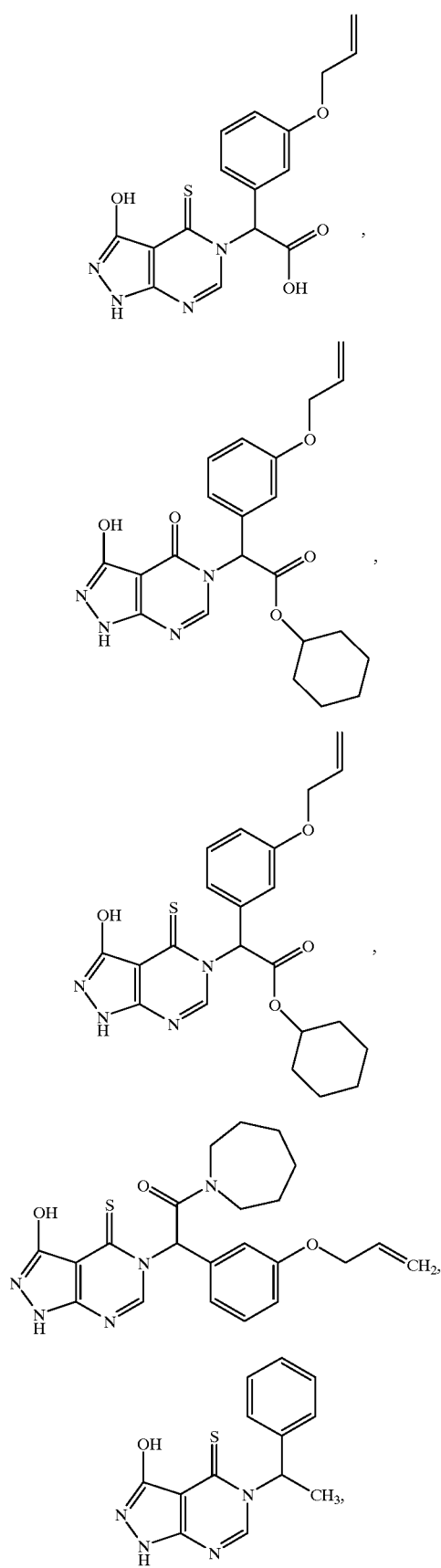
-continued
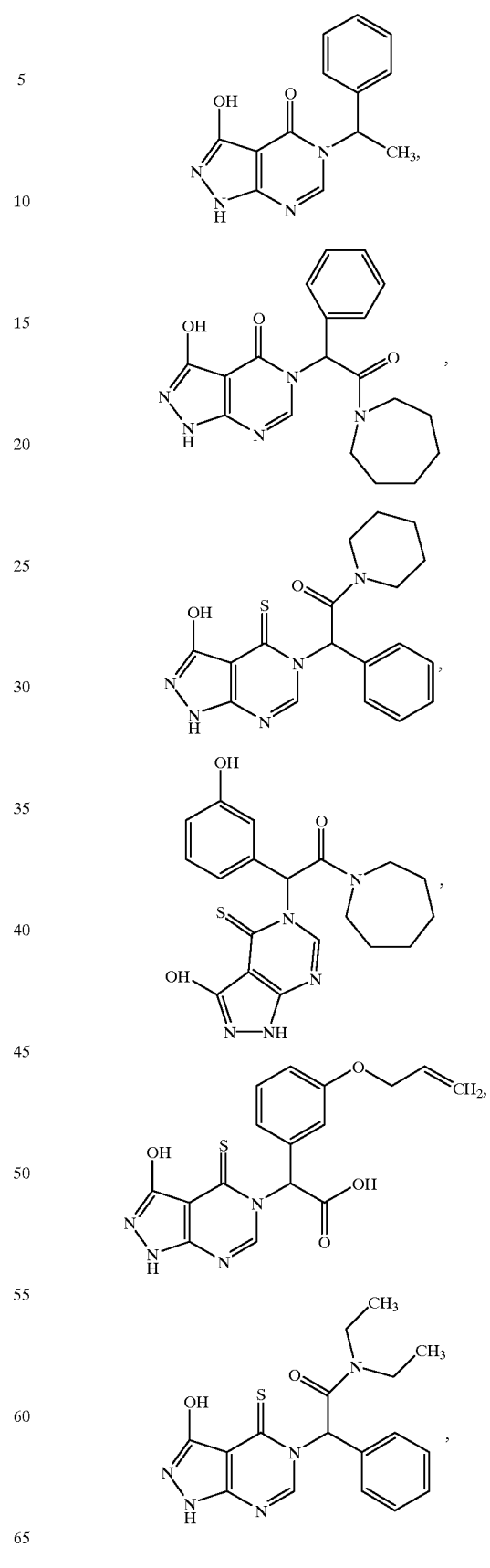

-continued
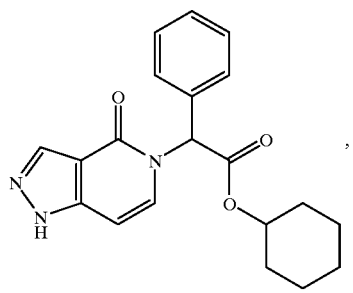,
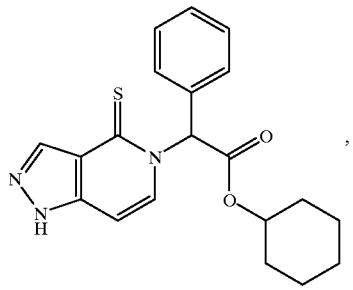,
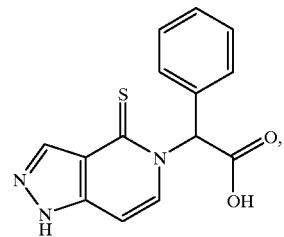,
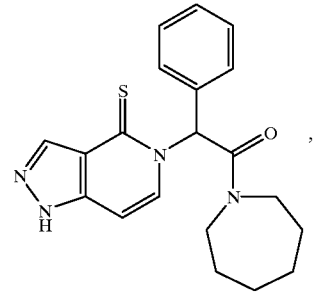,
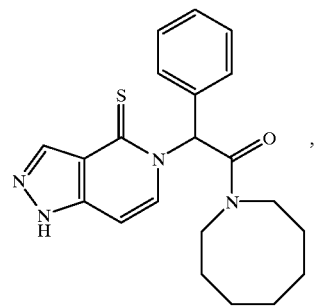,
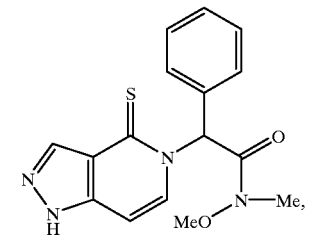
-continued
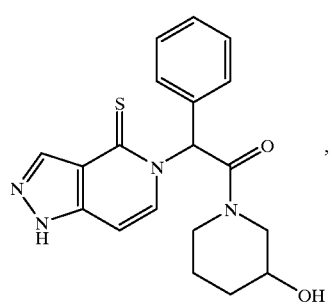,
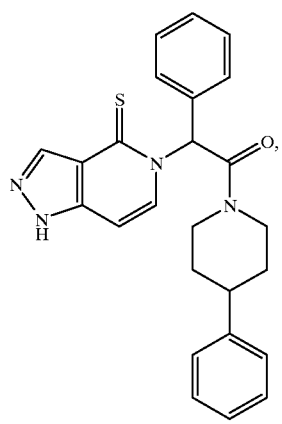,
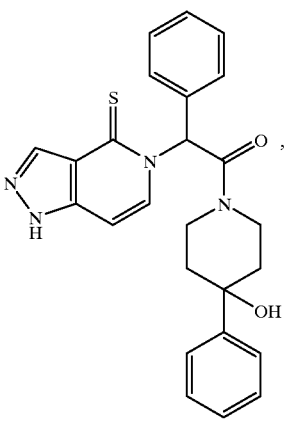,
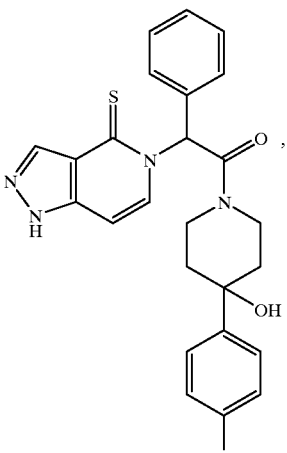,

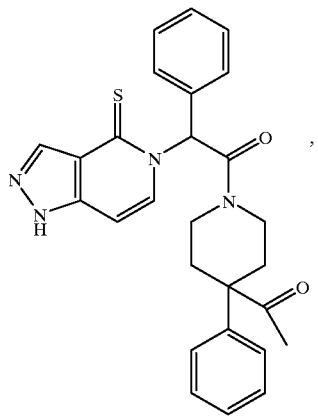
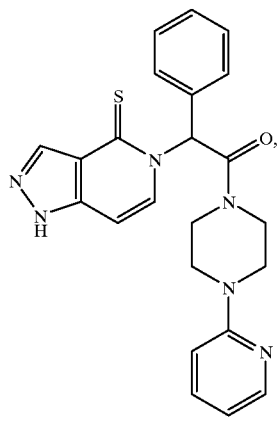
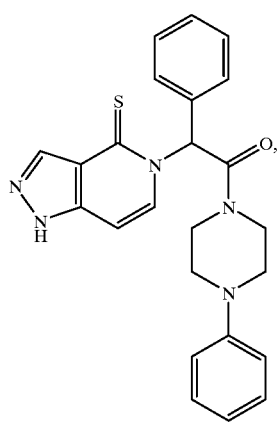
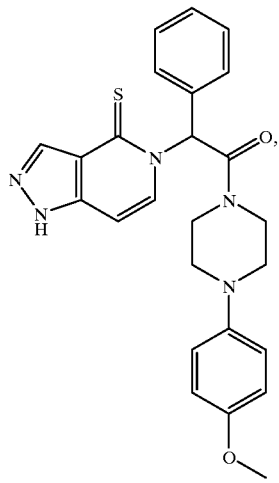
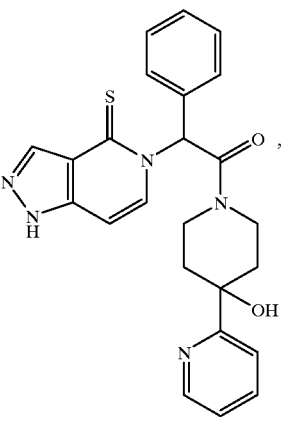
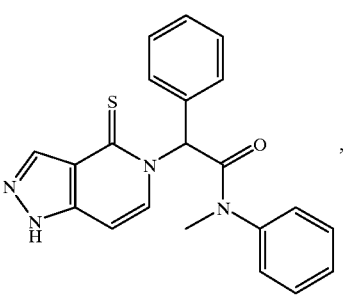

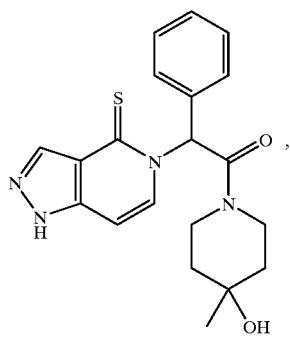
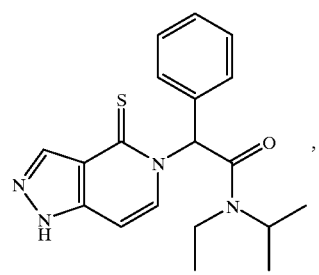
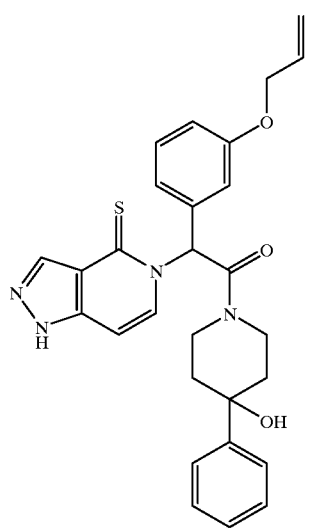
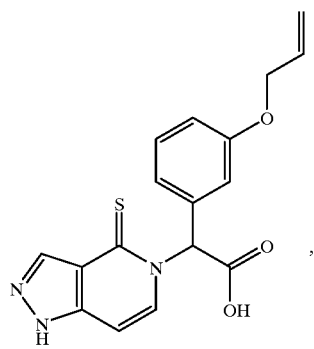
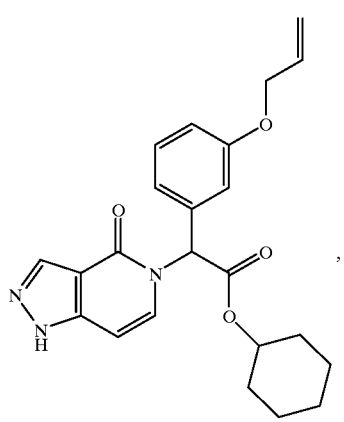
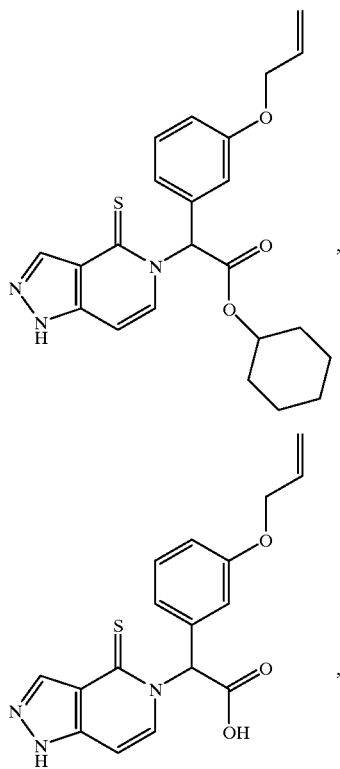

-continued
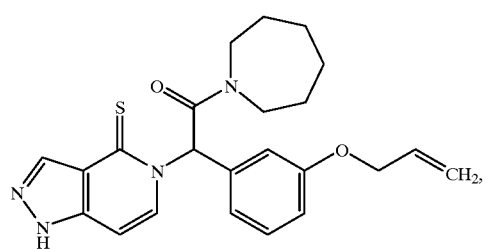
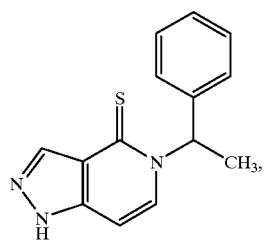
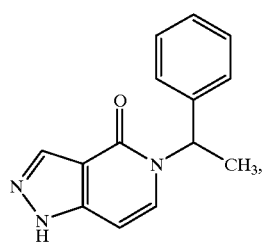
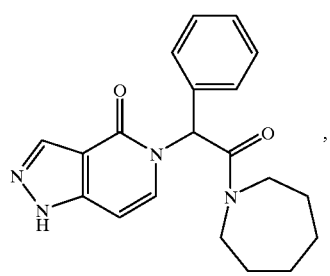
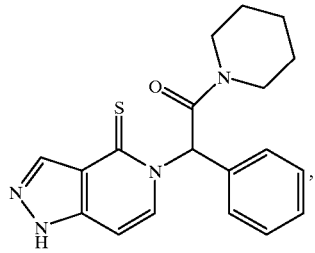
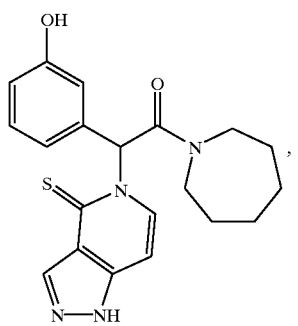
-continued
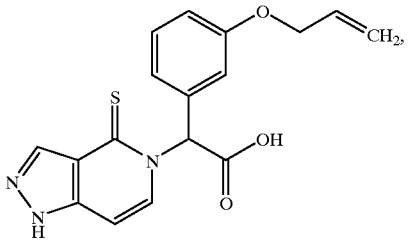
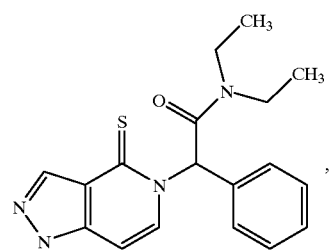
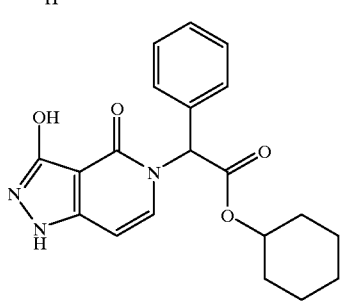
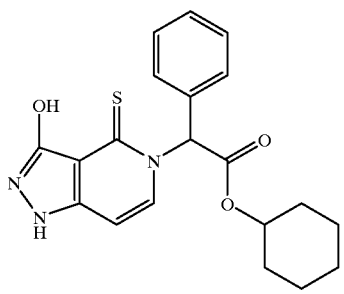
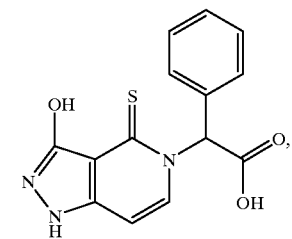
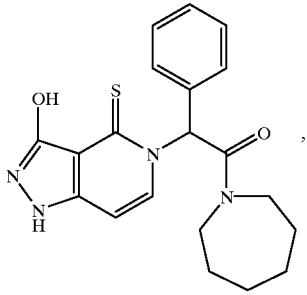

-continued
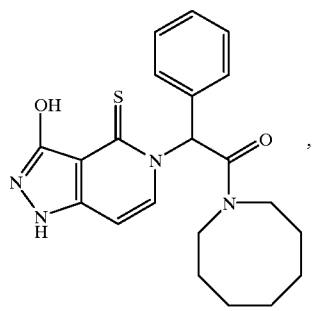
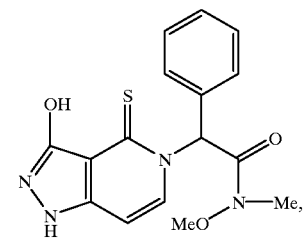
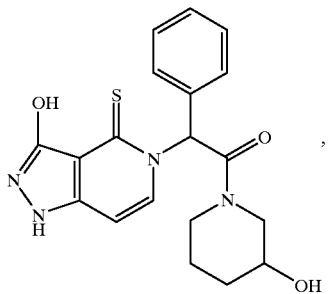
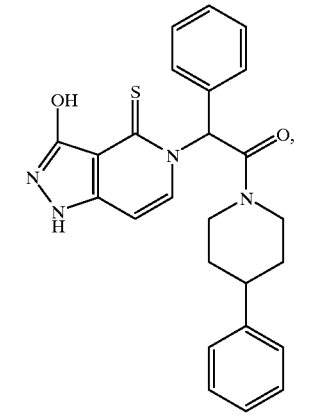
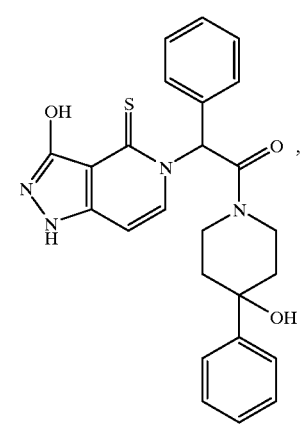
-continued
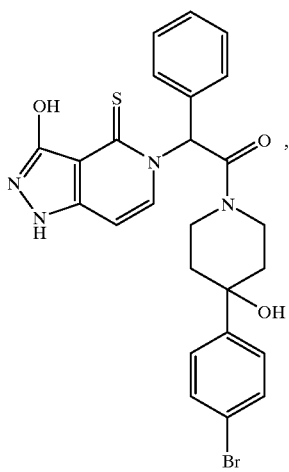
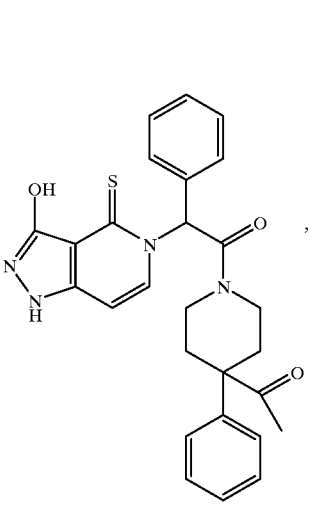
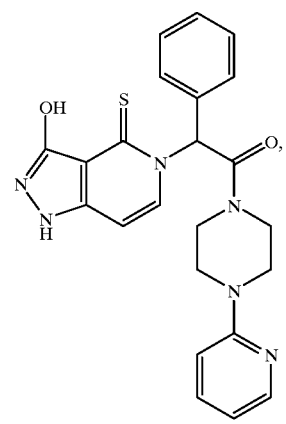

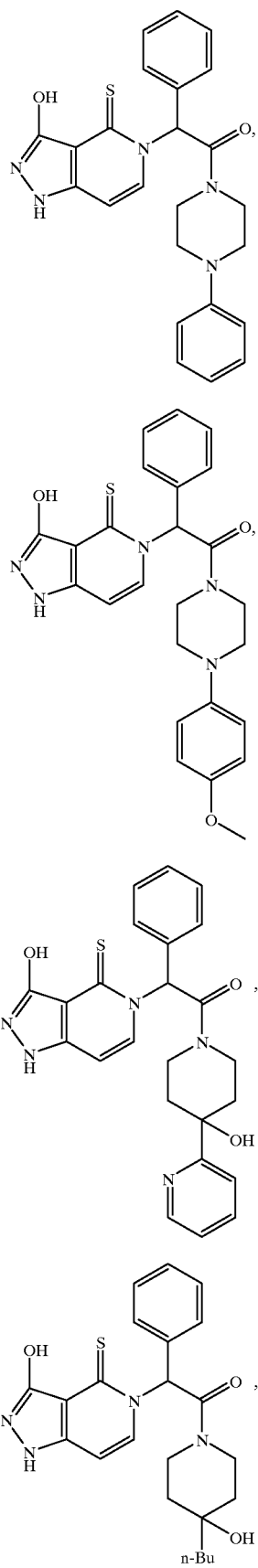
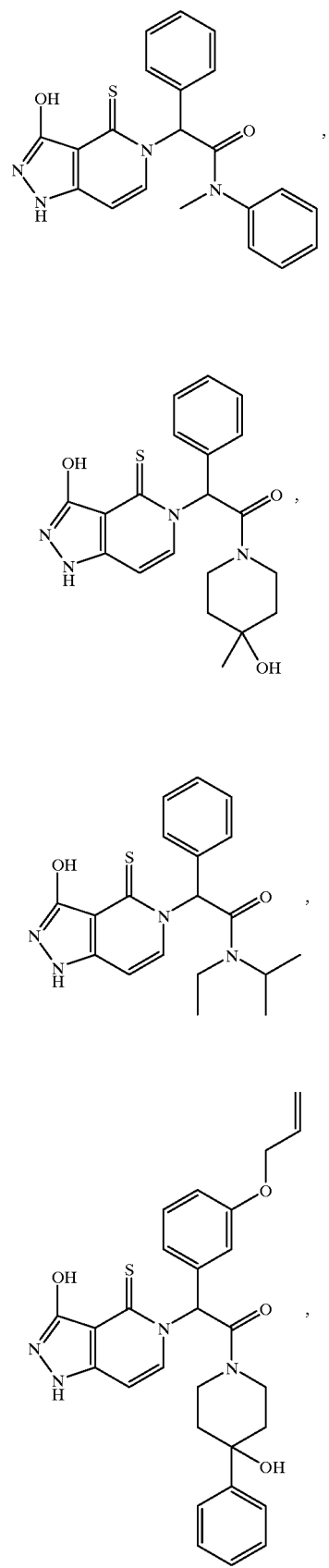

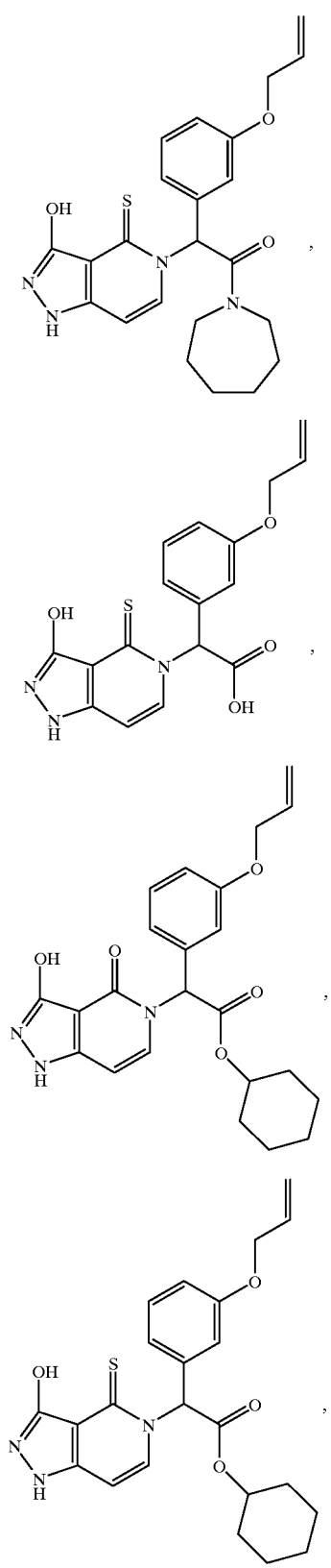
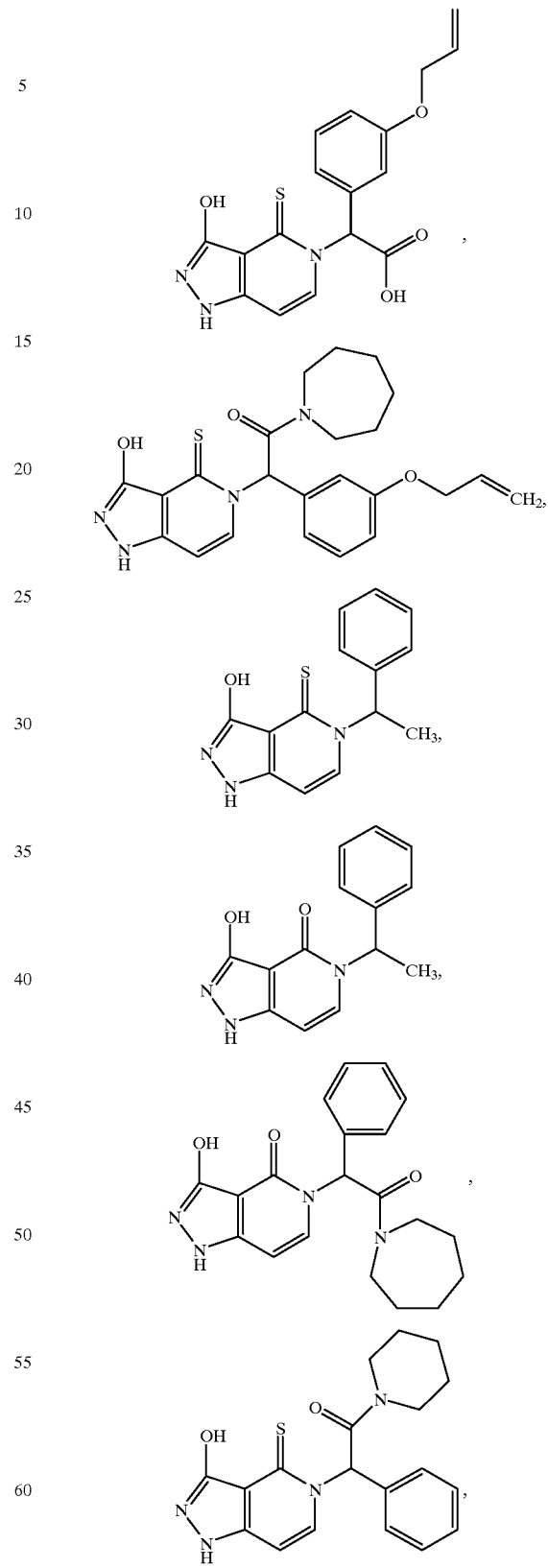

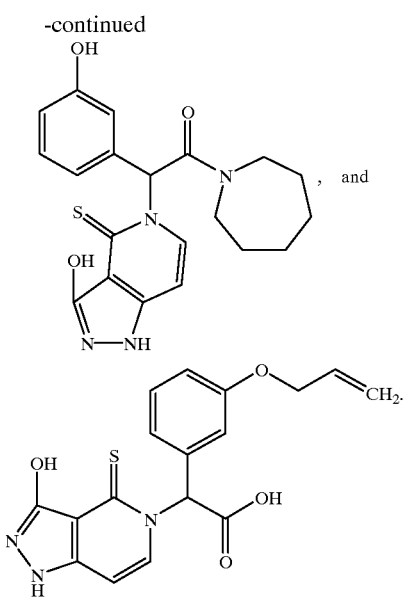

Some of the ERAB or HADH2 inhibiting agents may exist in various stereoisomeric or tautomeric forms. The present invention encompasses all such agents, including active compounds in the form of single pure enantiomers (i.e., essentially free of other stereoisomers), racemates, mixtures of enantiomers and/or diastereomers, and/or tautomers. Preferably, the ERAB or HADH2 inhibiting agents that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure.

Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the formulae are intended to cover solvated as well as unsolvated forms of the identified compounds. For example, Formula I includes compounds of the indicated structure in both hydrated and non-hydrated forms. Additional examples of solvates include the compounds of Formula I associated with isopropanol, ethanol, methanol, DMSO, ethyl acetate, acetic acid, or ethanolamine.

The term "pharmaceutically acceptable" means pharmacologically acceptable and substantially non-toxic to the subject being administered the ERAB or HADH2 inhibiting agent.

"A pharmaceutically acceptable prodrug" is a compound that is converted under physiological conditions or by in vivo solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art. See, e.g., Bertolini et al., *J. Med. Chem.*, 40, 2011–2016 (1997); Shan et al., *J. Pharm. Sci.*, 86 (7), 765–767; Bagshawe, *Drug Dev. Res.*, 34, 220–230 (1995); Bodor, *Advances in Drug Res.*, 13, 224–331 (1984); Bundgaard, *Design of Prodrugs* (Elsevier Press 1985); Larsen, *Design and Application of Prodrugs, Drug Design and Development* (Krogsgaard-Larsen et al., eds., Harwood Academic Publishers, 1991); Dear et al., *J. Chromatogr. B*, 748, 281–293 (2000); Spraul et al., *J. Pharmaceutical & Biomedical Analysis*, Vol. 10, No. 8, 601–605 (1992); and Prox et al., *Xenobiol* Vol. 3, No. 2, 103–112 (1973).

"A pharmaceutically acceptable salt" is intended to mean a salt that retains the biological effectiveness of the free acids and bases of the specified compound and that is not biologically or otherwise undesirable. An ERAB or HADH2 inhibiting agent may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the ERAB or HADH2 inhibiting compound is a base, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, phosphoric acid and the like, or with an organic acid, such as acetic acid, phenylacetic acid, propionic acid, stearic acid, lactic acid, ascorbic acid, maleic acid, hydroxymaleic acid, isethionic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid, 2-acetoxybenzoic acid or cinnamic acid, a sulfonic acid, such as p-toluenesulfonic acid, methanesulfonic acid or ethanesulfonic acid, or the like.

If the ERAB or HADH2 inhibiting agent is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine and piperazine, and inorganic salts derived from sodium, calcium, potassium, magnesium, manganese, iron, copper, zinc, aluminum and lithium.

In the case of compounds that are solids, it is understood by those skilled in the art that the ERAB or HADH2 inhibiting agents and salts may exist in different crystal or polymorphic forms, all of which are intended to be within the scope of the present invention and specified formulas.

Compounds that modulate or inhibit ERAB or HADH2 are desirable and are one preferred embodiment of the present invention. The present invention is further directed to methods of modulating or inhibiting ERAB or HADH2, for example in mammals, by administering an effective amount of one or more ERAB or HADH2 inhibiting agent. The activity of the ERAB or HADH2 inhibiting agents as inhibitors of ERAB or HADH2, may be measured by any of the methods available to those skilled in the art, including in vivo and/or in vitro assays. Examples of suitable assays for activity measurements include those described in Binstock et al., *Methods Enzymol.* 71,403–411 (1981).

The ERAB or HADH2 inhibiting agents of the invention preferably have an $IC_{50}$ against ERAB activity of less than or equal to 600 µM. More preferably, the ERAB or HADH2 inhibiting agents of the invention have an $IC_{50}$ against ERAB activity of less than or equal to 50 µM. Most preferably, the ERAB or HADH2 inhibiting agents of the invention have an $IC_{50}$ against ERAB activity of less than or equal to 3.0 µM.

A therapeutically "effective amount" is intended to mean that amount of a compound that, when administered to a mammal in need of such treatment, is sufficient to effect treatment, as defined herein. Thus, e.g., a therapeutically effective amount of a compound of the Formula I, salt, active metabolite or prodrug thereof is a quantity sufficient to modulate or inhibit the activity of ERAB such that a disease condition which is mediated by that activity is reduced or alleviated. The amount of a given compound that will correspond to such an amount will vary depending upon factors such as the particular compound, disease condition and its severity, the identity (e.g., weight) of the mammal in need of treatment, but can nevertheless be routinely determined by one skilled in the art. Likewise, the duration of treatment and time period of administration of the compound will vary according to the identity of the mammal in need of treatment (e.g., weight), the particular compound and its properties (e.g., pharmaceutical characteristics), disease or condition and its severity of the illness and the specific composition and method being used, but can nevertheless be determined by one of skill in the art.

The terms "treating", "treat" and "treatment" refer to any treatment of an ERAB, HADH2, or amyloid-β mediated disease or condition in a mammal, particularly a human, and include: (i) preventing the disease or condition from occurring in a subject which may be predisposed to the condition, for example subjects with accumulated Aβ peptides, such that the treatment constitutes prophylactic treatment for the pathologic condition; (ii) modulating or inhibiting the disease or condition, i.e., arresting its development; (iii) relieving the disease or condition, i.e., causing regression of the disease or condition; or (iv) relieving and/or alleviating disease or condition or the symptoms resulting from the disease or condition, e.g., relieving an inflammatory response without addressing the underlining disease or condition.

The ERAB or HADH2 inhibiting agents may be formulated into pharmaceutical compositions as described below. Additionally, the ERAB or HADH2 inhibiting agents may be administered either alone or in combination with other compounds effective for modulating or inhibiting ERAB or HADH2 or treating ERAB or HADH2 mediated diseases or conditions. For example, the ERAB or HADH2 inhibiting agents may be administered in combination with other agents used to treat ERAB, HADH2 or amyloid-β mediated diseases or conditions, such as estrogen, NSAIDS, risperidone, a thiobenzodiazepine, ampakine, [N(2,6-dimethylphenyl)-2-(2-oxo-1-pyrrolidinyl)acetamide, DM9384, a cholinesterase inhibitor, donepezil hydrochloride, rivastigmine tartrate, galantamine, NGF, and metrifonate.

Pharmaceutical compositions of this invention comprise an effective amount of one or more ERAB or HADH2 inhibiting agent and, optionally, an inert, pharmaceutically acceptable carrier or diluent. In one embodiment, the pharmaceutical composition comprise efficacious levels of the ERAB or HADH2 inhibiting agents so as to provide therapeutic benefits involving modulation or inhibition of ERAB or HADH2. By "efficacious levels" is meant levels in which the effects of ERAB or HADH2, at a minimum, are regulated. These compositions are prepared in unit-dosage form appropriate for the mode of administration, e.g., parenteral or oral administration. An ERAB or HADH2 inhibiting agent is administered in conventional dosage form prepared by combining a therapeutically effective amount of a compound (e.g., a compound of Formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxymethylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g., parenteral or oral administration.

To obtain a stable water-soluble dose form, a pharmaceutically acceptable salt of an inventive agent may be dissolved in an aqueous solution of an organic or inorganic acid, such as 0.3 M solution of succinic acidor citric acid. If a soluble salt form is not available, the agent may be dissolved in a suitable cosolvent or combinations of cosolvents. Examples of suitable cosolvents include alcohol, propylene glycol, polyethylene glycol 300, polysorbate 80, glycerin and the like in concentrations ranging from 0–60% of the total volume. In an exemplary embodiment, an ERAB or HADH2 inhibiting agent is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration chosen. For injection, the agents of the invention may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For administration to the eye, an ERAB or HADH2 inhibiting agent may be delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and scelera. The pharmaceutically acceptable ophthalmic vehicle may be an ointment, vegetable oil, or an encapsulating material. A compound of the invention may also be injected directly into the vitreous and aqueous humor.

The compounds and compositions of the invention may also be introduced to the brain, either directly or indirectly. Direct techniques usually involve placement of a drug delivery catheter into the host's ventricular system to bypass the bloodbrain barrier. One such implantable delivery system used for the transport of biological factors to specific anatomical regions of the body is described in U.S. Pat. No. 5,011,472 which is herein incorporated by reference. Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the bloodbrain barrier.

Alternatively, the active ingredient may be in powder form for constitution with a suitable vehicle, e.g., sterile pyrogen-free water, before use. The compounds may also be formulated in rectal compositions such as suppositories or retention enemas, e.g, containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD: 5W) contains VPD diluted 1:1 with a 5% dextrose in water solution. This co-solvent system dissolves hydrophobic compounds well, and itself produces low toxicity upon systemic administration. The proportions of a co-solvent system may be suitably varied without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

It will be appreciated that the actual dosages of the compounds used in the compositions of this invention will vary according to the particular complex being used, the particular composition formulated, the mode of administration and the particular site, host and disease being treated. Optimal dosages for a given set of conditions can be ascertained by those skilled in the art using conventional dosage-determination tests in view of the experimental data for a compound. For oral administration, an exemplary daily dose generally employed is from about 0.001 to about 1000 mg/kg of body weight, more preferably from about 0.001 to about 50 mg/kg body weight, with courses of treatment repeated at appropriate intervals. Administration of prodrugs is typically dosed at weight levels which are chemically equivalent to the weight levels of the fully active form.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

The abbreviations employed throughout the application have the following meaning unless otherwise indicated: Me: methyl; Et: ethyl; Bu: n-butyl; $Bu_4NHSO_4$: tetra-n-butyl ammonium sulfate; Ac: acetyl; Boc: t-butyloxycarbonyl; EtOAc: ethyl acetate; Bn: Benzyl; BnBr: Benzyl bromide; n-BuLi: n-butyl lithium; TFA: trifluoroacetic acid; DCC: dicyclohexylcarbodiimide; rt: room temperature; EDC: [3-(dimethylamino)propyl]-3-ethylcarbodiimide; NMM: 4-methyl morpholine; HCl: Hydrochloric acid; HOBT: 1-hydrobenzatriazole hydrate; HATU: [O-(7-azabenzotriazol-1-yl)-1,1,3,3-tetra-triethyl-uronium hexafluorophsphate; DMAP: N,N-dimethyl-4-aminopyridine; DMF: dimethylformamide; NaOH: sodium hydroxide; KOH: potassium hydroxide; KF: potassium fluoride; Triflate (Tf): trifluoromethanesulfonyl; p-TsOH: para-toluenesulfonic acid; PMBBr: para-methoxy benzyl bromide; DEAD(Dead): diethyl azodicarboxylte; PMP(OH): para-methoxy phenol; CAN: ceric ammonium nitrate; PCC: pyridinium chlorochromate; TMS: trimethylsilyl; TMSO: trimethylsiloxy; PPTS: pyridinium para-toluenesulfonate PyBOP: benzotriazol-1-yloxytris(pyrrolidino)phosphonium hexafluorophosphate; DIEA: diisopropyl ethyl amine.

The preparations of exemplary compounds of the present invention are described in detail in the following schemes and examples, but the artisan will recognize that the chemical reactions described may be readily adapted to prepare a number of other ERAB or HADH2 inhibiting agents of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having applicability for preparing other ERAB or HADH2 inhibiting agents.

EXAMPLES

The present invention will be further illustrated in the following, non-limiting examples.

In the examples described below, unless otherwise indicated all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Dichloromethane ($CH_2Cl_2$) was distilled over calcium hydride under an argon or nitrogen. Tetrahydrofuran (THF) was freshly distilled from sodium/benzophenone. Dimethylformamide (DMF) was stored over molecular sieves. All solvents were purified using standard methods readily known to those skilled in the art, unless otherwise indicated.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F 254 plates and eluted with the appropriate solvent ratios (v/v), and are denoted where appropriate. The reactions were assayed by TLC and terminated as judged by the consumption of starting material.

Melting points (mp) were determined on Melt-TempII capillary apparatus and are uncorrected.

Visualization of the TLC plates was generally done by ultraviolet visualization. Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ prior to filtration and evaporation of the solvents under reduced pressure on a rotary evaporator and noted as solvents removed in vacuo. Products were purified by employing radial chromatography or flash column chromatography (Still et al., *J. Org. Chem.*, 43, 2923 (1978)), the latter using Merck grade flash silica gel (47–61 μm) and a silica gel: crude material ratio of about 20:1 to 100:1 unless otherwise stated.

$^1$H-NMR spectra were recorded on an instrument (Varian OXFORD) operating at 300 or 500 MHz, and $^{13}$C-NMR spectra were recorded operating at 75 MHz. NMR spectra were obtained as $CDCl_3$ solutions (reported in ppm), using chloroform as the reference standard (7.25 ppm and 77.00 ppm) or $CD_3OD$ (3.4 and 4.8 ppm and 49.3 ppm), or internally tetramethylsilane (0.00 ppm) when appropriate. Other NMR solvents were used as needed. When peak multiplicities are reported, the following abbreviations are used: s (singlet), d (doublet), t (triplet), m (multiplet), q (quartet), br (broadened), dd (doublet of doublets), dt (doublet of triplets). Coupling constants, when given, are reported in Hertz (Hz).

Infrared (IR) spectra were recorded on a Perkin-Elmer FT-IR Spectrometer as neat oils, as KBr pellets, or as $CDCl_3$ solutions, and when given are reported in wave numbers ($cm^{-1}$). HPLC spectra were performed on Agilent 1100 series system. Element analyses were obtained from Atlantic Microlabs, Atlanta, Ga., and were within ±0.5% of theoretical values. Silica gel column chromatography was carried out on Merck Silica 60. Mass spectra (MS) were obtained from outside service. The compounds of Formula I may be prepared by general synthetic schemes 1 through 15 given below.

As used herein, "Method A" refers to the general method described in Example 8, "Method B" refers to the general method described in Example 10, "Method C" refers to the general method described in Example 16, and "Method D" refers to the general method described in Example 23.

The ERAB or HADH2 inhibiting agents may be prepared using the reaction routes and synthesis schemes as described below, employing the techniques available to one skilled in the art using starting materials that are readily available or cited in the literature.

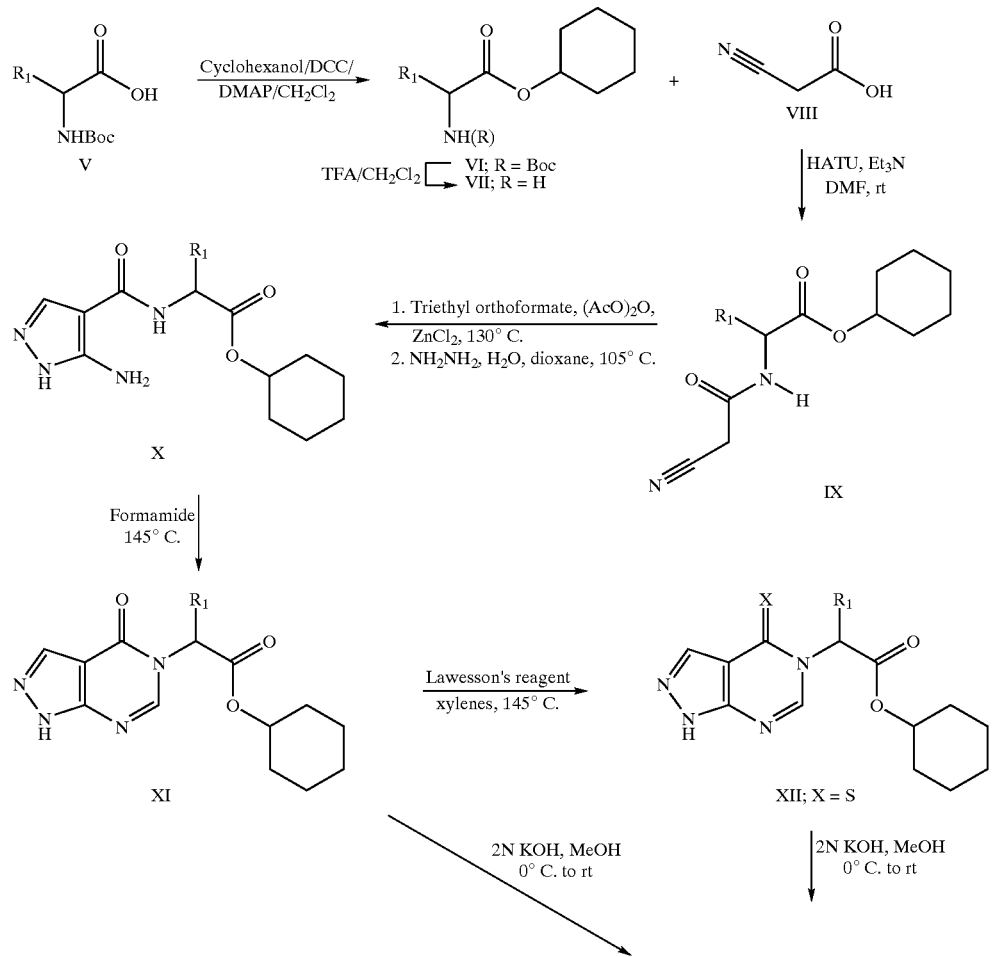

Scheme 1

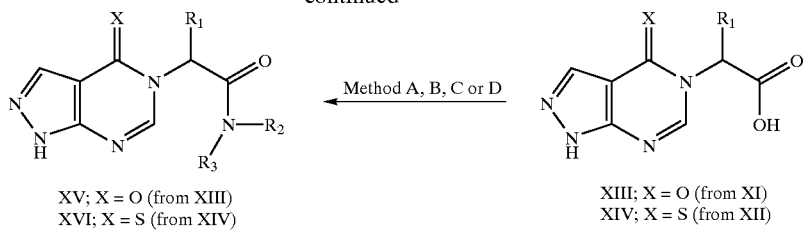

XV; X = O (from XIII)
XVI; X = S (from XIV)

XIII; X = O (from XI)
XIV; X = S (from XII)

Description of Generic Scheme 1 Exemplified by the Conversion of Va ($R_1$=Phenyl) to XVIa (See Examples 1–8):

Boc-L-α-phenylglycine (Va) and cyclohexanol were reacted in dichloromethane in the presence of DCC and catalytic amount of DMAP to give VIa (R=Boc) in almost quantitative yield. Treatment of VIa with trifluoroacetic acid yielded VIIa (R=H, Scheme 1) in 98% yield. VIIa was then coupled to alphacyanoacetic acid (VIII) using HATU as the coupling ERAB OR HADH2 inhibiting agent to afford (2-Cyano-acetylamino)-phenyl-acetic acid cyclohexyl ester (IXa). The reaction of IXa with triethyl orthoformate in acetic anhydride and catalytic anhydrous $ZnCl_2$ at 130° C. gave an intermediate which upon reaction with hydrazine in 1,4-dioxane at 105° C. affords Xa in 51% yield. The [(5-Amino-1H-pyrazole-4-carbonyl)-amino]-phenyl-acetic acid cyclohexyl ester (Xa) was then treated with formamide at 145° C. to give the desired cyclized product (XIa). XIa was treated with Lawesson's reagent under inert gas atmosphere to afford XIIa. Hydrolysis of XIIa afforded the carboxylic acid XIVa, which was then coupled to hexamethyeneimine using the coupling reagent HATU to afford 1-Azepan-1-yl-2-phenyl-2-(4-thioxo-1,4-dihydro-1,4-dihrdropyrazolo[3,4-d]pyrimidin-5-yl)-ethanone (XVIa).

Synthesis of Compounds of the Formula XVII and XVIII as Shown in Scheme 2:

Scheme 2

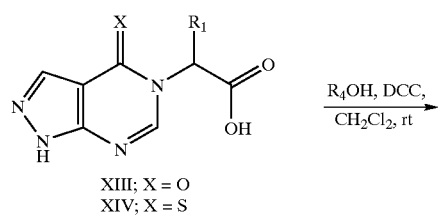

XIII; X = O
XIV; X = S $R_4OH$, DCC,
$CH_2Cl_2$, rt

-continued

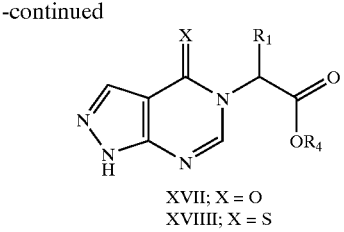

XVII; X = O
XVIII; X = S

Description of Generic Scheme 2:

Compound XIII or XIV was treated with DCC and the appropriate alcohol $R_4OH$ in dichloromethane or an alternate solvent to provide the corresponding esters XVII and XVIII respectively. Other coupling agents familiar to those skilled in the art can also be used to bring about the transformation.

General Notes for Schemes 3 to 13:

The choice of reagents and protecting groups and their manipulations (see "Protective Groups in Organic Chemistry", T. W. Greene and P. G. M Wuts, Wiley-Interscience 1991) are not limited to those described herein and should not be so construed. After each synthetic step an appropriate work-up of the reaction is performed followed by an appropriate purification step as determined by one who is skilled in the art. Although the structures of XIX and XXXVI are shown as single enantiomers, one can also use the racemic mixture (however, in this case the resulting compounds would be racemic too).

Scheme 3

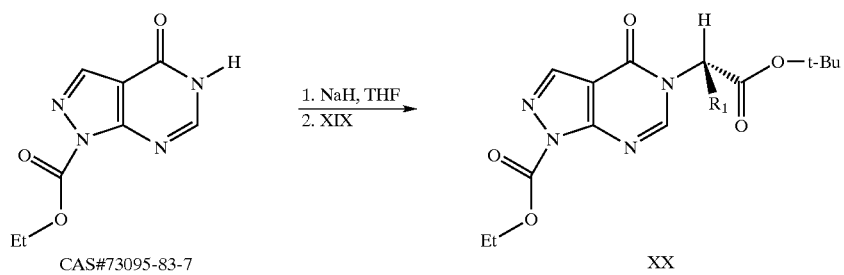

CAS#73095-83-7

1. NaH, THF
2. XIX

XX

TFA, $CH_2Cl_2$

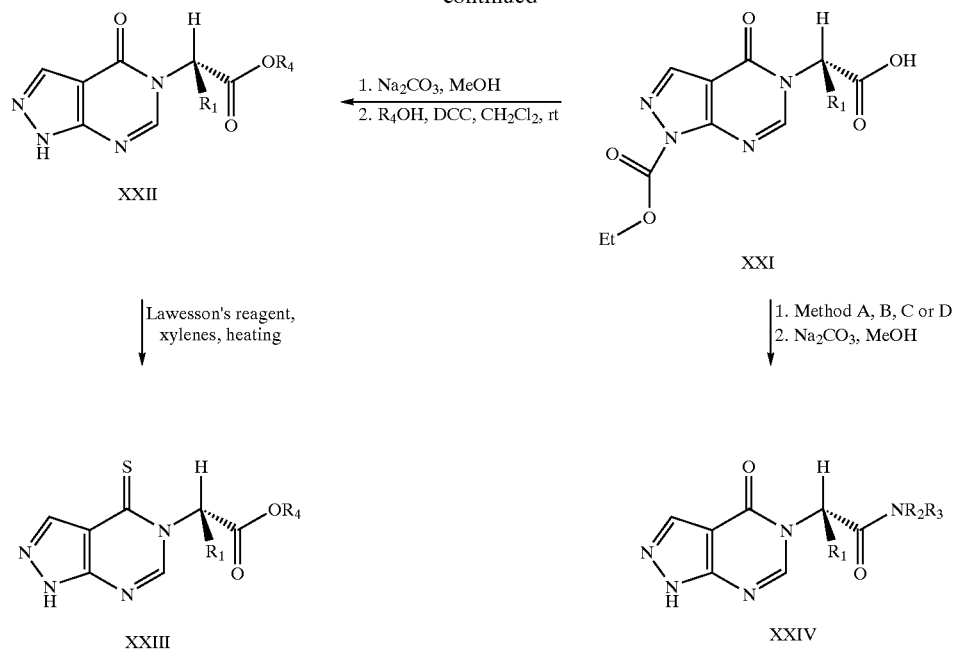

Description of Generic Scheme 3:

4-Oxo-4,5-dihydro-pyrazolo[3,4-d]pyrimidine-1-carboxylic acid ethyl ester (CAS#73095-83-7; Bergmann et al., *J. Chem. Soc.*, 1 (11), 2795–802 (1979)) is treated with an equimolar amount of sodium hydride (NaH) in THF at room temperature and the result stirred for 10 minutes (see Bemis et al., U.S. Pat. No. 5,656,627 for a similar transformation). The resulting mixture is added to the appropriate XIX in THF and stirring continued until the reaction is complete to afford XX after work up. XX is treated with TFA in $CH_2Cl_2$ to give XXI after work up. XXI is then treated with sodium carbonate ($Na_2CO_3$) in methanol (MeOH) under such conditions to minimize racemerization. The intermediate obtained after usual work up is reacted with $R_4OH$ in the presence of DCC or an alternate coupling agent in $CH_2Cl_2$ or an appropriate solvent to afford after work up XXII. Treatment of XXII with Lawesson's reagent in xylenes or an appropriate solvent with heating provides XXIII. XXIV is obtained from XXI via first following methods as described in Examples 8, 10, or 16, followed by treatment of the isolated intermediate with sodium carbonate ($Na_2CO_3$) in methanol (MeOH) (analogous to the procedure described by Secrist et al., *J. Med. Chem.*, 1993, 36(13), 1847–1854 for deprotection of a pyrrole).

Scheme 4

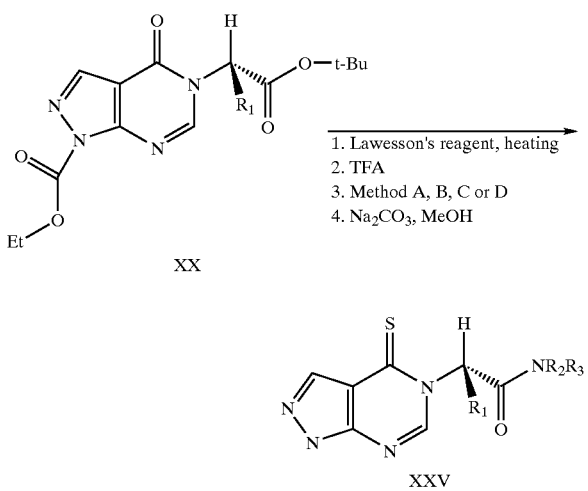

Description of Generic Scheme 4:

XX that is obtained as described in the previous Scheme 3 is first treated with Lawesson's reagent similar to the conversion of XXI to XXIII to give an intermediate, which is treated with TFA in $CH_2Cl_2$ to provide an intermediate acid, which, is converted to the corresponding amide by employing either of the methods described in Examples 8, 10 or 16. This intermediate amide is treated with sodium carbonate ($Na_2CO_3$) in methanol (MeOH) (analogous to the procedure described by Secrist et al., *J. Med. Chem.*, 36(13), 1847–1854 (1993) for deprotection of a pyrrole) to give XXV after the usual work up.

Scheme 5

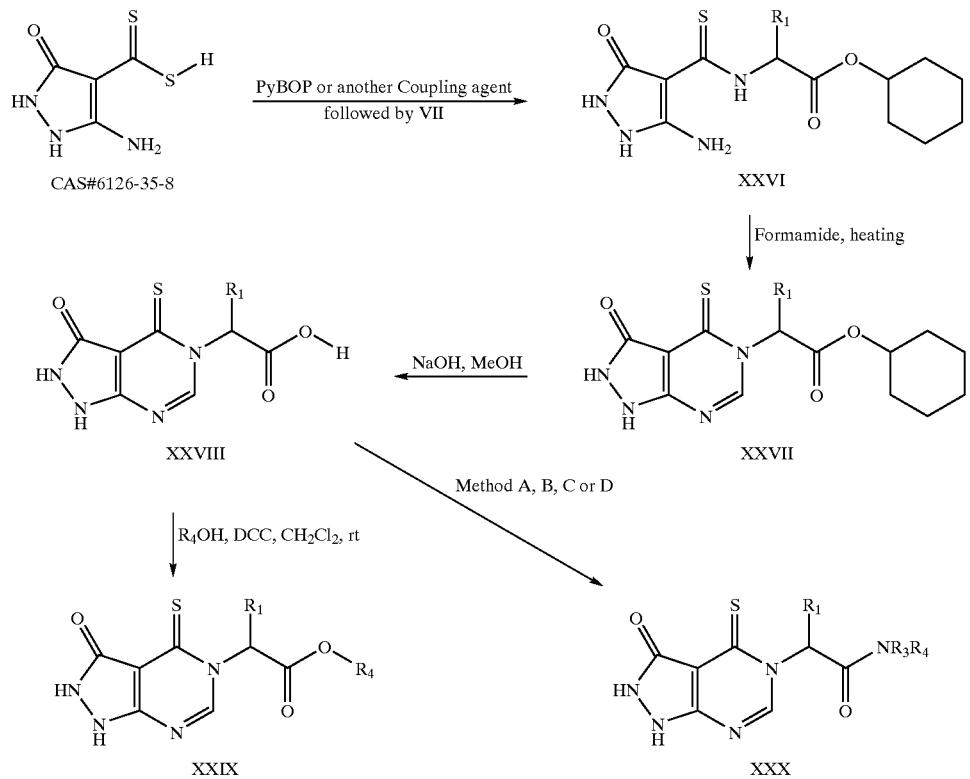

Description of Generic Scheme 5:

5-Amino-3-oxo-2,3-dihydro-1H-pyrazole-4-carbodithioic acid (CAS#6126-35-8; Auzzi et al., *Boll. Chim. Farm.*, 1128, 521–8 (1973)) is treated with Py-BOP, DIEA (Yao et al., *Bioorg. Med. Chem. Lett.*, 8(6), 699–704 (1988)) or another suitable coupling agent in the presence of the appropriate VII to afford XXVI after the appropriate work up. XXVII is treated with formamide while heating the reaction mixture. This provides XXVII after the usual work up. XXVII is the treated with NaOH in MeOH giving XXVIII. XXVIII is then converted to either XXIX or XXX by procedures outlined in Schemes 1–4. Note, that if the appropriate chiral α-amino acid ester VII is utilized to begin with, one trained in the art could manipulate the conditions set forth in Scheme 4 to provide single enantiomers of XXIX and XXX respectively.

Scheme 6

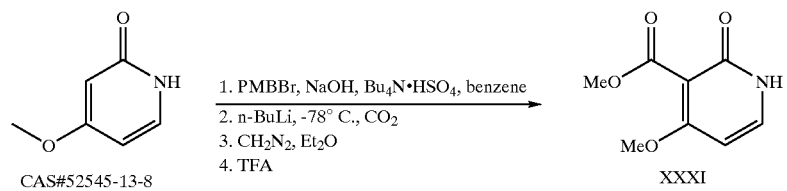

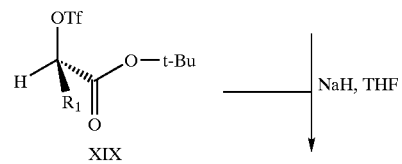

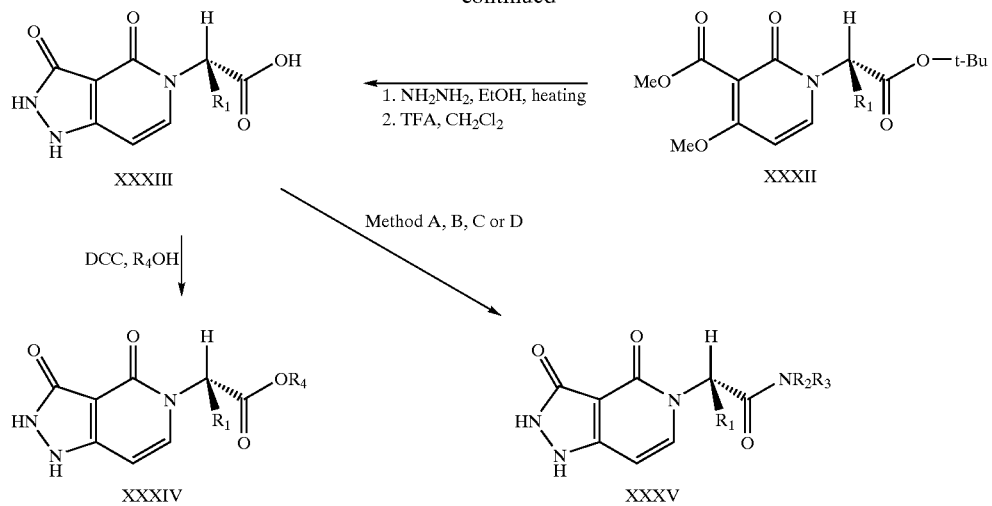

Description of Generic Scheme 6:

4-Methoxy-1H-pyridi-2-one (CAS#52545-13-8; Sieburth et al, *J. Org. Chem.*, 64(3), 950–953 (1999); Walters et al., *Tetrahedron Lett.*, 36(42), 7575–8 (1995); Kuzuya et al., *Nippon Kagaku Kaishi*, 12, 1746–53 (1986))(Bergmann, R. et al., *J. Med. Chem.*, 33, 492–504 (1990)) is alkylated under phase transfer conditions (Zwierzak, *Synthesis*, 527, 529 (1979)) with benzyl bromide to afford the N-alkylated intermediate or by the conditions of Yamawaki, *Chem. Lett.*, 1143–1146 (1981) using KF-alumina and benzylbromide. This intermediate is converted to its 3-carboxylic acid derivative according to the procedure of Pattenden et al, *J. Chem. Soc.*, Perkin Trans. 1(1), 67–77 (1992). The intermediate 3-carboxylic acid is converted to its methyl ester via treatment with diazomethane. The intermediate methyl ester is treated with TFA to give XXXI. XXXI is converted to XXXII using the appropriate XIX and adapting the procedure outlined in Scheme 3 for the conversion of CAS#73095-83-7 to XX. XXXII is treated with hydrazine in ethanol with heating to provide the fused bicyclic intermediate. This intermediate is converted to the corresponding carboxylic acid XXXIII via treatment with TFA. XXXIII is then converted to either XXXIV or XXXV by procedures outlined in Schemes 1–5.

Scheme 7

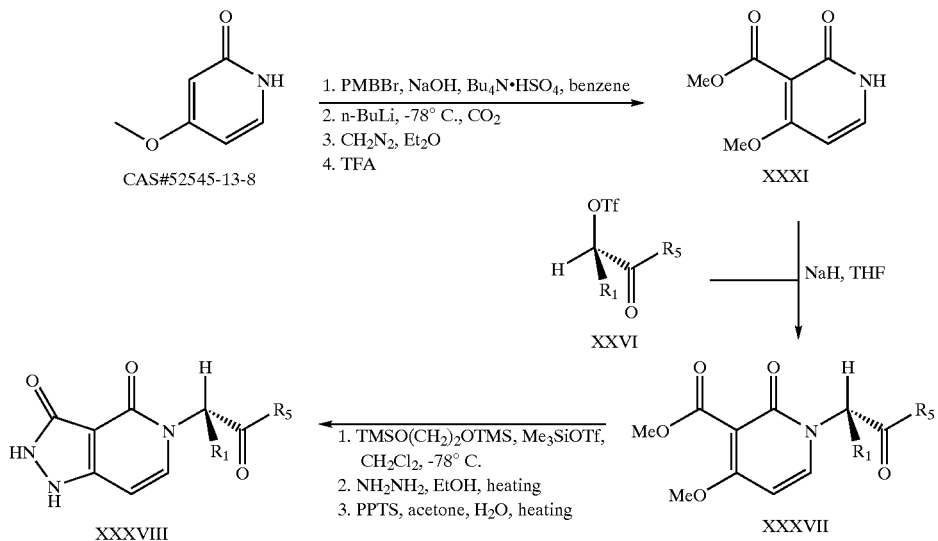

Description of Generic Scheme 7:

XXXI (described previously in Scheme 6) is converted to XXXVII via the procedure outlined in Scheme 3 for the conversion of 4-Oxo-4,5-dihydropyrazolo[3,4-d]pyrimidine-1-carboxylic acid ethyl ester (CAS#73095-83-7; Bergmann et al., *J. Chem. Soc.*, 1 (11), 2795–802 (1979)) to XX. The ketone functionality in XXXVII is protected via the 1,3-Dioxolane as per the conditions of Hwu, et al., *J. Org. Chem.*, 1987, 52, 188. This intermediate is reacted with hydrazine in ethanol with heating to give the 3-oxo-pyrrolozo intermediate, which is subsequently treated with pyridinium p-toluenesulfonate (Hagiwara et al, *J. Chem. Soc.*, Chem. Commun., 1987, 1351) to provide XXXVIII.

Scheme 8

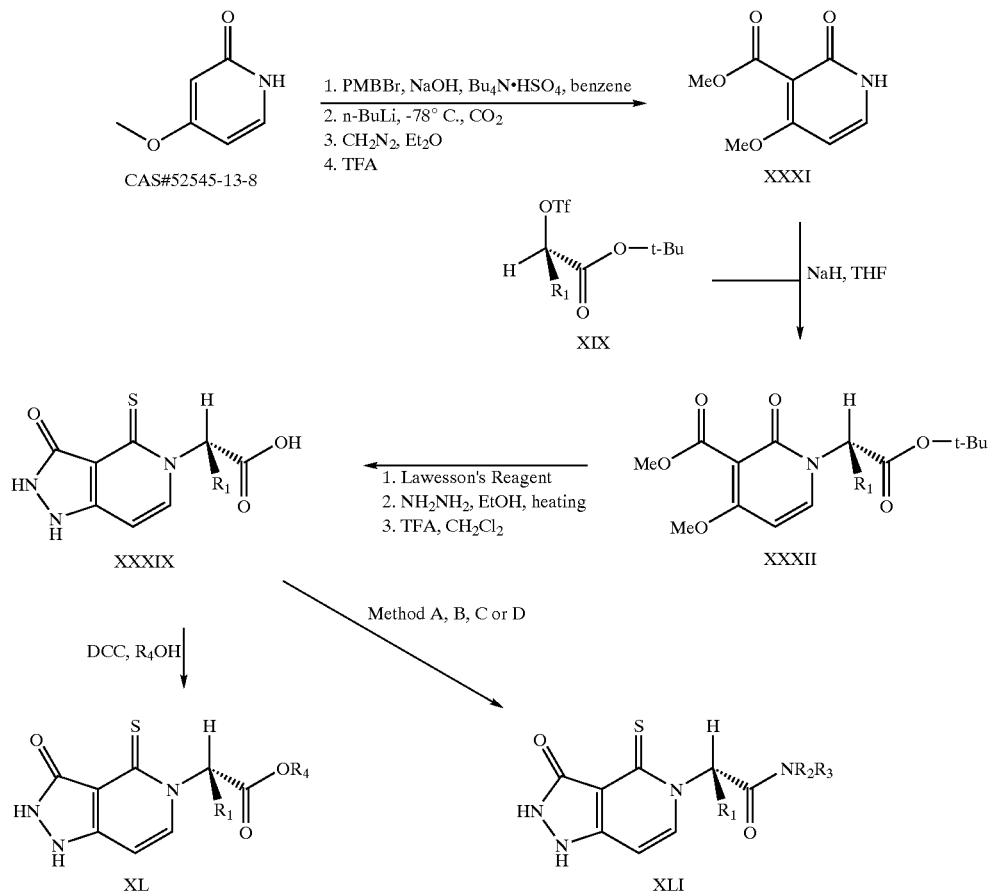

Description of Generic Scheme 8:

XXXII (previously described in Scheme 6) is treated with Lawesson's reagent as previously described, followed by treatment with hydrazine in ethanol with heating to provide the fused bicyclic intermediate. This intermediate is converted to the corresponding carboxylic acid XXXIX via treatment with TFA. XXXIX is then converted to either XL or XLI by procedures outlined in Schemes 1–7.

Scheme 9

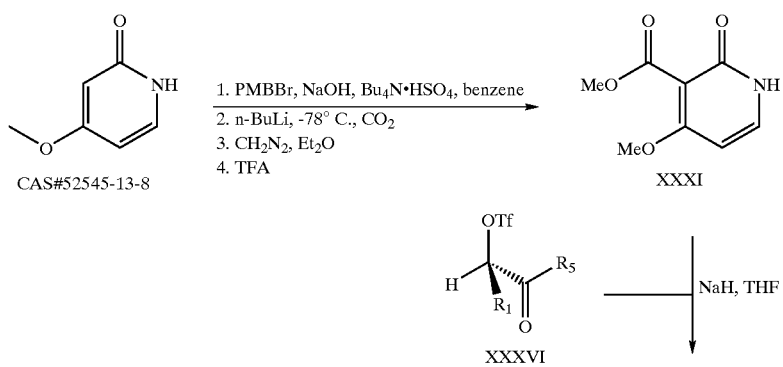

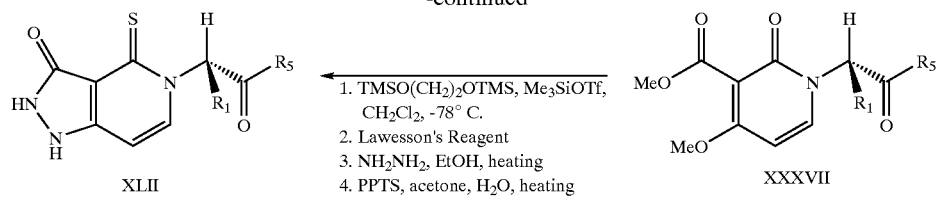

Description of Generic Scheme 9:

The ketone functionality in XXXVII (previously described in Scheme 7) is protected via the 1,3-Dioxolane as per the conditions of Hwu et al., *J. Org. Chem.*, 52, 188 (1987). This intermediate is treated with Lawesson's reagent under conditions previously described for similar conversions to give the corresponding thioamide intermediate. This intermediate is reacted with hydrazine in ethanol with heating to give the 3-oxo-pyrolozo intermediate which is subsequently treated with pyridinium p-toluenesulfonate (Hagiwara et al., *J. Chem. Soc.*, Chem. Commun., 1351 (1987)) to provide XLII.

(1979)) with benzyl bromide to afford the N-alkylated intermediate or by the conditions of Yamawaki, *Chem. Lett.*, 1143–1146 (1981) using KF-alumina and benzylbromide. This intermediate is converted to its 3-methanol derivative adapting the procedure of Padeniten et al, *J. Chem. Soc., Perkin Trans.* 1(1), 67–77 (1992) and trapping the lithiated intermediate with para-formaldehyde under cracking conditions. The alcoholic functionality in this intermediate is protected via conversion to benzyl ether via alkylation of the alcohol using NaH and benzyl bromide. The intermediate benzyl ether is treated with TFA to give XLIII. XLIII is N-alkylated with the appropriate XIX using NaH, followed

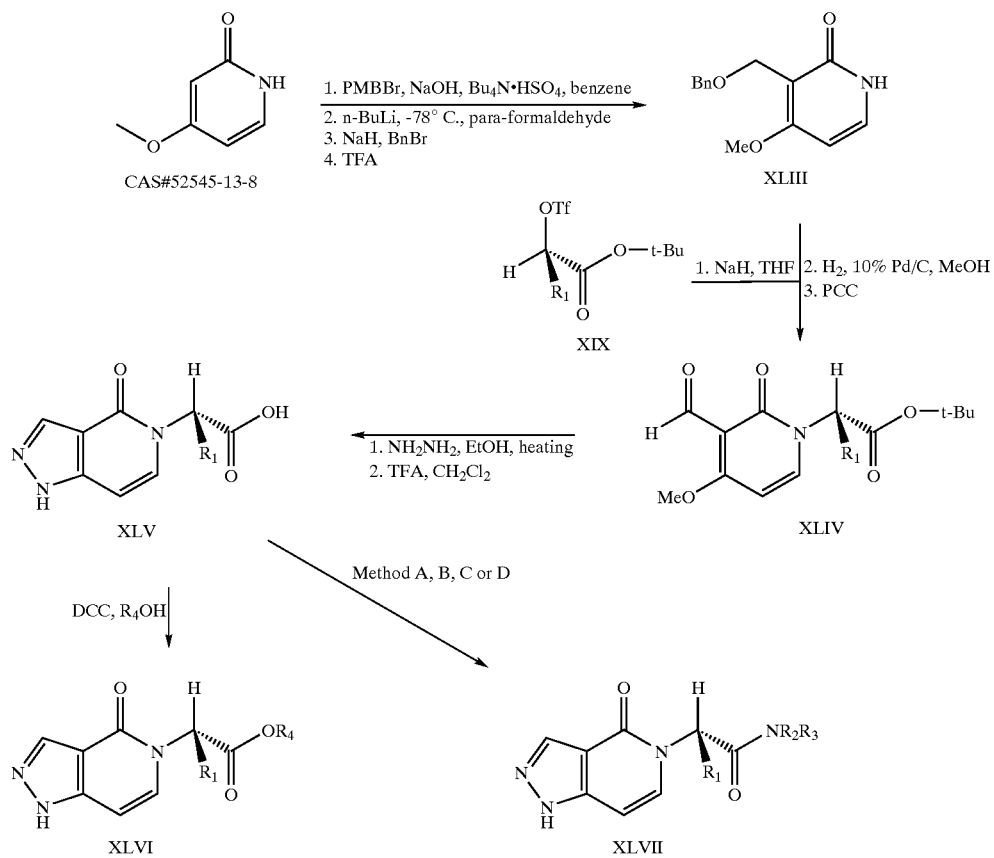

Scheme 10

Description of Generic Scheme 10:

4-Methoxy-1H-pyridi-2-one (CAS#52545-13-8; Sieburth et al, *J. Org. Chem.*, 64(3), 950–953 (1999); Walters et al., *Tetrahedron Lett.*, 36(42), 7575–8 (1995); Kuzuya et al., *Nippon Kagaku Kaishi*, 12, 1746–53 (1986))(Bergmann, R. et al.,*J. Med. Chem.*, 33, 492–504 (1990)) is alkylated under phase transfer conditions (Zwierzak, *Synthesis*, 527, 529 (1979)) with benzyl bromide to afford the N-alkylated intermediate or by the conditions of Yamawaki, *Chem. Lett.*, 1143–1146 (1981) using KF-alumina and benzylbromide.

by hydrogenolysis and PCC oxidation to yield XLIV. XLIV is treated with hydrazine in ethanol with heating to provide the fused bicyclic intermediate. This intermediate is converted to the corresponding carboxylic acid XLV via treatment with TFA. XLV is then converted to either XLVI or XLVII by procedures outlined in previous schemes for similar conversions.

Scheme 11

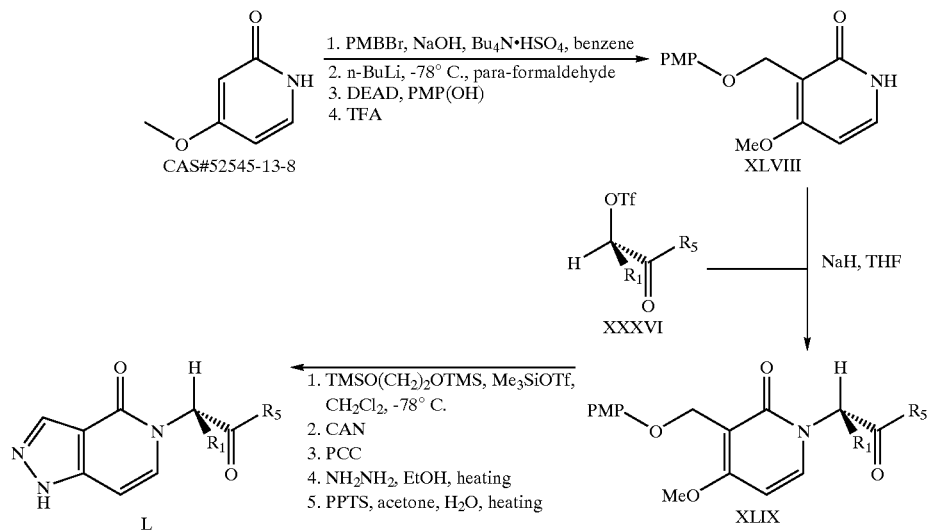

Description of General Scheme 11:

4-Methoxy-1H-pyridi-2-one (CAS#52545-13-8; Sieburth et al, *J. Org. Chem.*, 64(3), 950–953 (1999); Walters et al., *Tetrahedron Lett.*, 36(42), 7575–8 (1995); Kuzuya et al., *Nippon Kagaku Kaishi*, 12, 1746–53 (1986))(Bergmann et al., *J. Med. Chem.*, 33, 492–504(1990)) is alkylated under phase transfer conditions (Zwierzak, A., *Synthesis*, 527, 529 (1979)) with benzyl bromide to afford the N-alkylated intermediate or by the conditions of Yamawaki, *Chem. Lett.*, 1143–1146 (1981) using KF-alumina and benzylbromide. This intermediate is converted to its 3-methanol derivative adapting the procedure of Padentten et al. *J. Chem. Soc.*, Perkin Trans. 1(1), 67–77 (1992) and trapping the lithiated intermediate with para-formaldehyde under cracking conditions. The alcoholic functionality in this intermediate is protected as the para-methoxyphenyl ether via a Mitsunobu reaction as described in Fukuyama et al., *Tetrahedron Letters*, 26, 6291 (1985) or Petitou et al., *Tetrahedron Letters*, 29, 1389 (1988) for a similar protection of a primary alcohol. The intermediate para-methoxyphenyl ether derivative is treated with TFA to give XLVIII. XLVIII is converted to XLIX using the appropriate XXXVI and adapting the procedure outlined in Scheme 7 for the conversion of XXXI to XXXVII. The ketone functionality in XLIX is protected via the 1,3-Dioxolane as per the condition of Hwu et al., *J. Org. Chem.*, 52, 188 (1987). This is followed by treatment with CAN (Fukuyama et al., *Tetrahedron Letters*, 26, 6291 (1985)) to afford the deprotected alcohol intermediate, which is oxidized to the corresponding aldehyde intermediate using PCC. This intermediate is reacted with hydrazine in ethanol with heating to give the 3-oxo-pyrolozo intermediate which is subsequently treated with pyridinium p-toluenesulfonate to provide L.

Scheme 12

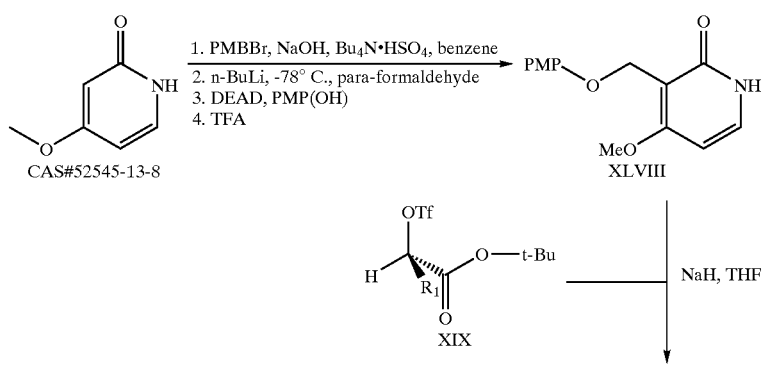

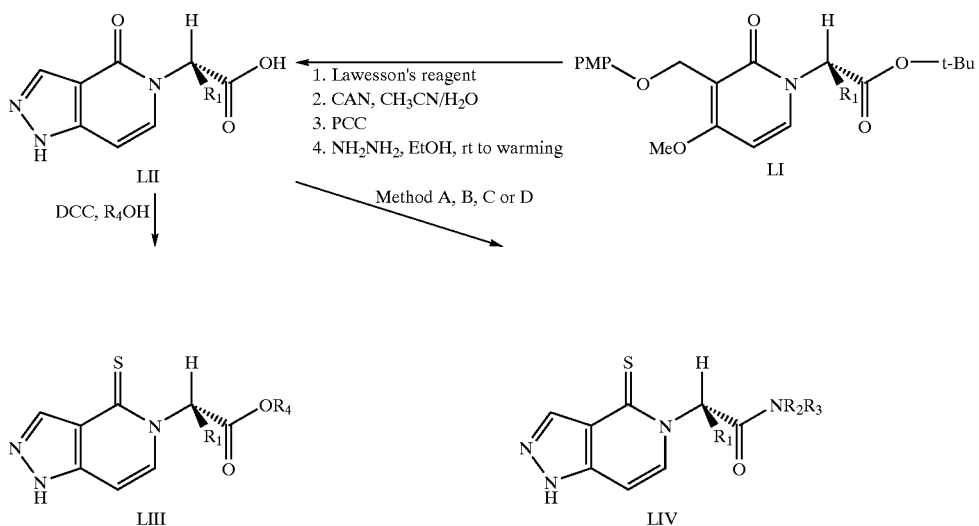

Description of Generic Scheme 12:

XLVIII (previously described in Scheme 11) is converted to LI using the appropriate XIX and adapting the procedure outlined in Scheme 6 for the conversion of XXXI to XXXII. LI is treated with Lawesson's reagent as previously described in earlier schemes, followed by treatment with CAN (Fukuyama et al, *Tetrahedron Letters*, 26, 6291 (1985)) to afford the deprotected alcohol intermediate which is oxidized to the corresponding aldehyde intermediate using PCC. The aldehyde intermediate is treated with hydrazine in ethanol with heating to provide the fused bicyclic intermediate. This bicyclic intermediate is converted to the corresponding carboxylic acid LII via treatment with TFA. LII is then converted to either LIII or LIV by procedures outlined in Schemes 1–11 for similar conversions.

Description of Generic Scheme 13:

The ketone functionality in XLIX (previously described in Scheme 11) is protected via the 1,3-Dioxolane as per the conditions of Hwu et al, *J. Org. Chem.*, 52, 188 (1987), followed by treatment with Lawesson's reagent to give the corresponding thioamide intermediate. The thioamide intermediate is treated with CAN (Fukayama et al., *Tetrahedron Letters*, 26, 6291 (1985)) to afford the deprotected alcohol intermediate which is oxidized to the corresponding aldehyde intermediate using PCC. This intermediate is reacted with hydrazine in ethanol with heating to give the bicyclic intermediate which is subsequently treated with pyridinium p-toluenesulfonate to provide LV.

Scheme 13

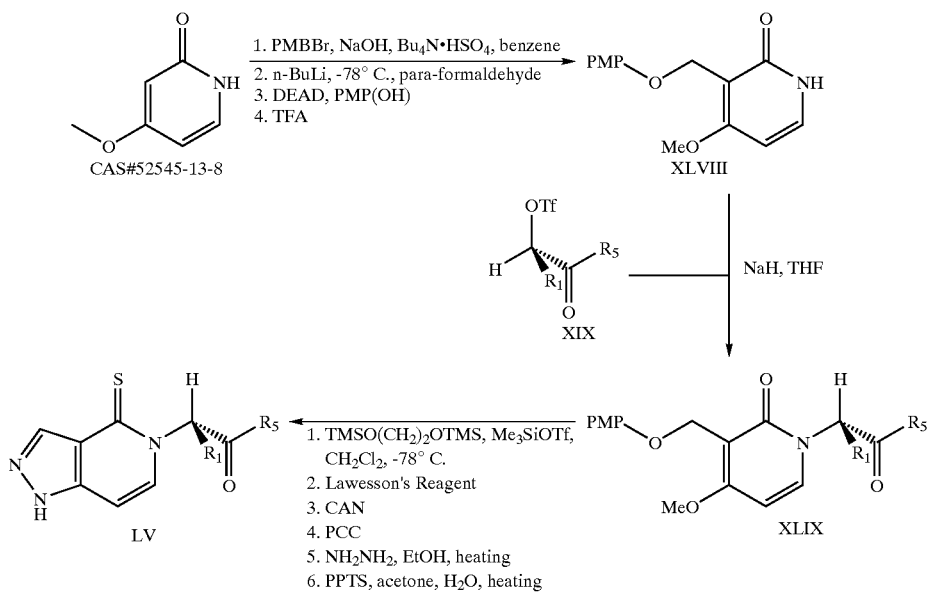

Scheme 14

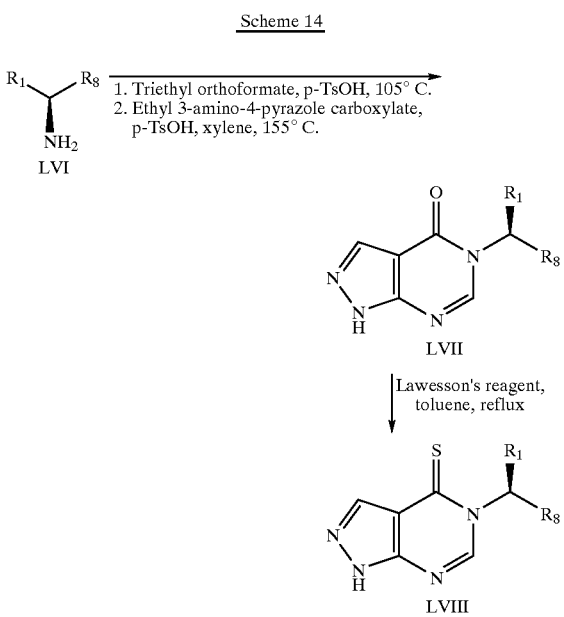

Description of Generic Scheme 14 Exemplified by the Conversion of LVIa (R$_1$=Phenyl and R$_8$=Methyl) to LVIIIa (See Examples 32 & 33):

A mixture of LVI and (R)-α-methyl benzylamine is added p-TsOH and the result refluxed for 4 hours. After the appropriate work up the crude intermediate is taken up in xylene and to it added Ethyl 3-amino-4-pyrazole, p-TsOH and the result refluxed for 24 hours. After the appropriate work up, LVII is obtained as a white solid. LVII is then treated with Lawesson's reagent in toluene at reflux to yield LVIII. Although, LVI is shown in the generic Scheme 14 as chiral, one could use it as a racemic mixture, however the resulting products would also be racemic.

Description of Generic Scheme 15 (an Alternate Route to LVII and LVIII):

4-Oxo-4,5-dihydro-pyrazolo[3,4-d]pyrimidine-1-carboxylic acid ethyl ester (CAS#73095-83-7; Bergmann et al., *J. Chem. Soc.*, 1 (11), 2795–802 (1979)) is N-alkylated with the appropriate LIX using NaH as described in previous schemes to give LX. LX is then treated with Na$_2$CO$_3$ in MeOH to give LVII which is treated with Lawesson's reagent to give LVIII. Although, LIX is shown as a chiral compound, one could use it as a racemic mixture, however the resulting products would also be racemic Preparation of Intermediates and Starting Materials as Required for Various Schemes and Examples α-Amino acids are commercially available, or can be prepared according to methods familiar to those skilled in the art. For a recent review on synthesis of optically active α-amino acids see O'Donnell, *Aldrichimica Acta*, 34, 1, 3–15 (2001) and references cited therein. Intermediates represented by the general structure XIX (racemic and optically active) can be prepared from the corresponding α-hydroxy t-butyl esters via conversion of the hydroxyl to the triflate according to methods familiar to those skilled in the art. Listed below are selected reviews on α-hydroxy esters: Ladduwahetty, *Contemp. Org. Synth.*, 4(4), 309–325 (1997); and Sharpless, *Chemtracts: Org. Chem.*, 2(4), 255–7 (1989).

Similarly, intermediates represented by the general structure XXXVI (racemic and optically active) can be prepared from the corresponding α-hydroxy ketones via conversion of the hydroxyl to the triflate according to methods familiar to those skilled in the art. Listed below are selected reviews on α-hydroxy ketones: Schultz et al., *Stereosel. React. Met.-Act. Mol., Proc. Symp.*, 2$^{nd}$ (1995), Meeting Date 1994, 45–48. Publisher: Vieweg, Wiesbaden, Germany; Roush, *Chemtracts: Org. Chem.*, 1(5), 385–7 (1988); and Ganem, *Chemtracts: Org. Chem*, 1(5), 413–14 (1988).

Chiral or racemic amines such as LVI are obtained commercially or can be prepared by those skilled in the art via methods disclosed in the literature or by applying procedures disclosed in the literature.

Scheme 15

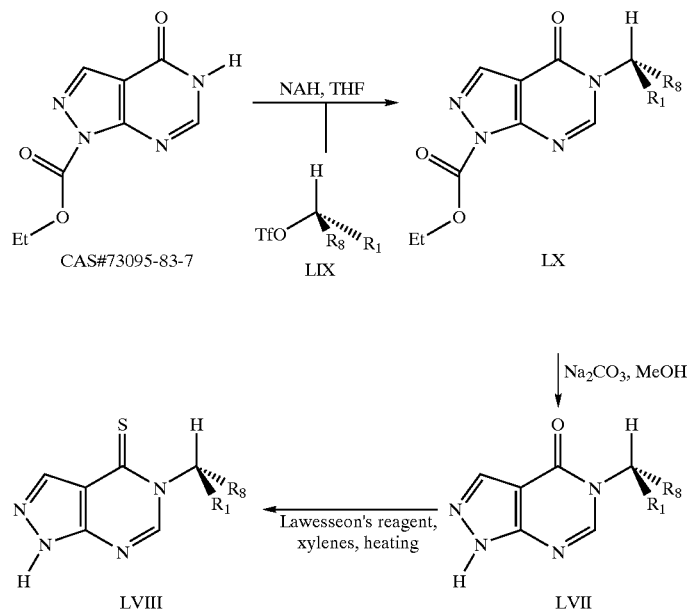

Chiral or racemic triflates such as LIX are prepared by one skilled in the art from the corresponding alcohols via conversion to the triflates by methods disclosed in the literature or by applying procedures disclosed in the literature.

Synthesis of Intermediate VIIb ($R_1$=3-allyloxy-phenyl)

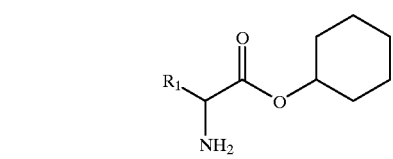

VIIb (1) (3-Allyloxy-phenyl)-acetic acid (B).

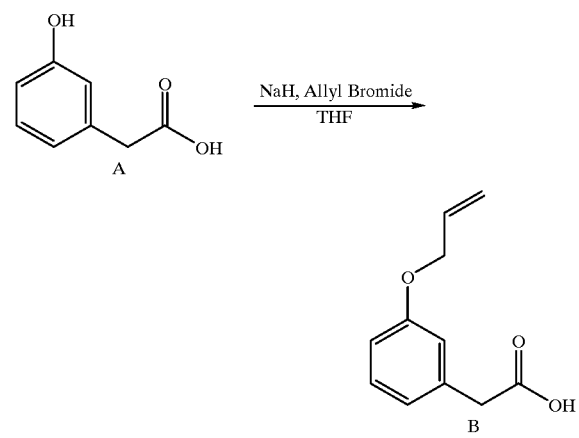

A solution of 3-hydroxyphenylacetic acid (A) (10 g, 65.72 mmol) in 300 ml of dry THF was added to a mixture of NaH (6.0 g, 197.2 mmol) with 100 ml of dry THF. The resulting mixture was stirred at room temperature under Ar for 2 hours, then allyl bromide (23 ml, 262.88 mmol) was added dropwise. The resulting mixture was refluxed overnight at 67° C. After cooling down in an ice bath, the reaction mixture was quenched by adding ice water (100 ml) and stirred at room temperature for 2 hours, then evaporated by vacuum to remove most of THF. The residue was extracted with ether (200 ml) to remove the neutral species. The aqueous phase was acidified by adding 2N HCl solution to pH 4.0, and extracted with $CH_2Cl_2$ (2×250 ml). The combined organic layers was washed with brine (100 ml), dried over $Na_2SO_4$ and evaporated by vacuum to afford (B) (5.1 g, 26.29 mmol, 40% yield) as an off-white grease.

TLC; $R_f$=0.3 ($H_2Cl_2$:MeOH=9:1).

$^1$H-NMR (CDCl$_3$): δ 3.65 (s, 2H), 4.54–4.57 (d, J=8 Hz, 2H), 5.29–5.34 (d, J=15 Hz, 1H), 5.41–5.48 (d, J=20 Hz, 1H), 6.01–6.14 (m, 1H), 6.76–6.92 (m, 3H), 7.19–7.27 (m, 1H).

IR(CDCl$_3$) 2921, 1697, 1596, 1494, 1445, 1438, 1272, 1217, 1176, 1924, 923, 774 cm$^{-1}$

MS Calcd for $C_{11}H_{12}O_3$ (M+H)=193, observed (M+H)=193;

HPLC: 5% $CH_3CN/H_2O$ (0.1% TFA) to 90% $CH_3CN/H_2O$ (0.1% TFA)/10 min.

Retention time=6.807 min.

(2) (3-Allyloxy-phenyl)-acetic acid cyclohexyl ester (C).

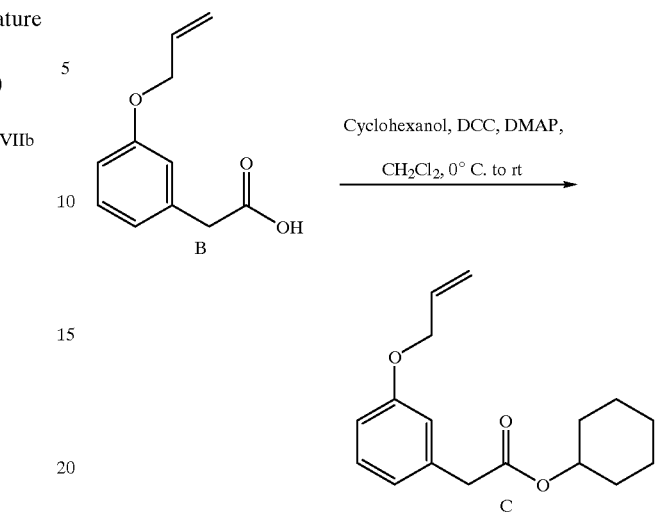

To a solution of (B) (5.05 g, 26.3 mmol) and cyclohexanol (3.3 ml, 31.56 mmol) in 25 ml of $CH_2Cl_2$ at 0° C. was added DCC (dicylchexylcarbodiimide)(6.0 g, 28.93 mmol) and DMAP (N,N-dimethyl-4-aminopyridine) (0.32 g, 2.63 mmol). The resulting mixture was stirred at 0° C. to room temperature for 2 days. The reaction mixture was filtered off and washed well with $CH_2Cl_2$ to remove most of the N,N-dicyclohexylurea. The filtrate was extracted with saturated $NaHCO_3$, brine (2×100 ml). The organic layer was dried over $Na_2SO_4$ and evaporated by vacuum. The residue was purified by flash silica gel chromatography, eluted with hexanes:EtOAc (2:1) to afford (C) (7.05 g, 25.6 mmol, 98% yield) as a clear oil.

TLC: $R_f$=0.8 (Hexanes:EtOAc=2:1).

$^1$H-NMR (CDCl$_3$): δ 1.26–1.94 (m, 10H), 4.55–4.59 (d, J=13 Hz, 2H), 4.77–4.83 (m, 1H), 5.28–5.34 (d, J=14 Hz, 1H), 5.41–5.48 (d, J=14 Hz, 1H), 6.02–6.15 (m, 1H), 6.83–6.98 (m, 3H), 7.22–7.28 (m, 1H).

IR(CDCl$_3$) 2935, 2858, 2359, 2118, 1731, 1599, 1489, 1259, 1151, 1038, 1016, 927, 770, 689 cm$^{-1}$

MS Calcd for $C_{17}H_{22}O_3$ (M+H)=275, observed (M+H)=275;

HPLC: 50% $CH_3CN/H_2O$ (0.1% TFA) to 90% $CH_3CN/H_2O$ (0.1% TFA)/10 min.

Retention time=7.64 min.

(3) (3-Allyloxy-phenyl)-2-azido-acetic acid cyclohexyl ester (D).

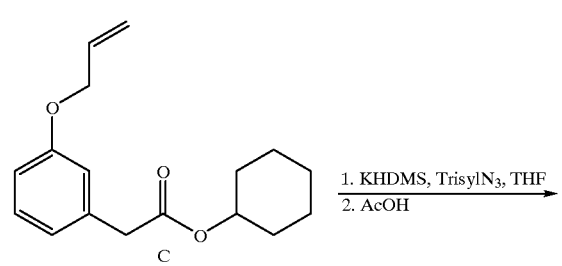

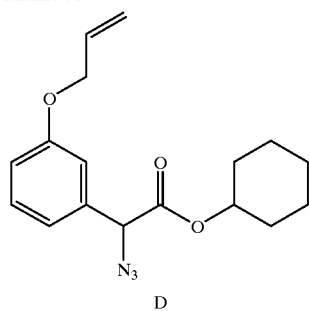

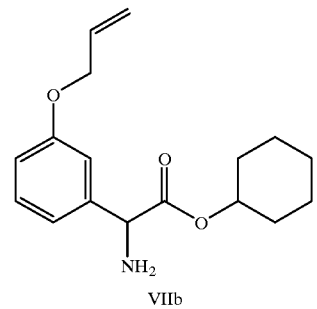

To a solution of potassium bis(trimethylsilyl)amide (KHMDS) 0.5M in toluene (61.4 ml, 30.72 mmol) in 50 ml of dry THF stirred at −78° C. under Ar was added via syringe a precooled (−78° C.) solution of(C) (7.02 g, 25.6 mmol) in 75 ml of dry THF. The resulting yellow solution was stirred at −78° C. for 30 min, and then another precooled (−78° C.) solution of 2,4,6-triiosopropylbenzene-sulfonylazide (9.51 g, 30.72 mmol) in 75 ml of dry THF was added via syringe. The reaction mixture was stirred at −78° C. for 3 hours and then quenched with HOAc (7.3 ml, 128 mmol). The resulting mixture was stirred overnight at −78° C. to room temperature under Ar. 1N aqueous NH₄Cl (100 ml) was added to this yellow suspension, then extracted with EtOAc (2×300 ml). The organic layer was washed with brine, dried over Na₂SO₄ and evaporated by vacuum. The residue was suspended in 300 ml of acetone, NaI (19.1 g, 128 mmol) and NaOAc (6.3 g, 76.8 mmol), and then stirred at room temperature for 3 hours. Inorganic salt was removed by filtration. The filtrate was evaporated and then partitioned between EtOAc (2×300 ml) and water (75 ml). The combined organic layers were washed with 0.5 M NaHSO₃, brine (2×50 ml), dried over Na₂SO₄ and evaporated by vacuum. The residue was purified by flash chromatography, eluted with hexanes:EtOAc (6:1) to afford (1) (7.7 g, 24.32 mmol, 95% yield) as a brown color oil. TLC: $R_f$=0.8 (Hexanes:EtOAc (6:1).

¹H-NMR (CDCl₃): δ 1.26–1.87 (m, 10H), 4.57–4.64 (m, 2H), 4.90–4.94 (m, 2H), 5.31–5.36 (d, J=14 Hz, 1H), 5.42–5.49 (d, J=20 Hz, 1H), 6.02–6.15 (m, 1H), 6.94–7.18 (m, 3H), 7.31–7.59 (m, 1H).

IR(CDCl₃) 2936, 2859, 2359, 2104, 1736, 1598, 1498, 1448 cm⁻¹

MS Calcd for $C_{17}H_{21}N_3O_3$ (M+H)=316 and (M+H−N₂)= 288, observed (M+H−N₂)=288;

HPLC: 50% CH₃CN/H₂O (0.1% TFA) to 90% CH₃CN/ H₂O (0.1% TFA)/10 min.

Retention time=8.25 min.

(4) (3-Allyloxy-phenyl)-2-amino-acetic acid cyclohexyl ester (VIIb)

The solution of (D)(4.34 g, 13.8 mmol) in 40 ml of THF and 80 ml of MeOH was treated with ammonium chloride (5.2 g, 96.6 mmol) and Zn powder (2.71 g, 41.4 mmol) with vigorous stirring overnight at room temperature. The insoluble salt was filtered off and washed well with MeOH. The filtrate was evaporated under vacuum. The residue was partitioned between EtOAc (200 ml) and water, brine (2×100 ml). The organic layer was dried over Na₂SO₄, then evaporated by vacuum. The residue of yellow oil was purified by flash silica gel chromatography, eluted with hexanes:EtOAc (1:1) to remove the front fraction, then eluted with CH₂Cl₂:EtOAc (1:1) to afford (VIIb) (2.12 g, 7.31 mmol, 53% yield) as a yellow oil.

TLC: $R_f$=0.3 (Hexanes:EtOAc=1:1).

¹H-NMR (CDCl₃): δ 1.24–1.83 (m, 10H), 2.31 (s, br, 2H, NH), 4.55–4.47 (d, J=3 Hz, 2H), 4.66 (s, 1H), 4.79–4.85 (m, 1H), 5.29–5.30 (d, J=10 Hz, 1H), 5.395.47 (d, J=20 Hz, 1H), 6.02–6.14 (m, 1H), 6.86–6.98 (m, 3H), 7.25–7.30 (m, 1H).

IR(CDCl₃) 2936, 2858, 2359, 1728, 1599, 1487, 1449, 1260, 1070, 1012, 927, 782 cm⁻¹

MS Calcd for $C_{17}H_{23}NO_3$ (M+H)=290, observed (M+H)=290;

HPLC: 5% CH₃CN/H₂O (0.1% TFA) to 90% CH₃CN/ H₂O (0.1% TFA)/10 min.

Retention time=6.81 min.

Synthesis of 1-Benzyl-4-butyl-piperidin-4-ol (F).

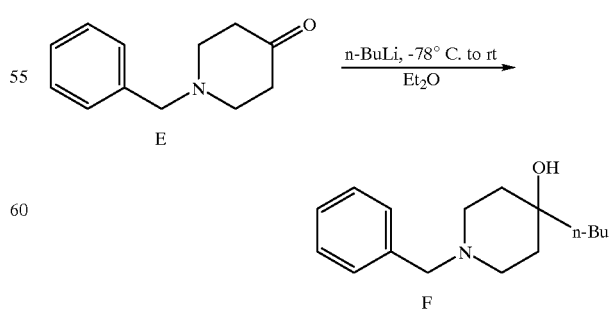

The solution of 1-benzyl-4-piperidone (E) (0.5 ml, 2.7 mmol) in 2 ml of ethyl ether at −78° C. under Ar was added to 2.5M butyl lithium in hexane (2.2 ml, 5.4 mmol). The resulting mixture was stirred overnight at −78° C. to room temperature. The reaction mixture was partitioned between ether (200 ml) and water (20 ml). The aqueous layer was extracted again with ether (100 ml) and EtOAc (100 ml). The combined organic layer was dried over anhydrous Na$_2$SO$_4$, then concentrated by vacuum. The residue was purified by flash silica gel chromatography and eluted with hexanes:EtOAc (1:1) to afford (F) (0.56 g, 2.25 mmol, 83% yield) as a brown color oil.

TLC; R$_f$=0.4 (EtOAc).

$^1$H-NMR; (CDCl$_3$) δ 0.92–0.96 (tri, 3H)), 1.14–1.74 (m, 10H), 2.32–2.41 (m, 2H), 2.63–2.68 (m, 2H), 3.55 (s, 2H), 7.30–7.37 (m, 5H).

IR(CDCl$_3$) 3395, 2932, 2812, 2359, 1494, 1467, 1365, 1342, 1299, 1255, 1162, 1105, 1029, 971, 905, 808 cm$^{-1}$

MS Calcd for C$_{16}$H$_{25}$NO (M+H)=248, observed (M+H)=248;

HPLC: 5% CH$_3$CN/H$_2$O (0.1% TFA) to 90% CH$_3$CN/H$_2$O (0.1% TFA)/10 min.

Retention time=5.29 min.

Synthesis of 1-Benzyl-4-Methyl-piperidin-4-ol (G).

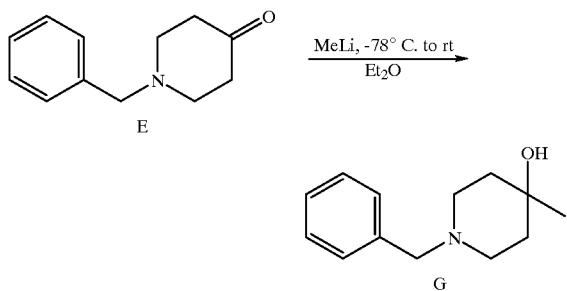

A solution of 1-benzyl-4-piperidone (E) (0.5 ml, 2.7 mmol) in 2 ml of ethyl ether at −78° C. under Ar was added to 1.0M methyl lithium in THF (5.4 ml, 5.4 mmol). The resulting mixture was stirred overnight at −78° C. to room temperature. The reaction mixture was partitioned between ether (200 ml) and water (20 ml). The aqueous layer was extracted again with ether (100 ml) and EtOAc (100 ml). The combined organic layer was dried over anhydrous Na$_2$SO$_4$, then concentrated by vacuum. The residue was purified by flash silica gel chromatography and eluted with hexanes:EtOAc (1:1) to afford (G) (0.22 g, 1.08 mmol, 40% yield) as a yellow oil.

TLC; R$_f$=0.5 (EtOAc).

$^1$H-NMR; (CDCl$_3$) δ 1.27 (s, 3H)), 1.59–1.76 (m, 4H), 2.36–2.82 (m, 4H), 5.58 (s, br, 1H), 7.30–7.45 (m, 5H).

IR(CDCl$_3$) 3340, 2917, 2359, 1712, 1593, 1453, 700 cm$^{-1}$

MS Calcd for C$_{13}$H$_{19}$NO (M+H)=206, observed (M+H)=206;

HPLC: 5% CH$_3$CN/H$_2$O (0.1% TFA) to 90% CH$_3$CN/H$_2$O (0.1% TFA)/10 min.

Retention time=4.35 min.

Synthesis of 4-Butyl-piperidin-4-ol (H).

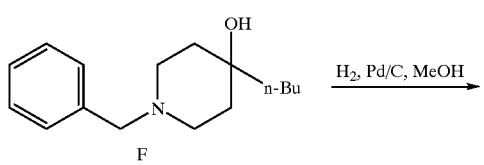

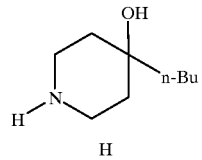

A reaction mixture of 1-benzyl-4-butyl-piperidin-4-ol (F) (83 mg, 0.34 mmol) and 10% Pd—C (10 mg) in 10 ml of MeOH was vigorously shaken under H$_2$ (40 psi) for overnight. The mixture was filtered off through celite and washed well with MeOH. The filtrate was evaporated by vacuum to afford (H) as a crude product (46 mg, 0.29 mmol, 86% yield) as a clear oil.

$^1$H-NMR; (CDCl$_3$) δ 0.89–0.98 (m, 3H)), 1.29–1.75 (m, 10H), 2.29–2.39 (m, 2H), 2.60–2.76 (m, 2H).

MS Calcd for C$_9$H$_{19}$NO (M+H)=158, observed (M+H)=158.

Synthesis of 4-Methyl-piperidin-4-ol (J).

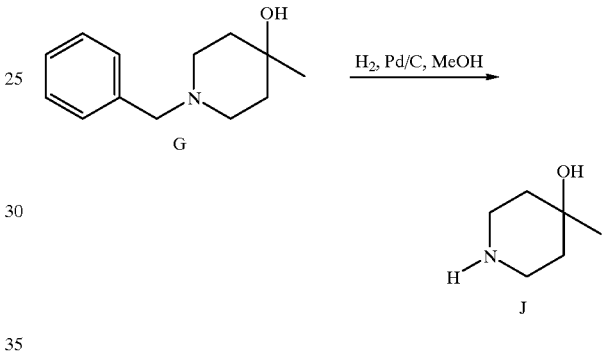

A reaction mixture of 1-benzyl-4-butyl-piperidin-4-ol (G) (218 mg, 1.06 mmol) and 10% Pd—C (20 mg) in 20 ml of MeOH was vigorously shaken overnight under H$_2$ (40 psi). The mixture was filtered off through celite and washed well with MeOH. The filtrate was evaporated by vacuum to afford (J) as acrude product (78 mg, 0.68 mmol, 64% yield) as a yellowish foam.

$^1$H-NMR; (CDCl$_3$) δ 1.26 (m, 3H)), 1.57–1.69 (m, 4H), 2.27–3.02 (m, 4H).

MS Calcd for C$_6$H$_{13}$NO (M+H)=116, observed (M+H)=116.

Synthesis of 4'-Hydroxy-3',4',5',6'-tetrahydro-2'H-[2,4'] bipyridinyl-1'-carboxylic acid tert-butyl ester (K).

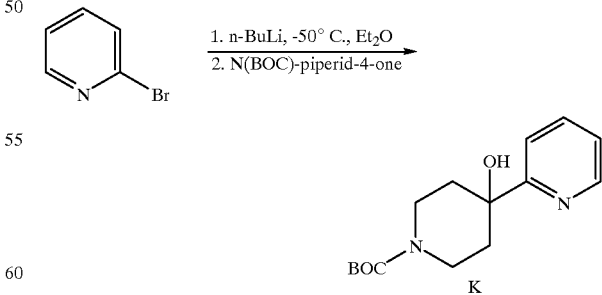

A solution of 2-bromopyridine (0.24 ml, 2.5 mmol) in 5 ml of ethyl ether was added dropwise to a well-stirred mixture of 2.5M n-BuLi in hexane (1.1 ml, 2.75 mmol) in 10 ml of ethyl ether at −50° C. under Ar (argon gas) and the mixture was stirred at −50° C. for 10 min. Another solution of tert-butyl-4-oxo-1-piperidine carboxylate (797 mg, 4.0 mmol) in 5 ml of ethyl ether was then added dropwise to the mixture. The resulting mixture was warmed up to −30° C. and stirred at −30° C. for 2 hours. After warming up to 0° C., the mixture was quenched with $NH_4Cl$ (0.75 g) in 25 ml of water. After stirring for 1 hour, the ether layer was separated and washed with water (20 ml), 1N HCl (3×10 ml) and dried over anhydrous $Na_2SO_4$, then concentrated by vacuum to afford (K) (181 mg, 0.65 mmol, 26% yield) as a brown color oil.

TLC; $R_f$=0.6 (Hexanes:EtOAc=2:1).

$^1$H-NMR; $(CDCl_3)$ δ 1.53 (s, 9H)), 1.91–2.02 (m, 2H), 2.45–2.49 (m, 2H), 3.27–3.36 (m, 2H), 3.73–3.76 (m, 1H), 4.14 (s, br, 2H), 5.29 (s, 1H), 7.30–7.32 (d, J=10 Hz, 2H), 7.73–7.78 (m, 1H), 8.57 (s, 1H).

$IR(CDCl_3)$ 3422, 2979, 1881, 1590, 1472, 1428, 1365, 1278, 1243, 1169, 1032, 863 $cm^{-1}$

MS Calcd for $C_{15}H_{22}N_2O_3$ (M+H)=279, observed (M+H)=279;

HPLC: 5% $CH_3CN/H_2O$ (0.1% TFA) to 90% $CH_3CN/H_2O$ (0.1% TFA)/10 min.

Retention time=4.755 min.

Synthesis of 2',3',5',6'-tetrahydro-1'H-[2,4']bipyridinyl-4'-ol (M).

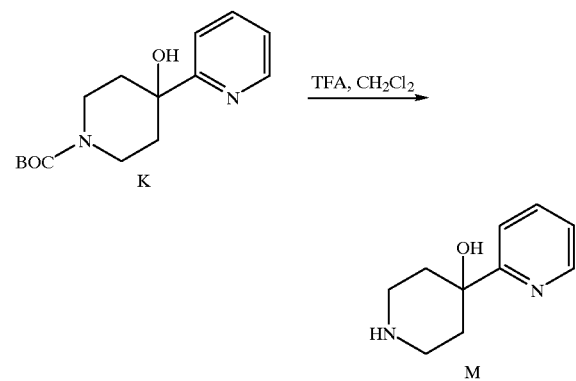

TFA (0.3 ml, 3.8 mmol) was added dropwise to a solution of(K) (175 mg, 0.63 mmol) in 5 ml of $CH_2Cl_2$ at 0° C. After stirring at 0° C. for 3 hours, the solvent was removed by vacuum and the residue slurried with 5% $Na_2CO_3$ solution (10 ml). The water was removed in vacuum and the residue was treated with $CH_2Cl_2$ (100 ml), dried over anhydrous $Na_2SO_4$, then concentrated by vacuum to afford (M) (67 mg, 0.38 mmol, 60% yield) as a yellowish solid.

mp: 128–132° C.

TLC; $R_f$=0.1 (Hexanes:EtOAc=2:1), $^1$H-NMR; $(CDCl_3)$ δ 1.64–1.69 (d, J=16 Hz, 2H), 2.01–2.11 (m, 4H), 3.07–3.32 (m, 2H), 7.23–7.27 (m, 2H), 7.43–7.46 (d, J=10 Hz, 1H), 7.74–7.90 (m, 1H), 8.55–8.57 (d, J=6 Hz, 1H). $IR(CDCl_3)$ 3392, 2359, 1674, 1594, 1521, 1472, 1433, 1287, 1084, 992, 780 $cm^{-1}$ MS Calcd for $C_{10}H_{14}N_2O$ (M+H)=179, observed (M+H)=179.

Other compounds of Formula I may be prepared in manners analogous to the general procedures described above or the detailed procedures described in the following examples.

Example 1 tert-Butoxycarbonylamino-phenyl-acetic acid cyclohexyl ester

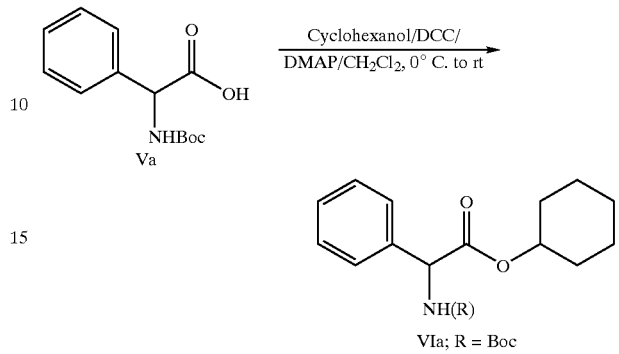

DCC (dicyclohexylcarbodiimide) (9.16 g, 44.4 mmol) was slowly added to an ice-cold suspension of Boc-L-α-phenylglycine (Va) (14.14 g, 40.35 mmol) and DMAP (N,N-dimethyl-4-aminopyridine) (0.5 g, 4.04 mmol) and cyclohexanol (5.12 ml, 48.42 mmol) in 60 ml of $CH_2Cl_2$. The resulting mixture was stirred at 0° C. to room temperature and monitored by TLC. Upon completion, the reaction was filtered and the precipitate was washed with $CH_2Cl_2$ to remove most of the N,N'-dicyclohexylurea. The filtrate was then partitioned between $CH_2C_2$ and saturated $NaHCO_3$ and the layers separated. The aqueous phase was extracted with $CH_2Cl_2$ (2×200 ml) and the combined organics were washed with $H_2O$ (150 ml), brine (150 ml) and dried over anhydrous $Na_2SO_4$ filtered and concentrated under reduced pressure. The resulting yellowish oil was column chromatographed on silica gel using hexane:EtOAc (2:1) as the elutant to yield VIa (13.37 g, 39.95 mmol, 99% yield) as a viscous yellow oil. TLC; $R_f$=0.7 (EtOAc:Hexanes=2:1).

$^1$H-NMR; $(CDCl_3)$ δ 1.27–1.83 (m, 10H), 1.47 (s, 9H) 4.78–4.83 (m, 1H), 5.31–5.33 (d, 1H, J=8 Hz), 5.61–5.63 (br, s, 1H, NH), 7.32–7.41 (m, 5H).

MS Calcd for $C_{19}H_{27}NO_4$ (M+H)=334, observed (M+H)=334

HPLC: 30% $CH_3CN/H_2O$ (0.1% TFA) to 90% $CH_3CN/H_2O$ (0.1% TFA)/20 min:

Retention time=14.61 min.

Example 2

Amino-phenyl-acetic acid cyclohexyl ester (VIIa)

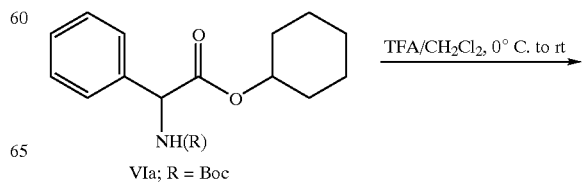

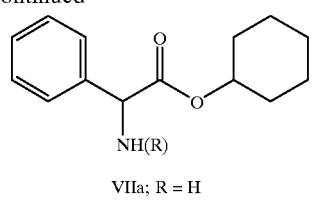

VIIa; R = H

TFA (30 ml, 385.1 mmol) was added dropwise to a solution of VIa (13.27 g, 39.79 mmol) in 50 ml of $CH_2Cl_2$ at 0° C. The resulting yellowish mixture was stirred overnight at 0° C. to room temperature. The reaction was then concentrated under reduced pressure and the resulting yellow oil was partitioned between $CH_2Cl_2$ (300 ml) and saturated $NaHCO_3$ (150 ml) and the layers separated. The aqueous phase was extracted with $CH_2Cl_2$ (2×150 ml) and the combined organics were washed with $H_2O$ (150 ml), brine (150 ml) and dried over anhydrous $Na_2SO_4$, filtered and concentrated under reduced pressure to yield VIIa (9.05 g, 38.99 mmol, 98% yield) as a yellow oil. TLC; $R_f$=0.7 ($CH_2Cl_2$:MeOH=9:1).

$^1$H-NMR ($CDCl_3$) δ 1.25–2.03 (m, 10H), 4.62 (s, 1H), 4.81–4.85 (m, 1H), 7.30–7.43 (m, 5H).

MS Calcd for $C_{14}H_{19}NO_2$ (M+H)=334, observed (M+H)=334.

HPLC: 5% $CH_3CN/H_2O$ (0.1% TFA) to 90% $CH_3CN/H_2O$ (0.1% TFA)/20 min.

Retention time=7.52 min.

Example 3

(2-Cyano-acetylamino)-phenyl-acetic acid cyclohexyl ester (IXa)

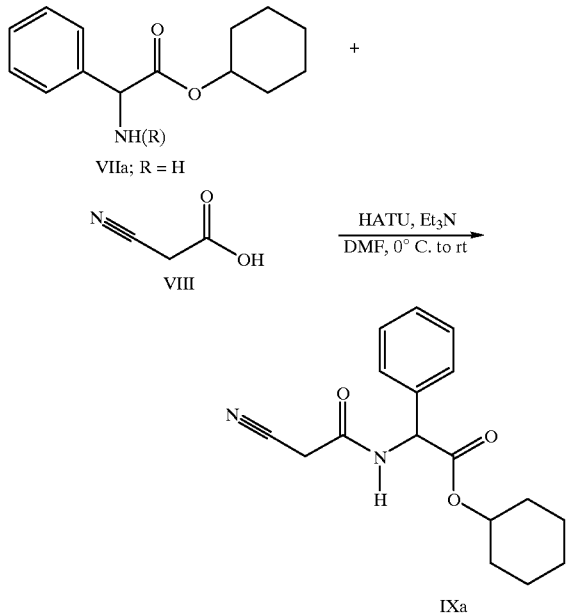

HATU (24 g, 63.1 mmol) was added to a solution of VIIa (9.01 g, 38.63 mmol), α-cyanoacetic acid (VIII) (3.58 g, 42.05 mmol) and triethylamine (12 ml, 84.1 mmol) in 60 ml of DMF at 0° C. The yellow solution was stirred overnight at 0° C. to room temperature. The reaction mixture was then partitioned between EtOAc (300 ml) and $H_2O$ (150 ml) and the layers separated. The organic phase was washed with saturated $NaHCO_3$ (150 ml), $H_2O$ (150 ml), 0.5 N HCl (150 ml), brine 150 ml) and dried over anhydrous $Na_2SO_4$, filtered and concentrated under reduced pressure. The resulting yellow oil was column chromatographed on silica gel using hexane:EtOAc (1:1) as the elutant to yield IXa (6.57 g, 21.88 mmol, 57% yield) as a white solid.

mp: 114–116° C.

TLC; $R_f$=0.8 (EtOAc:Hexanes=1:1)

$^1$H-NMR; ($CDCl_3$) δ 1.28–1.85 (m, 10H), 3.45 (s, 2H), 4.87–5.00 (m, 1H), 5.54–5.56 (d, 1H, J=7 Hz), 7.10–7.29 (br, s, 1H, NH), 7.29–7.39 (s, 5H)

MS Calcd for $C_{17}H_{20}N_2O_3$ (M+Na)=323, observed (M+Na)=323.

HPLC: 30% $CH_3CN/H_2O$ (0.1% TFA) to 90% $CH_3CN/H_2O$ (0.1% TFA)/20 min.

Retention time=9.67 min.

Example 4

(5-Amino-1H-pyrazole-4-carbonyl)-amino]-phenyl-acetic acid cyclohexyl ester (Xa)

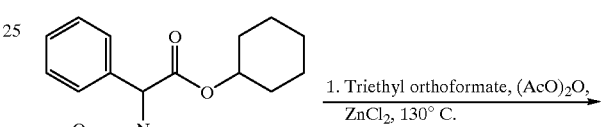

1. Triethyl orthoformate, $(AcO)_2O$, $ZnCl_2$, 130° C.
2. $NH_2NH_2·H_2O$, dioxane, 105° C.

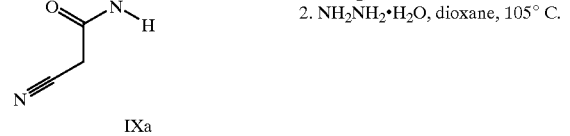

Xa

A round bottom flask was charged with IXa (2.3 g, 7.67 mmol), triethyl orthoformate (9.0 ml, 53.7 mmol), acetic anhydride (4.5 ml, 46.02 mmol) and anhydrous $ZnCl_2$ (1.05 g, 7.67 mmol) and then heated to reflux at 130° C. for 4 h. The yellow reaction mixture was concentrated under vacuum and azeotroped with toluene (3×15 ml). The result was titurated with $CH_2Cl_2$ (100 ml) filtered and washed with $CH_2Cl_2$ (150 ml). The filtrate was then concentrated under vacuum to yield a crude residue as yellow grease. The crude residue was treated with hydrazine hydrate (0.56 ml, 11.51 mmol) in 10 ml of 1,4-dioxane and then refluxed overnight at 105° C. The reaction was cooled to room temperature and concentrated under vacuum. The residue was partitioned between EtOAc (250 ml) and saturated $NaHCO_3$, brine (2×100 ml), dried over anhydrous $Na_2SO_4$, filtered and concentrated under vacuum to afford the crude product as a yellow grease. The crude product was column chromatographed using silica gel and eluted with $CH_2Cl_2$:MeOH::9:1 to afford Xa (1.343 g, 3.92 mmol, 51% yield) as a white solid.

mp: 92–94° C.

TLC; $R_f$=0.4 (CH$_2$Cl$_2$:MeOH=9:1).

$^1$H-NMR; (CDCl$_3$/CD$_3$OD) δ 1.14–1.37 (m, 4H), 1.38–1.41 (m, 2H), 1.52–1.54 (m, 2H); 1.67–1.71 (m, 2H), 4.68–4.72 (m, 1H), 5.53 (s, 1H), 7.29–7.30 (m, 5H), 7.79 (s, 1H).

MS Calcd for C$_{18}$H$_{22}$N$_4$O$_3$ (M+H)=343, observed (M+H)=343.

HPLC: 5% CH$_3$CN/H$_2$O (0.1% TFA) to 90% CH$_3$CN/H$_2$O (0.1% TFA)/20 min.

Retention time=9.24 min.

Example 5

(4-Oxo-1,4-dihydro-pyrazolo[3,4-d]pyrimidin-5-yl)-phenyl-acetic acid cyclohexyl ester (XIa)

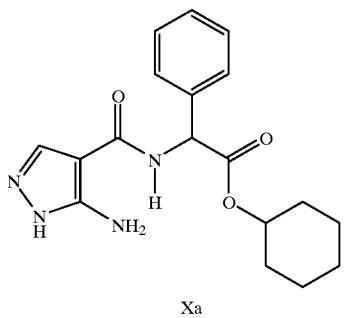

Xa

Formamide/145° C.

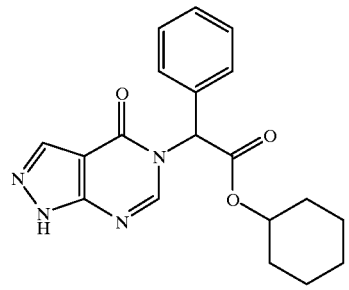

XIa

Xa (2.51 g, 7.33 mmol) in 20 ml of formamide was heated overnight to 145° C. The cooled reaction mixture was partitioned between EtOAc (250 ml) and saturated NaHCO$_3$ (2×100 ml), brine (100 ml), dried over anhydrous Na$_2$SO$_4$, filtered and concentrated under vacuum to afford a crude product as a yellow grease. The crude product was then column chromatographed using silica gel and eluted with CH$_2$Cl$_2$:EtOAc=1:1 to afford XIa (1.36 g, 3.85 mmol, 53%) as a yellowish solid.

mp: 176–180° C.

TLC; $R_f$=0.5 (CH$_2$Cl$_2$:EtOAc=1:1).

$^1$H-NMR; (CDCl$_3$) δ 1.24–1.91 (m, 10H), 4.98–5.03 (m, 1H), 6.84 (s, 1H), 7.29–7.30 (m, 2H), 7.36–7.49 (m, 3H), 7.91 (s, 1H), 8.23 (s, 1H).

MS Calcd for C$_{19}$H$_{20}$N$_4$O$_3$ (M+H)=353, observed (M+H)=353.

HPLC: 5% CH$_3$CN/H$_2$O (0.1% TFA) to 90% CH$_3$CN/H$_2$O (0.1% TFA)/20 min.

Retention time=12.9 min.

Example 6

2-Phenyl-(4-thioxo-1,4-dihydro-pyrazolo[3,4-d]pyrimidin-5-yl)-acetic acid cyclohexyl ester (XIIa)

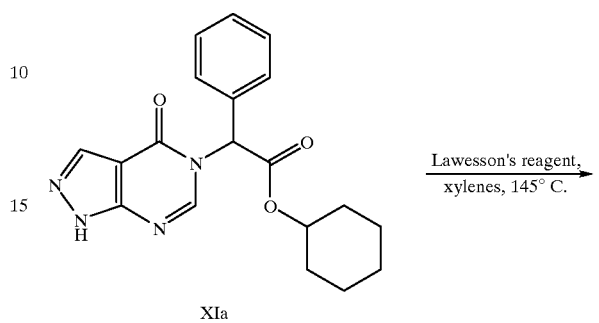

XIa

Lawesson's reagent, xylenes, 145° C.

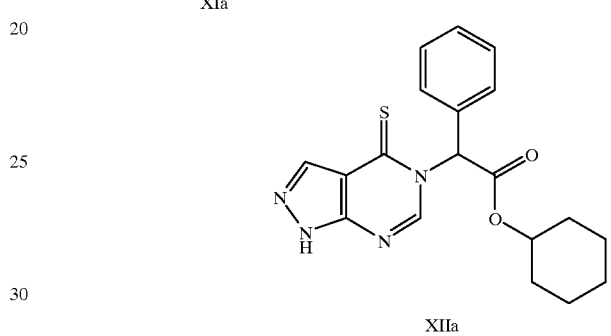

XIIa

A solution of XIa (0.326 g, 0.93 mmol) in 5 ml of xylene was purged with argon for 20 minutes, to which Lawesson's reagent (0.375 g, 0.93 mmol) was then added. The resulting mixture heated at 145° C. for 2 h under argon. The yellow reaction mixture was concentrated under vacuum. The crude product was column chromatographed using silica gel and eluted with CH$_2$Cl$_2$:EtOAc=1:1 to afford XIIa (0.316 g, 0.86 mmol, 92% yield) as an off white solid.

mp: 170–173° C.

TLC: $R_f$=0.8 (CH$_2$Cl$_2$:EtOAc=1:1).

$^1$H-NMR (CDCl$_3$) δ 1.30–1.93 (m, 10H), 5.03 (m, 1H), 7.41–7.49 (m, 5H), 7.98 (s, 1H), 8.04 (s, 1H), 8.38 (s, 1H), 10.55 (br, s, 1H, NH).

MS Calcd for C$_{19}$H$_{20}$N$_4$O$_2$S (M+H)=368, observed (M+H)=369.

HPLC: 5% CH$_3$CN/H$_2$O (0.1% TFA) to 90% CH$_3$CN/H$_2$O (0.1% TFA)/20 min.

Retention time=14.6 min.

Example 7

2-Phenyl-(4-thioxo-1,4-dihydro-pyrazolo [3,4-d] pyrimidin-5-yl)acetic acid (XIVa)

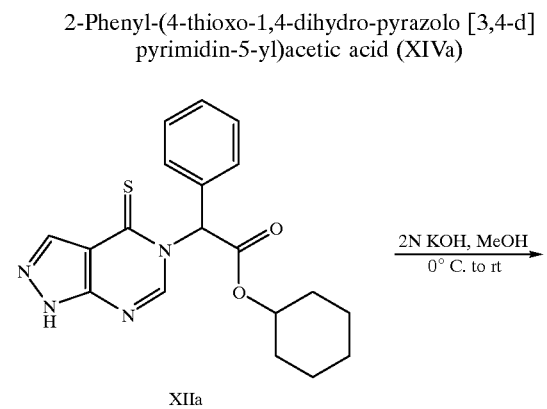

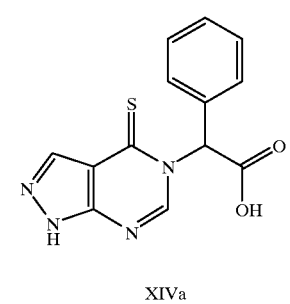

2N KOH aqueous solution (1.3 ml, 2.53 mmol) was added to a solution of 2-phenyl-(4-thioxo-1,4-dihydro-pyrazolo[3,4-d]pyrimidin-5-yl)acetic acid cyclohexyl ester (XIIa) (0.467 g, 1.27 mmol) in 10 ml of methanol at 0° C. The resulting yellow solution was stirred overnight at 0° C. to room temperature. The reaction mixture was concentrated by vacuum to remove most of methanol, and water was added. The pH was adjusted to 4.0 with aqueous 10% citric acid solution. The product was extracted with EtOAc (2×75 ml). The combined organic layer was washed with water, brine and dried over anhydrous $Na_2SO_4$, then concentrated by vacuum to afford (XIVa) (0.354 g, 1.19 mmol, 97% yield) as an off-white solid.

mp: 95–98° C.

TLC; $R_f$=0.1 ($CH_2Cl_2$:MeOH=9:1).

$^1$H-NMR; ($CD_3OD$) δ 3.23 (s, 1H), 7.50 (s, 5H), 8.08 (s, 1H), 8.09 (s, 1H), 8.34 (s, 1H, NH).

MS Calcd for $C_{13}H_{10}N_4O_2S$ (M+H)=287, observed (M+H)=287.

HPLC: 5% $CH_3CN/H_2O$ (0.1% TFA) to 90% $CH_3CN/H_2O$ (0.1% TFA)/20 min.

Retention time=3.9 min.

Example 8

(Method A): 1-Azepan-1-yl-2-phenyl-2-(4-thioxo-1,4-dihydro-1,4-dihrdropyrazolo[3,4-d]pyrimidin-5-yl)-ethanone (XVIa)

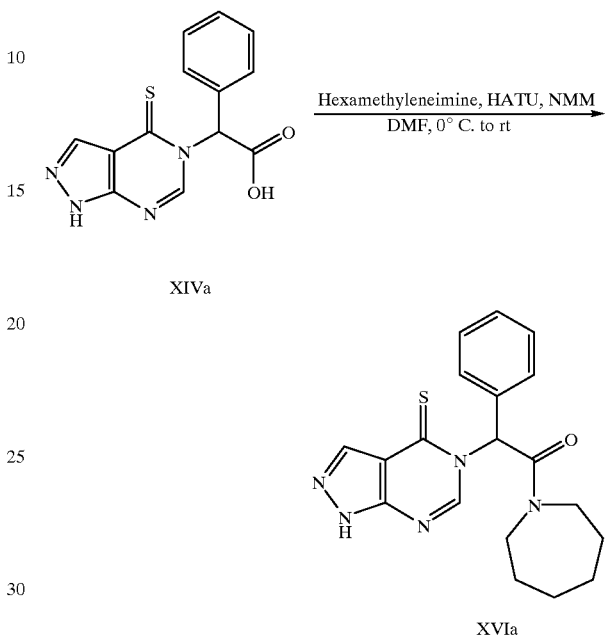

HATU [0-(7-azabenzotriazol-1-yl)-1,1,3,3-tetra-triethyl-uronium hexafluorophosphate] (0.125 g, 0.33 mmol) was added to a solution of 2-phenyl-(4-thioxo-1,4-dihydro-pyrazolo[3,4-d]pyrimidin-5-yl) acetic acid (XIVa) (0.064 g, 0.22 mmol) and hexamethyleneimine (0.023 g, 0.23 mmol) with 4-methylmorpholine (50 µl, 0.44 mmol) in 3 ml of DMF at 0° C. The resulting mixture of yellow solution was stirred overnight at 0° C. to room temperature. The yellow reaction mixture was partitioned between EtOAc (100 ml) and brine, saturated $NaHCO_3$, brine (3×50 ml). The organic layer was dried over anhydrous $Na_2SO_4$, filtered and concentrated under vacuum. The crude product was chromatographed using silica gel and eluted with $CH_2Cl_2$:EtOAc (1:1) to afford XVIa (0.043 g, 0.12 mmol, 53% yield) as a yellowish solid.

TLC; $R_f$=0.7 ($CH_2Cl_2$:EtOAc=1:1).

$^1$H-NMR; ($CDCl_3$) δ 1.60–2.08 (m, 8H), 3.37–3.84 (m, 4H), 7.44–7.49 (m, 5H), 8.09 (s, 1H), 8.36 (s, 1H), 8.41 (s, 1H), 10.65 (s, br, 1H, NH).

MS Calcd for $C_{19}H_{21}N_5OS$ (M+H)=368, observed (M+H)=368.

HPLC: 5% $CH_3CN/H_2O$ (0.1% TFA) to 90% $CH_3CN/H_2O$ (0.1% TFA)/20 min.

Retention time=11.66 min.

Example 9

1-Azocan-1-yl-2-phenyl-2-(4-thioxo-1,4-dihydro-1,4-dihydropyrazolo[3,4-d]pyrimidin-5-yl)-ethanone (XVIe)

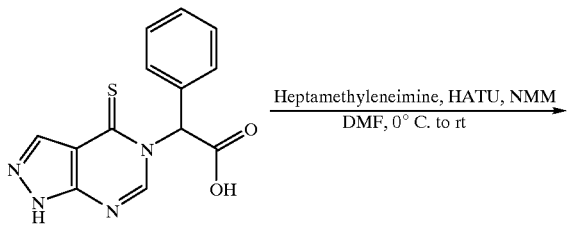

XIVa

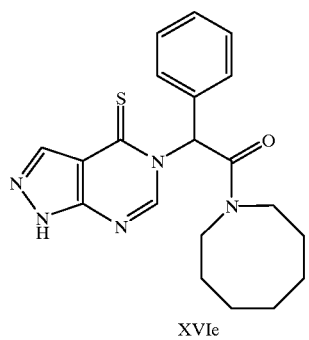

XVIe

Compound XVIe was prepared in the manner described in Example 8 to afford (0.018 g, 0.05 mmol, 28% yield) as a yellowish solid. The crude product was isolated by chromatography.

mp: 92–95° C.

TLC; $R_f$=0.7 (CH$_2$Cl$_2$:EtOAc=1:1).

$^1$H-NMR; (CDCl$_3$) δ 1.29–1.31 (m, 1H), 1.50–1.72 (m, 7H), 1.94–2.08 (m, 2H), 3.25–3.38 (m, 2H), 3.61–3.67 (m, 1H), 3.87–3.92 (m, 1H), 7.40–7.49 (m, 5H), 8.10 (s, 1H), 8.35 (s, 1H), 8.42 (s, 1H).

MS Calcd for C$_{20}$H$_{23}$N$_5$OS (M+H)=382, observed (M+H)=382.

HPLC: 5% CH$_3$CN/H$_2$O (0.1% TFA) to 90% CH$_3$CN/H$_2$O (0.1% TFA)/20 min.

Retention time=11.43 min.

Example 10

(Method B): N-Methoxy-N-methyl-2-phenyl-2-(4-thioxo-1,4-dihydro-1,4-dihydro-pyrazolo[3,4-d]pyrimidin-5-yl)-ethanone (XVIb)

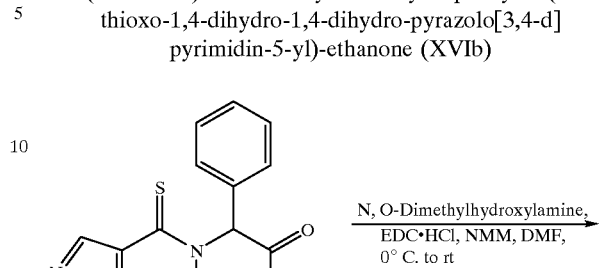

XIVa

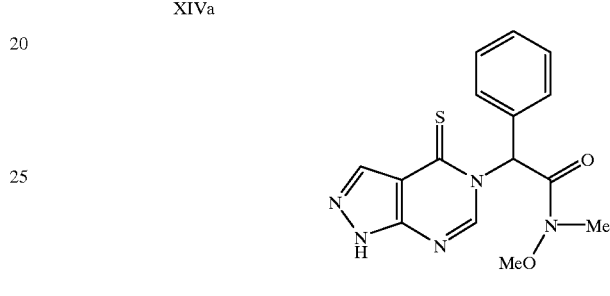

XVIb

1-[3-(dimethylamino)propyl]-3-ethylcarbodiimide HCl (0.044 g, 0.23 mol) was added to a solution of 2-phenyl-(4-thioxo-1,4-dihydro-pyrazolo[3,4-d]pyrimidin-5-yl) acetic acid (XIVa) (0.061 g, 0.21 mmol) and N,O-dimethylhydroxylamine HCl (0.023 g, 0.23 mmol) with 4-methylmorpholine (60 μl, 0.53 mol) in 2 ml of DMF at 0° C. The resulting mixture of yellow suspension was stirred overnight at 0° C. to room temperature. The yellow reaction mixture was filtered off and washed well with EtOAc. The filtrate was extracted with brine, saturated NaHCO$_3$, brine (3×50 ml). The organic layer dried over anhydrous Na$_2$SO$_4$, filtered through a pad of silica gel and eluted with EtOAc. The filtrate was concentrated under vacuum to afford (XVIb) (0.058 g, 0.18 mmol, 84% yield) as an off-white solid.

mp: 82–86° C.

TLC; $R_f$=0.5 (CH$_2$Cl$_2$:EtOAc=1:1).

$^1$H-NMR; (CDCl$_3$) δ 3.37 (s, 3H), 3.78 (s, 3H), 5.33–5.69 (s, br, 1H, NH), 7.387.40 (m, 2H), 7.47–7.49 (m, 3H), 8.12 (s, 1H), 8.49 (s, 1H).

MS Calcd for C$_{15}$H$_{15}$N$_5$O$_2$S (M+H)=330, observed (M+H)=330.

HPLC: 5% CH$_3$CN/H$_2$O (0.1% TFA) to 90% CH$_3$CN/H$_2$O (0.1% TFA)/20 min.

Retention time=11.63 min.

Example 11

1-(3-Hydroxy-piperidin-1-yl)-2-phenyl-2-(4-thioxo-1,4-dihydro-1,4-dihydro-pyrazolo[3,4-d]pyrimidin-5-yl)-ethanone (XVIc)

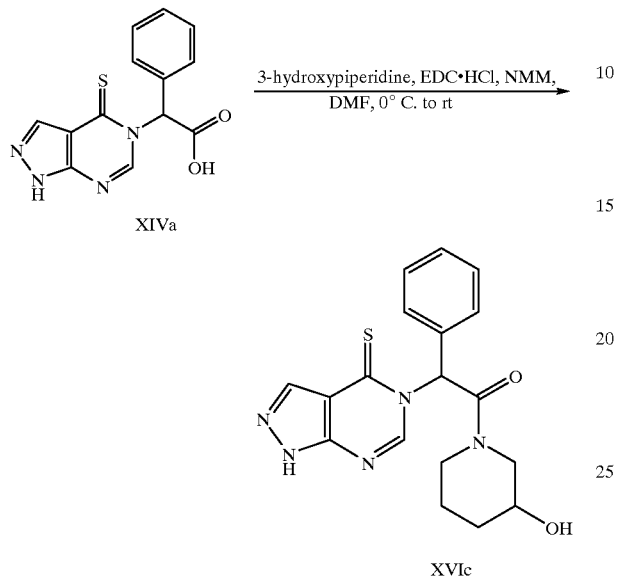

Compound XVIc was prepared in the manner described in Example 10 to afford (0.043 g, 0.103 mmol, 61% yield) as a yellowish solid.

mp: 142–146° C.

TLC; $R_f$=0.4 (CH$_2$Cl$_2$:EtOAc=1:1).

$^1$H-NMR; (CDCl$_3$) δ 1.63–2.09 (m, 6H), 3.01–3.80 (m, 3H), 7.42–7.49 (m, 5H), 8.09 (s, 1H), 8.45 (s, 1H).

MS Calcd for C$_{18}$H$_{19}$N$_5$O$_2$S (M+H)=370, observed (M+H)=370.

HPLC: 5% CH$_3$CN/H$_2$O (0.1% TFA) to 90% CH$_3$CN/H$_2$O (0.1% TFA)/20 min.

Retention time=9.9 min.

Example 12

2-Phenyl-1-(4-phenyl-piperidin-1-yl)-2-(4-thioxo-1,4-dihydro-1,4-dihydro-pyrazolo[3,4-d]pyrimidin-5-yl)-ethanone (XVId)

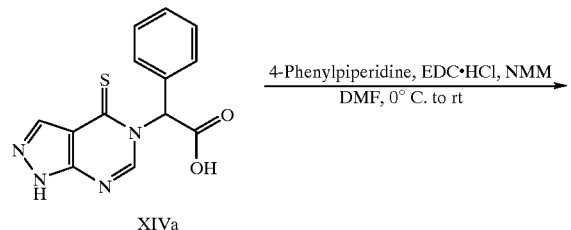

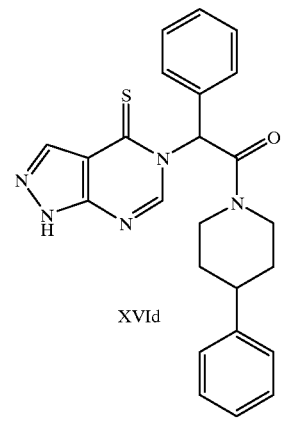

Compound XVId was prepared in the manner described in Example 10 to afford (0.046 g, 0.11 mmol, 37% yield) as a yellowish solid.

mp: 102–105° C.

TLC; $R_f$=0.8 (CH$_2$Cl$_2$:EtOAc=1:1).

$^1$H-NMR; (CDCl$_3$) δ 1.29 (m, 2H), 1.71–1.94 (m, 2H), 1.99–2.14 (d, J=14 Hz, 1H), 2.84–3.00 (m, 2H), 4.02–4.07 (d, J=7 Hz, 1H), 4.87–4.81 (d, J=13 Hz, 1H), 7.13–7.15 (d, J=7 Hz, 1H), 7.23–7.52 (m, 10H), 8.07–8.13 (d, J=19 Hz, 1H), 8.48–8.55 (d, J=22 Hz, 1H).

MS Calcd for C$_{24}$H$_{23}$N$_5$OS (M+H)=430, observed (M+H)=430.

HPLC: 5% CH$_3$CN/H$_2$O (0.1% TFA) to 90% CH$_3$CN/H$_2$O (0.1% TFA)/20 min.

Retention time=15.52 min.

Example 13

1-(4-Hydroxy-4-phenyl-piperidin-1-yl)-2phenyl-2-(4-thioxo-1,4-dihydro-1,4-dihydro-pyrazolo[3,4-d]pyrimidin-5-yl)-ethanone (XVIf)

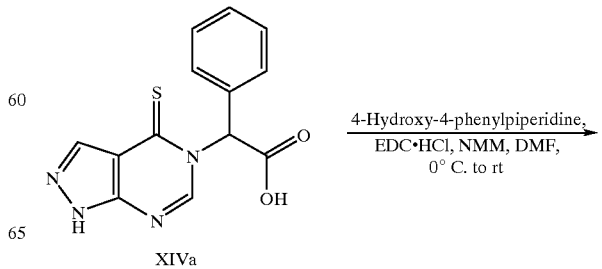

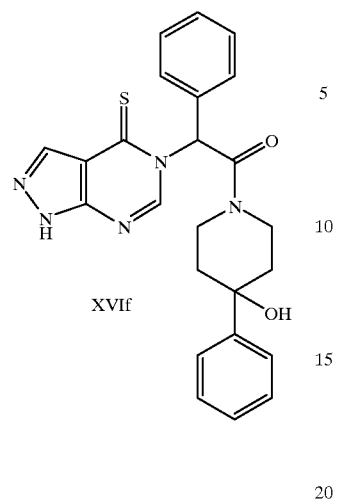

XVIf

Compound XVIf was prepared in the manner described in Example 10 to afford (0.044 g, 0.1 mmol, 49% yield) as a white solid.

mp: 142–146° C.

TLC; $R_f$=0.4 (CH$_2$Cl$_2$:EtOAc=1:1).

$^1$H-NMR; (CDCl$_3$) δ 1.22–1.32 (m, 1H), 1.49–1.63 (m, 1H), 1.64–1.68 (m, 1H), 1.84–1.94 (m, 1H), 2.02–2.21 (m, 1H), 2.47–2.58 (m, 1H), 3.33–3.55 (m, 2H), 3.81–3.86 (m, 1H), 4.65–4.72 (m, 1H), 7.30–7.53 (m, 10H), 8.04–8.14 (d, J=30 Hz, 1H), 8.39 (s, 1H), 8.48–8.50 (d, J=6 Hz, 1H).

MS Calcd for C$_{24}$H$_{23}$N$_5$O$_2$S (M+H))=446, observed MS=446.

HPLC: 30% CH$_3$CN/H$_2$O (0.1% TFA) to 90% CH$_3$CN/H$_2$O (0.1% TFA)/10 min.

Retention time=4.95 min.

Example 14

1-[4-(4-Bromo-phenyl)-4-hydroxy-piperidin-1-yl]-2-(4-thioxo-1,4-dihydro-1,4-dihydro-pyrazolo[3,4-d]pyrimidin-5-yl)-ethanone (XVIg)

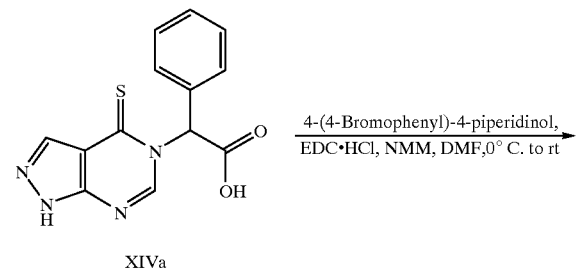

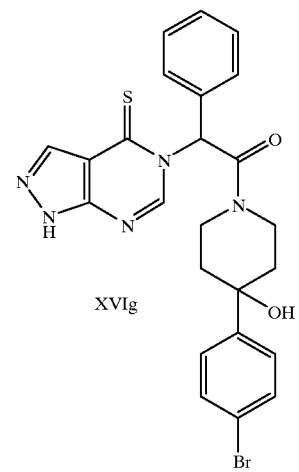

XVIg

Compound XVIg was prepared in the manner described by Example 10 to afford (0.034 g, 0.07 mmol, 33% yield) as an off-white solid.

mp: 155–160° C.

TLC; $R_f$=0.5 (CH$_2$Cl$_2$:EtOAc=1:1).

$^1$H-NMR; (CDCl$_3$) δ 0.89–1.01 (m, 1H), 1.22–1.46 (m, 1H), 1.56–1.64 (m, 1H), 1.79–1.89 (m, 1H), 1.96–2.14 (m, 1H), 2.46–2.55 (m, 1H), 3.03–3.54 (m, 1H), 3.82–3.86 (m, 1H), 4.64–4.72 (m, 1H), 7.23–7.64 (m, 9H), 8.03–8.13 (d, J=28 Hz, 1H), 8.39–8.48 (d, J=26 Hz, 1H).

MS Calcd for C$_{24}$H$_{22}$BrN$_5$O$_2$S (M$^{+81}$Br)=526 & (M$^{+79}$Br)=524, observed MS=526 & 524.

HPLC: 30% CH$_3$CN/H$_2$O (0.1% TFA) to 90% CH$_3$CN/H$_2$O (0.1% TFA)/10 min.

Retention time=6.24 min.

Example 15

1-(4-Acetyl-4-phenyl-piperidin-1-yl)-2-phenyl-2-(4-thioxo-1,4-dihydro-pyrazolo[3,4-d]pyrimidin-5-yl)-ethanone (XVIh)

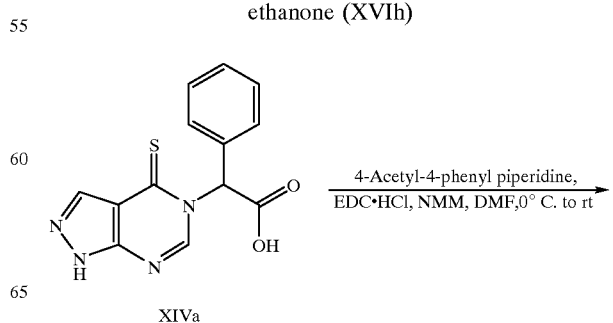

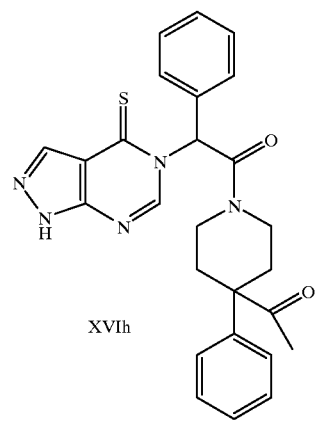

XVIh

Compound (XVIh) was prepared in the manmer described in Example 10 to afford (0.084 g, 0.18 mmol, 71% yield) as a yellowish solid.

mp: 125–128° C.

TLC; $R_f$=0.4 (CH$_2$Cl$_2$:EtOAc=1:1).

$^1$H-NMR; (CDCl$_3$) δ 1.22–1.32 (m, 1H), 1.49–1.63 (m, 1H), 1.64–1.68 (m, 1H), 1.84–1.94 (m, 1H), 2.02–2.21 (m, 1H), 2.47–2.58 (m, 1H), 3.33–3.55 (m, 2H), 3.81–3.86 (m, 1H), 4.64–4.72 (m, 1H), 7.30–7.53 (m, 1OH), 8.04–8.14 (d, J=30 Hz, 1H), 8.39 (s, 1H) 8.48–8.50 (d, J=6 Hz, 1H).

IR (CDCl$_3$) 3202, 2924, 1641, 1595, 1499, 1449, 1382, 1212, 1149, 1019, 911, 868, 731, 699 cm$^{-1}$

MS Calcd for C$_{24}$H$_{23}$N$_5$O$_2$S (M+H)=446, observed MS=446;

EA Calcd for C$_{24}$H$_{23}$N$_5$O$_2$S*0.2CH$_2$Cl$_2$*0.15 hexanes: C 64.90, H 5.53, N 13.97, Found: C 65.06, H 5.73, N 13.80

HPLC: 5% CH$_3$CN/H$_2$O (0.1% TFA) to 90% CH$_3$CN/H$_2$O (0.1% TFA)/20 min.

Retention time=8.449 min.

Example 16

(Method C): 2-Phenyl-1-(4-pyridin-2-yl-piperazin-1-yl)-2-(4-thioxo-1,4-dihydro-pyrazolo[3,4-d]pyrimidin-5-yl)-ethanone (XVIi)

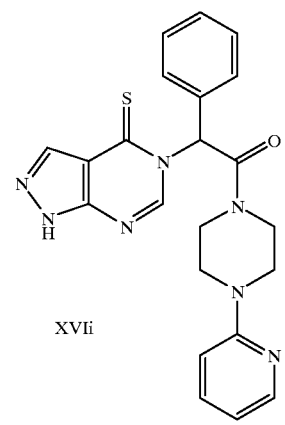

XVIi

1-[3-(dimethylamino)propyl]-3-ethycabodiimide HCl (1.5 eq. mmol) and following 1-hydrobenzatriazole hydrate (HOBT) (0.5 eq. mmol) was added to a solution of 2-phenyl-(4-thioxo-1,4-dihydro-pyrazolo[3,4-d]pyrimidin-5-yl) acetic acid (XIVa) (1.0 eq. mmol) and a corresponding amine such as 1-(2-pyridyl)piperazine(1.5 eq. mmol) with 4-methylmorpholine (3.0 eq. mmol) in DMF at 0° C. The resulting mixture was stirred overnight at 0° C. to room temperature. The yellow reaction mixture was filtered off and washed well with EtOAc. The filtrate was extracted with brine, saturated NaHCO$_3$, brine. The organic layer was dried over anhydrous Na$_2$SO$_4$, and then was concentrated under vacuum. The crude product was chromatographed using silica gel and eluted with CH$_2$Cl$_2$:EtOAc/1:1 to afford (XVIi) (0.029 g, 0.07 mmol, 22% yield) as a white solid.

mp: 242–246° C.; TLC; $R_f$=0.5 (CH$_2$Cl$_2$:EtOAc=1:1).

$^1$H-NMR; (CDCl$_3$) δ 3.41–3.49 (m, 2H), 3.52–3.73 (m, 2H), 3.81–3.99 (m, 4H), 6.67–6.73 (m, 1H), 7.43–7.56 (m, 5H), 8.06 (s, 1H), 8.20–8.23 (d, J=6 Hz, 1H), 8.36 (s, 1H), 8.48 (s, 1H).

IR(CDCl$_3$) 3300, 2995, 1657, 1594, 1479, 1434, 1383, 1232, 1150, 1031, 982, 912, 867 cm$^{-1}$

HRMS Calcd for C$_{22}$H$_{22}$N$_7$OS M=431.1607, observed (M+H)=432.1613;

HPLC: 5% CH$_3$CN/H$_2$O (0.1% TFA) to 90% CH$_3$CN/H$_2$O (0.1% TFA)/10 min.

Retention time=5.03 min.

Example 17

2-Phenyl-1-(4-phenyl-2-yl-piperazin-1-yl)-2-(4-thioxo-1,4-dihydro-pyrazolo[3,4-d]pyrimidin-5-yl)-ethanone (XVIj)

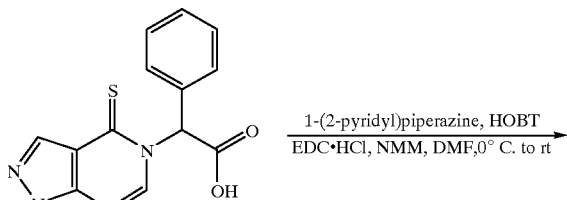

XIVa

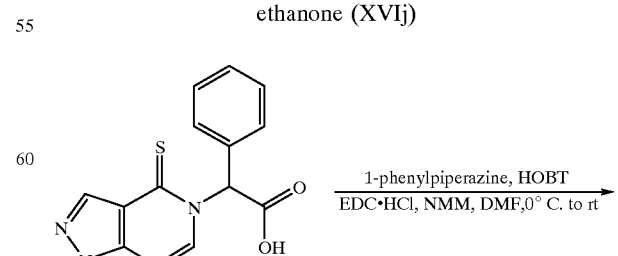

XIVa

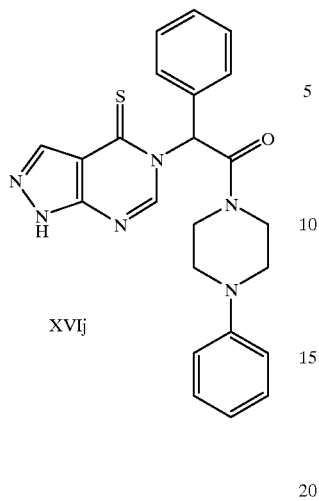

XVIj

Compound (XVIj) was prepared in the manner described in Example 16 to afford (0.068 g, 0.16 mmol, 53% yield) as a white solid.

mp: 241–245° C.

TLC; $R_f$=0.8 (CH$_2$Cl$_2$:EtOAc=1:1).

$^1$H-NMR; (CDCl$_3$) δ 3.00–3.06 (m, 1H), 3.25–3.35 (m, 2H), 3.53–3.58 (m, 1H), 3.83–4.08 (m, 2H), 6.91–6.96 (m, 2H), 7.28–7.59 (m, 1OH), 8.06 (s, 1H), 8.36 (s, 1H), 8.50 (s, 1H), 10.85 (s, br, 1H, NH).

IR(CDCl$_3$) 3178, 2360, 1657, 1595, 1495, 1449, 1383, 1229, 1150, 1029, 913, 867 cm$^{-1}$

HRMS Calcd for C$_{23}$H$_{22}$N$_6$OS (M+H)=431.1654, observed (M+H)=432.1672;

HPLC: 5% CH$_3$CN/H$_2$O (0.1% TFA) to 90% CH$_3$CN/H$_2$O (0.1% TFA)/10 min.

Retention time=7.94 min.

Example 18

1-[4-(4-Methoxy-phenyl)-piperazin-1-yl]-2-phenyl-2-(4-thioxo-1,4-dihydro-pyrazolo[3,4-d]pyrimidin-5-yl)-ethanone (XVIk)

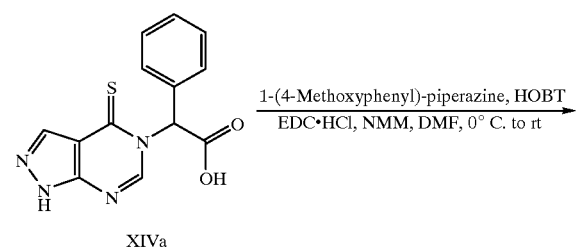

XIVa

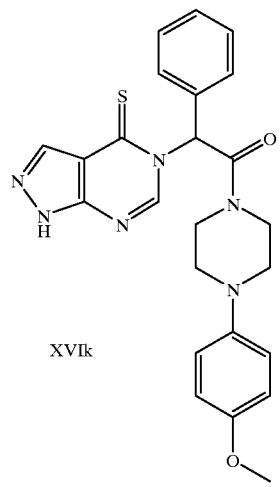

XVIk

Compound (XVIk) was prepared in the manner described in Example 16 to afford (0.071 g, 0.15 mmol, 55% yield) as a yellowish solid.

mp: 114–118° C.; TLC; $R_f$=0.8 (CH$_2$Cl$_2$:EtOAc=1:1).

$^1$H-NMR; (CDCl$_3$) δ 2.88–2.94 (m, 1H), 3.12–3.22 (m, 2H), 3.48–3.59 (m, 1H), 3.83 (s, 3H), 3.82–3.99 (m, 1H), 4.00–4.16 (m, 1H), 6.85–6.94 (m, 2H), 7.32–7.64 (m, 9H), 8.06 (s, 1H), 8.36 (s, 1H), 8.50 (s, 1H), 10.07 (s, br, 1H, NH).

IR(CDCl$_3$) 3192, 1650, 1594, 1512, 1444, 1383, 1280, 1228, 1149, 1031, 913 cm$^{-1}$

HRMS Calcd for C$_{24}$H$_{24}$N$_6$O$_2$S (M+H)=461.1760, observed (M+H)=461.1765;

HPLC: 5% CH$_3$CN/H$_2$O (0.1% TFA) to 90% CH$_3$CN/H$_2$O (0.1% TFA)/10 min.

Retention time=6.365 min.

Example 19

1-(4-Hydroxy-3',4',5',6'-tetrahydro-2H-[2,4]bipyridinyl-1'-yl]-2-phenyl-2-(4-thioxo-1,4-dihydro-pyrazolo[3,4-d]pyrimidin-5-yl)-ethanone (XVIm)

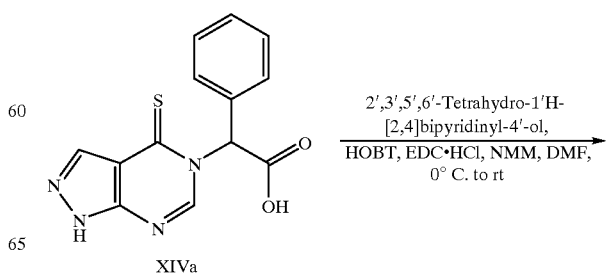

XIVa

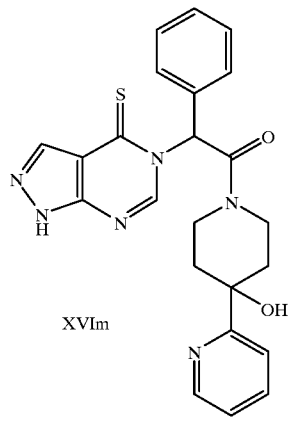

XVIm

Compound (XVIm) was prepared in the manner described in Example 16 to afford (0.066 g, 0.15 mmol, 43% yield) as an off-white solid.

mp: 138–142° C.; TLC; $R_f$=0.5 (CH$_2$Cl$_2$:EtOAc=1:1).

$^1$H-NMR; (CDCl$_3$) δ 1.62–1.79 (m, 1H), 1.99–2.08 (m, 1H), 2.47–2.55 (m, 1H), 2.91–2.99 (d, J=22 Hz, 1H), 3.37–3.37 (m, 1H), 3.42–3.62 (m, 1H) 3.87–3.91 (d, J=9 Hz, 1H), 4.74–4.79 (d, J=12 Hz, 1H), 5.64 (s, br, 1H, OH), 6.93–7.64 (m, 8H), 7.72–7.84 (m, 1H), 8.05–8.14 (d, J=27 Hz, 1H), 8.54 (s, 1H), 8.56 (s, 1H), 10.77 (s, br, 1H, NH).

IR(CDCl$_3$) 3191, 2922, 2359, 1650, 1594, 1567, 1498, 1383, 1292, 1215, 1149, 1027, 974, 902, 868 cm$^{-1}$

HRMS Calcd for C$_{23}$H$_{22}$N$_6$O$_2$S (M+H)=447.1603, observed (M+H)=447.1616;

HPLC: 5% CH$_3$CN/H$_2$O (0.1% TFA) to 90% CH$_3$CN/H$_2$O (0.1% TFA)/10 min.

Retention time=4.872 min.

Example 20

1-(4-Butyl-4-hydroxy-piperidin-1-yl)-2-phenyl-2-(4-thioxo-1,4-dihydro-pyrazolo[3,4-d]pyrimidin-5-yl)-ethanone (XVIn)

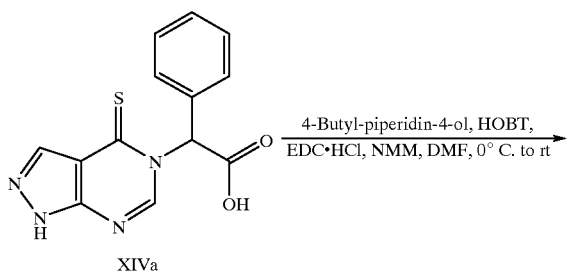

XIVa

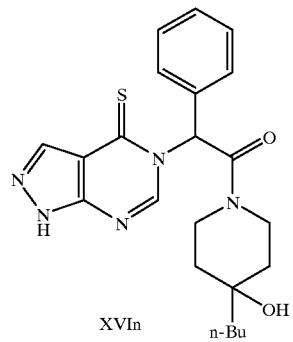

XVIn

Compound (XVIn) was prepared in the manner described in Example 16 to afford (0.017 g, 0.04 mmol, 22% yield) as a white solid.

mp: 98–102° C.

TLC; $R_f$=0.45 (CH$_2$Cl$_2$:EtOAc=1:1).

$^1$H-NMR; (CDCl$_3$) δ 0.91–0.97 (m, 2H), 1.01–1.63 (m, 7H), 1.96–2.08 (m, 1H), 3.05–3.39 (m, 2H), 3.60–3.74 (m, 2H), 4.11–4.53 (m, 1H), 5.77 (s, br, 1H), 7.38–7.49 (m, 5H), 8.03–8.07 (d, J=13 Hz, 1H), 8.34 (s, 1H), 8.48–8.51 (d, J=34 Hz, 1H), 10.97 (s, br, 1H, NH).

IR(CDCl$_3$) 3194, 2930, 2359, 1643, 1595, 1566, 1499, 1451, 1382, 1291, 1216, 1150, 1051, 972, 911, 868, 733 cm$^{-1}$

HRMS Calcd for C$_{22}$H$_{27}$N$_5$O$_2$S (M+H)=426.1964, observed (M+H)=426.1975;

HPLC: 5% CH$_3$CN/H$_2$O (0.1% TFA) to 90% CH$_3$CN/H$_2$O (0.1% TFA)/10 min.

Retention time=7.255 min.

Example 21

N-Methyl-2-N-diphenyl-2-(4-thioxo-1,4-dihydro-pyrazolo[3,4-d]pyrimidin-5-yl)-acetamide (XVIo)

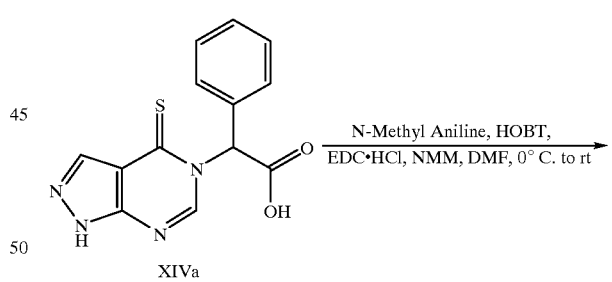

XIVa

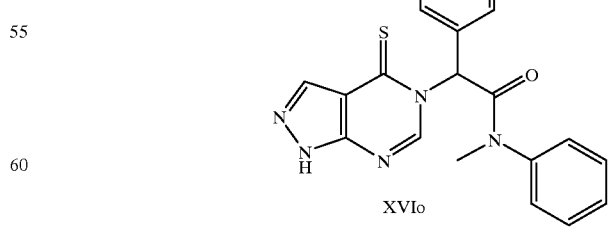

XVIo

Compound (XVIo) was prepared in the manner described in Example 16 to afford (0.011 g, 0.03 mmol, 15% yield) as an off-white solid.

mp: 218–222° C.

TLC; $R_f$=0.3(CH$_2$Cl$_2$:EtOAc=1:1).

$^1$H-NMR; (CDCl$_3$) δ 3.40 (s, 3H), 7.13–7.43 (m, 10H), 7.78 (s, 1H), 8.16(s, 1H), 8.33 (s, 1H).

IR(CDCl$_3$)3195, 2926, 2359, 1665, 1594, 1562, 1496, 1384, 1291, 1212, 1147, 1046 cm$^{-1}$

HRMS Calcd for C$_{20}$H$_{17}$N$_5$OS (M+H)=376.1232, observed (M+H)=376.1240;

HPLC: 5% CH$_3$CN/H$_2$O (0.1% TFA) to 90% CH$_3$CN/H$_2$O (0.1% TFA)/10 min.

Retention time=7.813 min.

Example 22

1-(4-Methyl-4-hydroxy-piperidin-1-yl)-2-phenyl-2-(4-thioxo-1,4-dihydro-pyrazolo[3,4-d]pyrimidin-5-yl)-ethanone (XVIp)

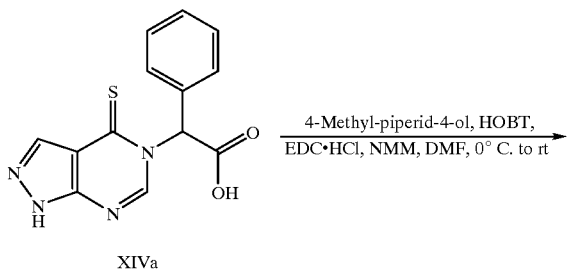

XIVa

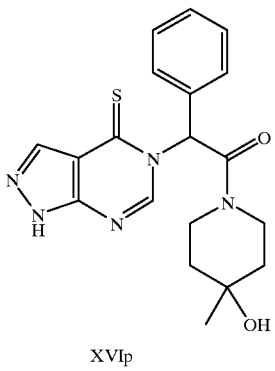

XVIp

Compound (XVIp) was prepared in the manner described in Example 16 to afford (0.044 g, 0.11 mmol, 28% yield) as a white solid.

mp: 140–144° C.

TLC; $R_f$=0.3 (CH$_2$Cl$_2$:EtOAc=1:1).

$^1$H-NMR: (CDCl$_3$) δ 1.39 (s, 3H), 3.23–3.72 (m, 6H), 4.27–4.46 (m, 2H), 7.32–7.50 (m, 5H), 8.04–8.07 (d, J=10 Hz, 1H), 8.34 (s, 1H), 8.48–8.52 (d, J=11 Hz, 1H).

IR(CDCl$_3$) 3290, 2963, 2360, 1643, 1595, 1565, 1498, 1450, 1381, 1237, 1216, 1150, 970, 910, 867 cm$^{-1}$

HRMS Calcd for C$_{19}$H$_{21}$N$_5$O$_2$S (M+H)=384.1494, observed (M+H)=384.1500;

HPLC: 5% CH$_3$CN/H$_2$O (0.1% TFA) to 90% CH$_3$CN/H$_2$O (0.1% TFA)/10 min.

Retention time=5.82 min.

Example 23

(Method D): N-Ethyl-N-isopropyl-2-phenyl-2-(4-thioxo-1,4-dihydro-pyrazolo[3,4d]pyrimidin-5-yl)-acetamide (XVIq)

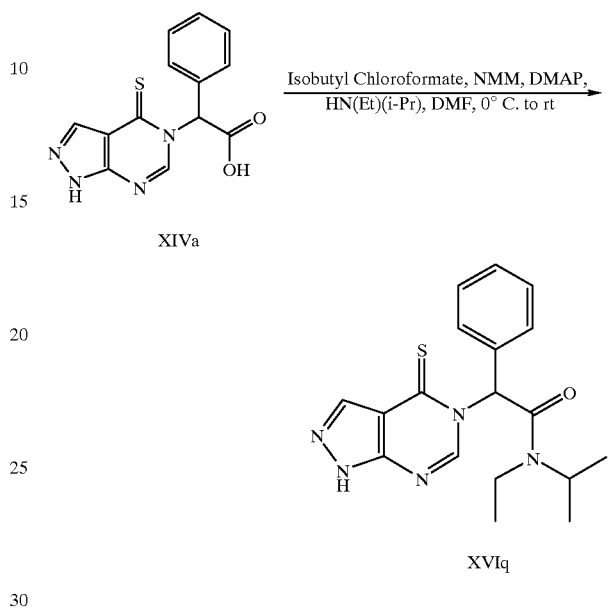

Isobutyl chloroformate (1.1 eq. mmol) was added dropwise to a solution of 2-phenyl-(4-thioxo-1,4-dihydro-pyrazolo[3,4-d]pyrimidin-5-yl) acetic acid (XIVa)(1.0 eq. mmol) with 4-methylmorpholine (1.0 eq. mmol) in DMF at 0° C. The mixture was stirred for 30 min at 0° C. and then added to a solution of a corresponding amine such as N-ethylisopropylamine (1.1 eq. mmol) with DMAP (0.1 eq. mmol) in DMF at 0° C. The resulting mixture was stirred overnight at 0° C. to room temperature. The reaction mixture was partitioned between EtOAc and brine, saturated NaHCO$_3$, brine, pH 6 buffer, brine. The organic layer dried over anhydrous Na$_2$SO$_4$, and then was concentrated under vacuum. The crude product was chromatographed using silica gel and eluted with CH$_2$Cl$_2$:EtOAc (1:1) to afford (XVIq) (0.034 g, 0.1 mmol, 32% yield) as a clear grease.

TLC; $R_f$=0.9 (CH$_2$Cl$_2$:EtOAc=1:1).

$^1$H-NMR; (CDCl$_3$) δ 0.96–0.98 (d, J=8 Hz, 6H), 1.29(s, 1H), 2.00–2.09 (m, 2H), 4.05–4.20(m, 3H), 7.30–7.64 (m, 5H), 8.06 (s, 1H), 8.38 (s, 1H), 10.81 (s, br, 1H, NH).

IR(CDCl$_3$) 3095, 2963, 2359, 1742, 1596, 1558, 1498, 1455, 1380, 1287, 1208, 1177, 1150, 1005, 912, 865, 745 cm$^{-1}$

MS Calcd for C$_{18}$H$_{21}$N$_5$OS (M+H)=356, observed (M+H)=356;

HPLC: 5% CH$_3$CN/H$_2$O (0.1% TFA) to 90% CH$_3$CN/H$_2$O (0.1% TFA)/10 min.

Retention time=8.87 min.

Example 24

N,N-Diethyl-2-phenyl-2-(4-thioxo-1,4-dihydro-pyrazolo[3,4-d]pyrimidin-5-yl)-acetamide (XVIr)

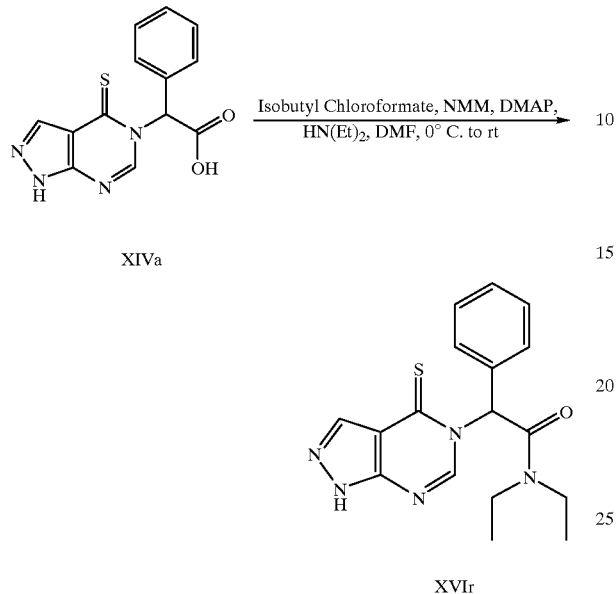

Compound (XVIr) was prepared in the manner described in Example 23 to afford (0.016 g, 0.05 mmol, 16% yield) as a yellowish solid.

mp: 143–146° C.

TLC; $R_f$=0.7 (CH$_2$Cl$_2$:EtOAc=1:1).

$^1$H-NMR; (CDCl$_3$) δ 1.23–1.29 (m, 6H), 3.37–3.44 (m, 3H), 3.64–3.71(m, 1H), 7.39–7.49 (m, 5H), 8.12(s, 1H), 8.34 (s, 1H), 8.44 (s, 1H), 10.85 (s, br, 1H, NH).

IR (CDCl$_3$) 3187, 2977, 2359, 1743, 1650, 1594, 1562, 1499, 1482, 1382, 1213, 1149, 1048, 867, 748 cm$^{-1}$

HRMS Calcd for C$_{17}$H$_{19}$N$_5$OS (M+H)=342.1389, observed (M+H)=342.1401;

HPLC: 5% CH$_3$CN/H$_2$O (0.1% TFA) to 90% CH$_3$CN/H$_2$O (0.1% TFA)/10 min.

Retention time=7.66 min.

Example 25

2-(3-Allyoxy-phenyl)-1-(4-hydroxy-4-phenyl-piperidin-1-yl)-2-(4-thioxo-1,4-dihydro-pyrazolo[3,4-d]pyrimidin-5-yl)-ethanone (XVIs)

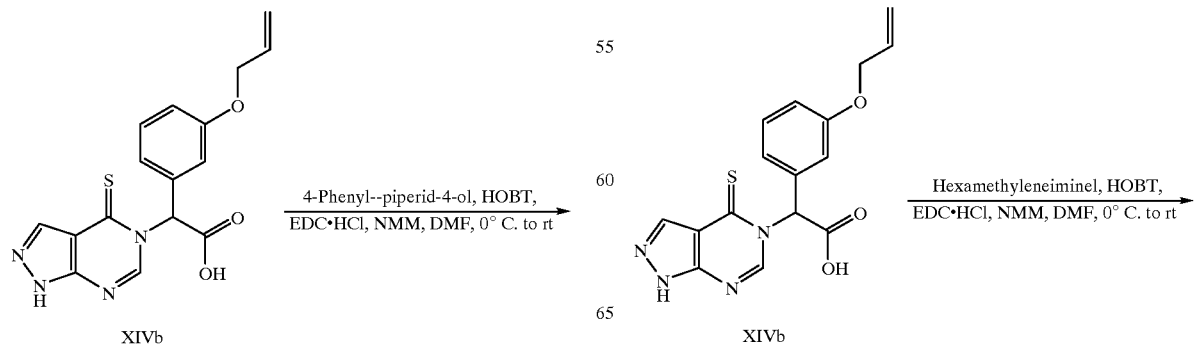

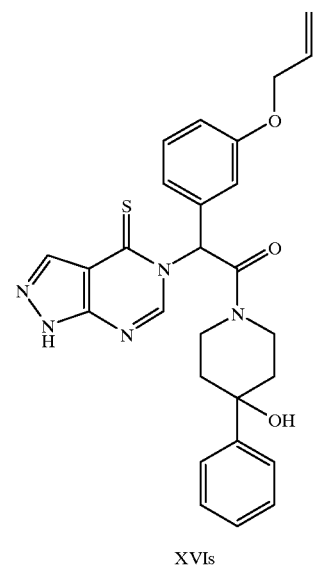

Compound (XVIs) was prepared in the manner described in Example 16 to afford (0.052 g, 0.1 mmol, 32% yield) as a white solid.

mp: 116–120° C.

TLC; $R_f$=0.7 (CH$_2$Cl$_2$:EtOAc=1:1).

$^1$H-NMR (CDCl$_3$): δ 1.22–1.29 (m, 7H), 1.83–1.92 (m, 1H), 2.08–2.14 (m, 1H), 2.50–2.54 (m, 1H), 3.29–3.36 (m, 1H), 3.47–3.57 (m, 1H), 3.81–3.84 (m, 1H), 4.56 (s, 1H), 4.58–4.68 (m, 1H), 5.30–5.48 (m, 2H), 6.00–6.11 (m, 1H), 6.94–7.10 (m, 2H), 7.30–7.63 (m, 9H), 8.03–8.18 (d, J=9 Hz, 1H), 8.37 (s, 1H), 8.48 (s, 1H), 10.78 (s, br, 1H, NH).

IR (CDCl$_3$) 3197, 2359, 1646, 1594, 1558, 1506, 1456, 1374, 1267, 1212, 1144, 1018, 908 cm$^{-1}$

HRMS Calcd for C$_{27}$H$_{27}$N$_5$O$_3$S (M+H)=512.1913, observed (M+H)=502.1909;

HPLC: 5% CH$_3$CN/H$_2$O (0.1% TFA) to 90% CH$_3$CN/H$_2$O (0.1% TFA)/10 min.

Retention time=5.982 min.

Example 26

2-(3-Allyoxy-phenyl)-1-azepan-1-yl-2-(4-thioxo-1,4-dihydro-pyrazolo[3,4-d]pyrimidin-5-yl)-ethanone (XVIt)

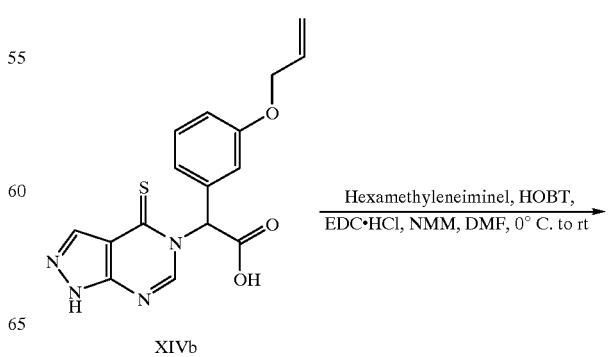

107
-continued

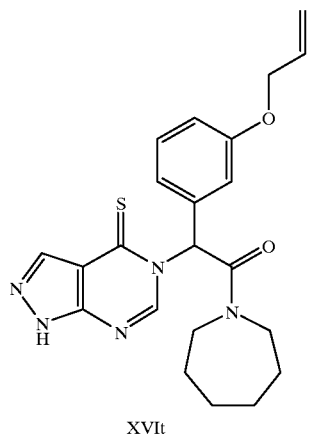

XVIt

Compound (XVIt) was prepared in the manner described in Example 16 to afford (0.078 g, 0.18 mmol, 47% yield) as a yellowish solid.

mp: 75–80° C.

TLC; $R_f$=0.75($CH_2Cl_2$:EtOAc=1:1).

$^1$H-NMR (CDCl$_3$): δ 1.50–1.82 (m, 2H), 2.02–2.08 (m, 2H), 3.33–3.50 (m, 2H), 3.51–3.91 (m, 2H), 4.55–4.56 (m, 2H), 5.31–5.47 (d, d, J=6, 7 Hz, 2H), 5.99–6.12 (m, 1H), 6.96–7.02 (m, 3H), 7.32–7.42 (m, 5H), 8.12 (s, 1H), 8.35 (s, 1H), 10.87 (s, br, 1H, NH).

IR (CDCl$_3$) 3648, 3566, 3184, 2928, 2359, 1652, 1594, 1558, 1489, 1456, 1436, 1374, 1289, 1209, 1146, 1022 cm$^{-1}$

HRMS Calcd for $C_{22}H_{25}N_5O_2S$ (M+H)=424.1807, observed (M+H)=424.1806;

HPLC: 5% CH$_3$CN/H$_2$O (0.1% TFA) to 90% CH$_3$CN/H$_2$O (0.1% TFA)/10 min.

Retention time=7.376 min.

Synthesis of XIVb

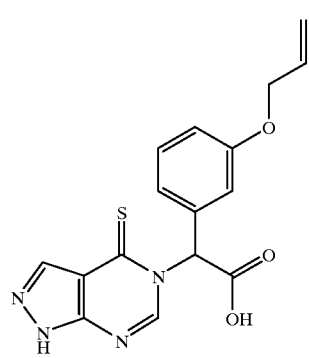

XIVb

Example 27

(3-Allyloxy-phenyl)-(2-cyano-ethanolyamino)-acetic acid cyclohexyl ester (IXb) (R$_1$ is 3-allyloxy-phenyl)

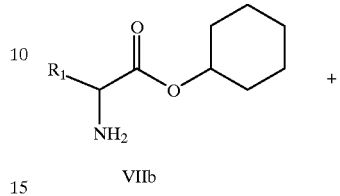

VIIb

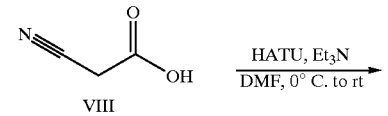

VIII

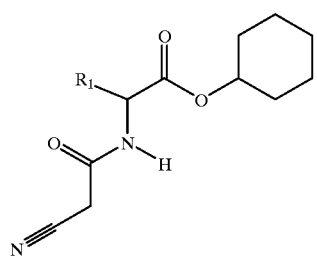

IXb

HATU (5.34 g, 14.05 mmol) was added to a solution of (VIIb) (3.39 g, 11.71 mmol) and cyanoacetic acid (VIII) (1.0 g, 11.71 mmol) with Et$_3$N (3.3 ml, 23.42 mmol) in 40 ml of DMF at 0° C. The resulting mixture was stirred overnight at 0° C. to room temperature. The reaction mixture was partitioned between EtOAc (300 ml) and saturated NaHCO$_3$, brine, 0.5N HCl, brine (4×100 ml). The organic layer was dried over Na$_2$SO$_4$, then evaporated by vacuum. The residue of yellow oil was purified by flash silica gel chromatography, eluted with hexanes:EtOAc (1:1) to afford (IXb) (2.48 g, 6.96 mmol, 59% yield) as white solid.

mp: 95–98° C.

TLC: $R_f$=0.7 (Hexanes:EtOAc=1:1).

$^1$H-NMR (CDCl$_3$): δ 1.26–1.85(m, 10H), 3.45 (s, 2H), 4.55–4.57(m, 2H), 4.86–4.87 (m, 2H), 5.31–5.52 (m, 2H), 6.02–6.13 (m, 1H), 6.90–6.98 (m, 3H), 7.07–7.28 (m, 1H).

IR (CDCl$_3$) 3301, 2934, 2857, 1737, 1659, 1599, 1547, 1492, 1445, 1391, 1360, 1275, 1205, 1011, 921 cm$^{-1}$

MS Calcd for $C_{20}H_{24}N_2O_4$ (M+H)=356, observed (M+H)=356

HPLC: 30% CH$_3$CN/H$_2$O (0.1% TFA) to 90% CH$_3$CN/H$_2$O (0.1% TFA)/10 min.

Retention time=7.269 min.

Example 28

(3-Allyloxy-phenyl)-{[1-(5-amino-1H-pyrazol-4-yl)-methanoyl]-amino}-acetic acid cyclohexyl ester (Xb)($R_1$ is 3-allyloxy-phenyl)

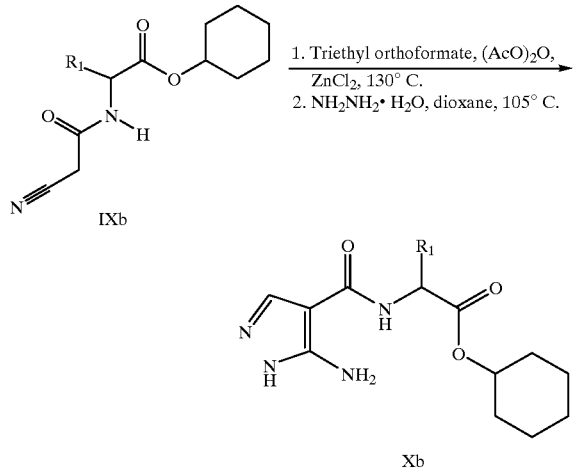

The reaction mixture of (IXb) (2.47 g, 6.94 mmol), triethylorthoformate (8.1 ml, 48.58 mmol), acetic anhydride (4.0 ml, 41.64 mmol) and anhydrous $ZnCl_2$ (1.0 g, 6.94 mmol) was heated to reflux at 130° C. for overnight under Ar. The mixture was evaporated by vacuum, then azeotroped with toluene (3×50 ml). The residue was treated with $CH_2Cl_2$. The solid of $ZnCl_2$ salt was filtered off and washed well with $CH_2Cl_2$. The filtrate was evaporated by vacuum to give a crude product. The reaction mixture of crude product from above with hydrazine monohydrate (0.5 ml, 10.41 mmol) in 30 ml of 1,4-dioxane was heated up to reflux at 105° C. for 24 hours. The reaction mixture was evaporated by vacuum to remove most of the solvent. The residue was purified by flash silica gel chromatography, eluted with $CH_2Cl_2$:MeOH (9:1) to afford (Xb) (1.91 g, 4.79 mmol, 69% yield) as a brown color grease.

TLC: $R_f$=0.4 ($CH_2Cl_2$:MeOH=9:1).

$^1$H-NMR ($CDCl_3$): δ 1.29–1.86(m, 10H), 3.28 (s, br, 2H, NH), 4.53–4.56(d, J=3 Hz, 1H), 4.83–4.89 (m, 1H), 5.28–5.46 (d, d, J=17, 13 Hz, 2H), 6.02–6.13 (m, 1H), 6.86–6.91 (m, 1H), 7.00–7.04 (m, 2H), 7.25–7.31 (m, 1H), 7.64 (s, 1H).

IR($CDCl_3$) 3330, 2936, 2859, 1726, 1635,1561, 1522, 1489, 1449, 1364, 1264, 1174, 1121, 1011, 930, 778, 695 $cm^{-1}$

MS Calcd for $C_{21}H_{26}N_4O_4$ (M+H)=399, observed (M+H)=399

HPLC: 5% $CH_3CN$/$H_2O$ (0.1% TFA) to 90% $CH_3CN$/$H_2O$ (0.1% TFA)/10 min.

Retention time=7.605 min.

Example 29

(3-Allyloxy-phenyl)-(4-oxo-1,4-dihydro-pyrazolo[3,4-d]pyrimidin-5-yl)-acetic acid cyclohexyl ester (XIb) ($R_1$ is 3-allyloxy-phenyl)

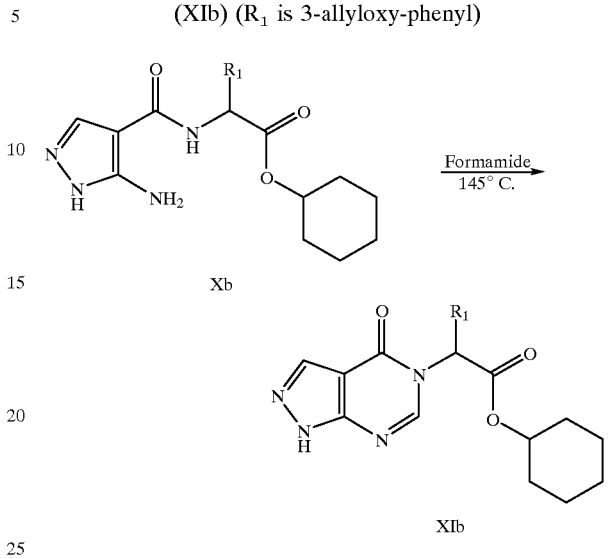

The reaction mixture of (Xb) (1.83 g, 4.59 mmol) in 30 ml of formamide was heated up to 145° C. overnight. After cooling to room temperature, the mixture was partitioned between EtOAc (200 ml) and saturated $NaHCO_3$ (3×75 ml), brine (75 ml). The organic layer was dried over $Na_2SO_4$, then evaporated by vacuum. The residue of yellow oil was purified by flash silica gel chromatography, eluted with $CH_2Cl_2$:EtOAc (1:1) to afford (XIb) (0.7 g, 1.31 mmol, 28% yield) as an off-white foam.

TLC: $R_f$=0.5 ($CH_2Cl_2$:EtOAc=1:1).

$^1$H-NMR ($CDCl_3$): δ 1.29–1.91(m, 10H), 4.55–4.57(d, J=7 Hz, 2H), 4.96–5.02 (m, 1H), 5.31–5.47 (d, d, J=11, 19 Hz, 2H), 602–6.13 (m, 1H), 6.78 (s, 1H), 6.89–7.02 (m, 3H), 7.30–7.41 (m, 1H), 7.91 (s, 1H), 8.22 (s, 1H), 11.01 (s, br, 1H, NH).

IR($CDCl_3$) 3225, 2934, 1734, 1700, 1653, 1558, 1489, 1363, 1196, 1120, 1012, 827, 703 $cm^{-1}$

MS Calcd for $C_{22}H_{24}N_5O_4$ (M+H)=409, observed (M+H)=409

HPLC: 5% $CH_3CN$/$H_2O$ (0.1% TFA) to 90% $CH_3CN$/$H_2O$ (0.1% TFA)/10 min.

Retention time=8.831 min.

Example 30

(3-Allyloxy-phenyl)-(4-thioxo-1,4-dihydro-pyrazolo[3,4-d]pyrimidin-5-yl)-acetic acid cyclohexyl ester (XIIb) ($R_1$ is 3-allyloxy-phenyl)

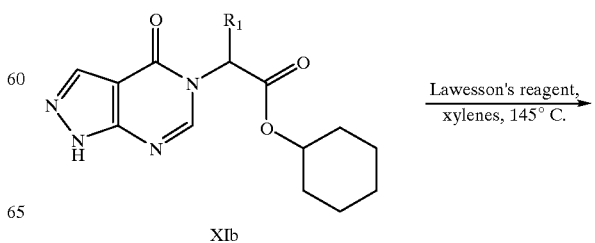

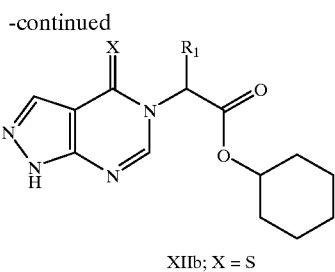

XIIb; X = S

A solution of (XIb) (0.68 g, 1.65 mmol) in 20 ml of xylene was purged with argon for 20 minutes, to which Lawesson's reagent (0.67 g, 1.65 mmol) was added. The resulting mixture heated at 145° C. for 2 h under argon. The reaction mixture was concentrated under vacuum to remove some of xylene. The residue was chromatographed using silica gel and eluted with hexanes to remove the front fraction (the remaining xylene) and then eluted with hexanes:EtOAc/2:1 to collect the desired fraction to afford (XIIb) (0.5 g, 1.17 mmol, 71% yield) as an off-white foam.

TLC: $R_f$=0.2 (Hexanes:EtOAc=2:1).

$^1$H-NMR (CDCl$_3$) δ 1.27–1.91 (m, 10H), 4.56–4.57 (d, J=3 Hz, 2H), 5.00–5.05 (m, 1H), 5.31–5.47 (d, d, J=18, 20 Hz, 2H), 5.99–6.10 (m, 1H), 6.94–7.03 (m, 3H), 7.36–7.42 (m, 1H), 7.70–8.06 (d, J=7 Hz, 1H, ), 8.38 (s, 1H).

IR(CDCl$_3$) 3425, 2934, 1734, 1596, 1558, 1498, 1456, 1362, 1261, 1205, 1009, 907 cm$^{-1}$

MS Calcd for $C_{22}H_{24}N_4O_3S$ (M+H)=425, observed (M+H)=425;

HPLC: 30% CH$_3$CN/H$_2$O (0.1% TFA) to 90% CH$_3$CN/H$_2$O (0.1% TFA)/10 min.

Retention time=9.14 min.

Example 31

(3-Alyloxy-phenyl-(4-thioxo-1,4-dihydro-pyrazolo [3,4-d]pyrimidin-5-yl)acetic acid (XIVb) (R$_1$ is 3-allyloxy-phenyl)

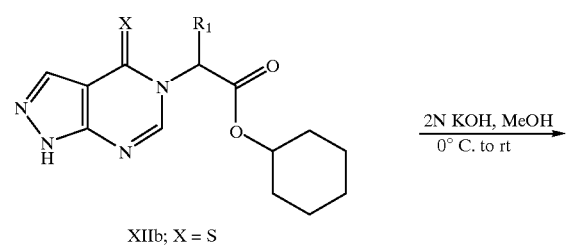

XIIb; X = S

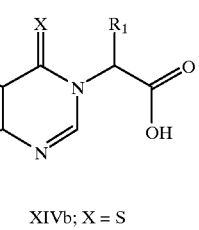

XIVb; X = S

2N KOH aqueous solution (0.9 ml, 1.77 mmol) was added to a solution of (3-allyloxy-phenyl)-(4-thioxo-1,4-dihydro-pyrazolo[3,4-d]pyrimidin-5-yl)acetic acid cyclohexyl ester (XIIb) (0.38 g, 0.88 mmol) in 10 ml of methanol at 0° C. The resulting mixture of yellow solution was stirred overnight at 0° C. to room temperature. The reaction mixture was concentrated by vacuum to remove most of the methanol, and water (20 ml) was added. The pH was adjusted to 4.0 with aqueous 10% citric acid solution. The product was extracted with EtOAc (2×150 ml). The combined organic layer was washed with water, brine (2×30 ml) and dried over anhydrous Na$_2$SO$_4$, then concentrated by vacuum to afford (XIVb) (0.29 g, 0.84 mmol, 95% yield) as a yellowish solid.

mp: 85–90° C.

TLC; $R_f$=0.1 (CH$_2$Cl$_2$:MeOH 9:1).

$^1$H-NMR; (CD$_3$OD) δ 4.54–4.56 (d, J=5 Hz, 2H), 5.30–5.46 (d, d, J=11, 12 Hz, 2H), 5.99–6.08 (m, 1H), 6.94–7.04 (m, 2H), 7.30–7.62 (m, 3H), 8.02–8.10 (d, J=15 Hz, 1H), 8.36 (s, 1H).

IR(CDCl$_3$) 3425, 2980, 1717, 1598, 1558, 1490, 1362, 1207 cm$^{-1}$

MS Calcd for $C_{16}H_{14}N_4O_3S$ (M+H)=343, observed (M+H)=343;

HPLC: 5% CH$_3$CN/H$_2$O (0.1% TFA) to 90% CH$_3$CN/H$_2$O (0.1% TFA)/10 min.

Retention time=6.728 min.

Example 32

(5-(1-Phenyl-ethyl)-1,5-dihydro-pyrazolo[3,4-d]pyrimidine-4-one) (LVIIa) (R$_1$=phenyl; R$_8$=Me)

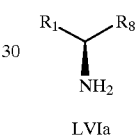
LVIa

1. Triethyl orthoformate, p-TsOH, 105° C.
2. Ethyl 3-amino-4-pyrazole carboxylate, p-TsOH, xylene, 155° C.

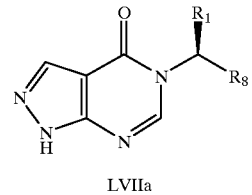
LVIIa p-TsOH was added to a mixture of (R)-α-methyl benzylamine (0.52 ml, 4.0 mmol) in triethyl orthoformate (5.3 ml, 32 mmol) and the resulting mixture was refluxed at 155° C. for 4 hours. The excess triethyl orthoformate was distilled under reduced pressure at 80° C. The residual yellow oil was azeotroped with toluene (3×15 ml) and concentrated under vacuum to give a pale yellow oil. To the crude oil was added 10 ml of xylene, ethyl 3-amino-4-pyrazole carboxylate (0.31 g, 2 mmol) and p-TsOH (76 mg, 0.4 mmol) and the result refluxed for 24 hours. The reaction was cooled to room temperature, extracted with 2×30 ml of 2N NaOH. The combined aqueous layers were acidified to pH=5 with conc. HCl. The precipitated solid was filtered off and washed well with water, dried under high vacuum to yield 181 mg of LVIIa as a white solid in 38% yield.

mp: 210–214° C.

TLC; $R_f$=0.2 (Hexane:EtOAc=1:1)

$^1$H-NMR; (CDCl$_3$) δ 1.85–1.87 (d, J=7 Hz, 3H), 6.42–6.45 (q, 1H), 7.37–7.44 (m, 5H), 7.94 (s, 1H), 8.24 (s, 1H).

MS Calcd. for $C_{13}H_{12}N_4O$ (M+H)=241, observed (M+H)=241;

EA Calcd. for $C_{13}H_{12}N_4O$. 0.5 H2O=C: 64.26; H: 5.1; N: 23.06

Observed=C: 64.22; H: 5.02; N: 23.04

HPLC: 5% $CH_3CN/H_2O$ (0.1% TFA) to 90% $CH_3CN/H_2O$ (0.1% TFA)/20 min.

Retention time=7.5 min.

Example 33

(5-(1-Phenyl-ethyl)-1,5-dihydro-pyrazolo[3,4-d]pyrimidine-4-thione) (LVIIIa) ($R_1$=phenyl; $R_8$=Me)

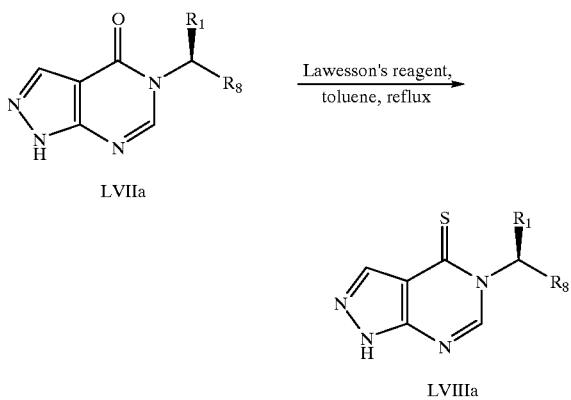

A reaction mixture of LVIIa (0.1 g, 0.42 mmol) and Lawesson's reagent (0.101 g, 0.25 mmol) in 5 ml of toluene was refluxed for 5 hours. The yellow reaction mixture was cooled to room temperature and the solvent removed under reduced pressure. The resulting yellow oil was column chromatographed on silica gel using $CH_2Cl_2$:EtOAc::1:1 (120 ml) followed by CHCl3:EtOAc::1:1 to yield LVIIIa (0.101 g, 0.39 mmol) as a white solid in 95% yield.

mp: 170–174° C.

TLC; $R_f$=0.65 ($CH_2Cl_2$:EtOAc=1:1)

$^1$H-NMR; ($CDCl_3$) δ 1.87–1.9 (d, J=7 Hz, 3H), 7.39–7.44 (m, 5H), 7.55–7.57 (q, 1H), 8.01 (s, 1H), 8.41 (s, 1H).

MS Calcd. for $C_{13}H_{12}N_4S$ (M+H)=257, observed (M+H)=257;

EA Calcd. for $C_{13}H_{12}N_4S$. 0.07 Hexane=C: 61.47; H: 5.01; N: 21.32; S: 12.2

Observed=C: 61.55; H: 4.99; N: 21.05; S: 12.23

HPLC: 5% $CH_3CN/H_2O$ (0.1% TFA) to 90% $CH_3CN/H_2O$ (0.1% TFA)/20 min.

Retention time=11.5 min.

The exemplary compounds described above may be tested for their activity as described below.

Biological Testing: ERAB Enzyme Assay

The activity of ERAB (L-3-hydroxyacyl-CoA dehydrogenase) in the reverse direction was determined by a modified version of a method previously described (Binstock et al., Methods Enzymol., 71, 403–411 (1981)). This method is based on the enzyme-catalyzed loss of NADH absorbance at 340 nm with a change in the millimolar extinction coefficient of 6.22 $mM^{-1}$ $cm^{-1}$. The $IC_{50}$ value for compounds of the Formula I were determined spectrophotometrically by monitoring the reduction of NADH to $NAD^+$ with acetoacetyl-CoA as substrate and are reported in Table 1. Assay conditions were 25 mM MOPS, 250 mM NaCl, 2% DMSO, 2.5 mM TCEP, pH 7.5, 30° C. NADH and ERAB were included at 40 uM and 2.5 nM, respectively. Stock solutions of ERAB, prepared in assay buffer, were 1 uM and contained 100 uM NADH for enzyme stability. The assay was run as follows: Enzyme (2.5 nM) was preincubated with inhibitor (without acetoacetyl-CoA present) for 400 seconds at 30° C. in the presence of 36 uM NADH, 25 mM MOPS, pH 7.5, 250 mM NaCl, 2%(v/v) DMSO, and 2.5 mM TCEP. The reaction was initiated by addition of substrate (acetoacetyl-CoA) (38 uM). Reduction of NADH was monitored at 340λ. Initial rates were calculated over a time frame where less than 10% of substrates had been consumed in an uninhibited reaction. For Ki, app determination, inhibitors were added during the preincubation stage from DMSO stock solutions for a final and constant 2% DMSO concentration. Initial rates were calculated and fitted, using non-linear fitting techniques, to the Michaelis equation for enzyme inhibition. The $IC_{50}$ value was determined by non-linear regression analysis using KaleidaGraph (obtained from Synergy Software, Reading, Pa.).

TABLE 1

| MOL STRUCTURE | COMPOUND NO. | MOLECULAR WEIGHT | $IC_{50}$ UNITS |
|---|---|---|---|
| $IC_{50}$ For ERAB OR HADH2 INHIBITING AGENTS | | | |
|  | XVIa | 367.475 | 0.097 μM |

TABLE 1-continued
IC$_{50}$ For ERAB OR HADH2 INHIBITING AGENTS
| MOL STRUCTURE | COMPOUND NO. | MOLECULAR WEIGHT | IC$_{50}$ UNITS |
|---|---|---|---|
| 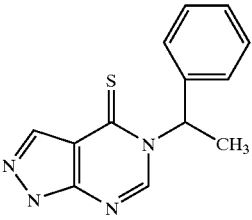 | LVIIIa | 256.332 | 22 μM |
| 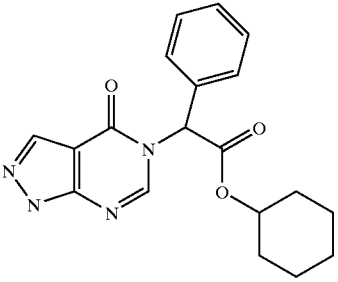 | XIa | 352.392 | 30 μM |
| 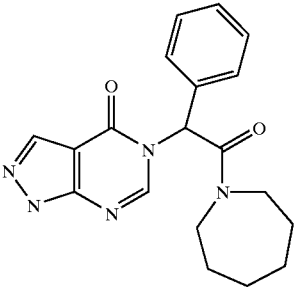 | L | 351.408 | 7.1 μM |
| 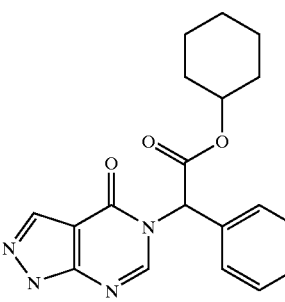 | XIIa | 368.459 | 1.2 μM |
| 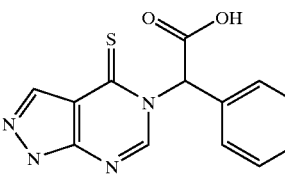 | XIVa | 286.314 | 514 μM |

TABLE 1-continued

IC₅₀ For ERAB OR HADH2 INHIBITING AGENTS

| MOL STRUCTURE | COMPOUND NO. | MOLECULAR WEIGHT | IC$_{50}$ UNITS |
| --- | --- | --- | --- |
|  | XVIe | 381.502 | 0.096 μM |
|  | XXVa | 353.448 | 0.774 μM |
|  | XVIb | 329.383 | 1.5 μM |
|  | XVIc | 369.447 | 1.8 μM |
|  | XXVb | 429.546 | 0.216 μM |

TABLE 1-continued

IC$_{50}$ For ERAB OR HADH2 INHIBITING AGENTS

| MOL STRUCTURE | COMPOUND NO. | MOLECULAR WEIGHT | IC$_{50}$ UNITS |
|---|---|---|---|
| (structure) | XVIg | 524.441 | 0.082 μM |
| (structure) | XVIf | 445.545 | 0.081 μM |
| (structure) | XVIh | 471.582 | 0.766 μM |
| (structure) | XVIi | 431.522 | 0.389 μM |
| (structure) | XVIj | 430.534 | 0.218 μM |

TABLE 1-continued

IC$_{50}$ For ERAB OR HADH2 INHIBITING AGENTS

| MOL STRUCTURE | COMPOUND NO. | MOLECULAR WEIGHT | IC$_{50}$ UNITS |
| --- | --- | --- | --- |
| | XVIk | 460.56 | 0.3 μM |
| | XVIm | 446.533 | 0.279 μM |
| | XXVc | 383.474 | 0.051 μM |
| | XVIq | 355.464 | 2.8 μM |

TABLE 1-continued

IC$_{50}$ For ERAB OR HADH2 INHIBITING AGENTS

| MOL STRUCTURE | COMPOUND NO. | MOLECULAR WEIGHT | IC$_{50}$ UNITS |
|---|---|---|---|
| | XXVd | 425.554 | 0.071 μM |
| | XVIr | 341.437 | 0.093 μM |
| | XXVe | 375.454 | 0.749 μM |
| | XVIp | 383.474 | 0.21 μM |
| | XVIs | 501.608 | 0.406 μM |

TABLE 1-continued

IC$_{50}$ For ERAB OR HADH2 INHIBITING AGENTS

| MOL STRUCTURE | COMPOUND NO. | MOLECULAR WEIGHT | IC$_{50}$ UNITS |
|---|---|---|---|
| | XVIt | 423.539 | 0.345 μM |
| | XVIb | 342.378 | |
| | XXIII | 424.523 | 11 μM |
| | LVII | 240.265 | 494 μM |

What is claimed is:

1. A compound represented by the formula I:

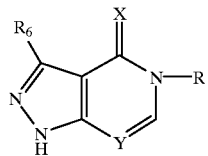

(I)

wherein:

X is O or S;

Y is N or CH;

R$_6$ is H or OH; and

R is

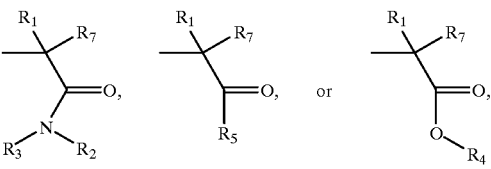

wherein:

R$_1$ is hydrogen or an alkyl, alkenyl, alkynyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO$_2$, —N—OH, N—OR$_c$, —CN, —(CH$_2$)$_z$—CN where z is an integer from 0 to 4, halogen, —OH, —O—R$_a$—

O—, —OR$_b$, —CO—R$_c$, O—CO—R$_c$, —CO—OR$_c$, —O—CO—OR$_c$, —O—CO—O—CO—R$_c$, —O—OR$_c$, =O, =S, SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, NR$_c$—CO—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, CO—SO$_2$—R$_c$, —CS—R$_c$, —CSO—R$_c$, —CSO$_2$—R$_c$, —NR$_c$CS—R$_d$, —O—CS—R$_c$, —O—CSO—R$_c$, O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, NR$_c$—CS—R$_d$, —SH, —S—R$_b$, and —PO$_2$—OR$_c$, where R$_a$ is selected from the group consisting of alkyl, heteroalkyl, alkenyl, aryl, heteroaryl, and alkynyl, R$_b$ is selected from the group consisting of alkyl, heteroalkyl, haloalkyl, alkenyl, alkynyl, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$ are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —CN, —(CH$_2$)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above;

R$_2$ and R$_3$ are each independently hydrogen or an alkyl, alkenyl, alkoxy, aryl, heteroaryl, cycloalkyl, or heterocycloalkyl group, or R$_2$ and R$_3$ together with the N atom to which they are attached form a 4- to 10-membered heterocycloalkyl or heteroaryl group containing at least one N, S or O heteroatom, where the alkyl, alkenyl, alkoxy, aryl, heteroaryl, cycloalkyl, or heterocycloalkyl group is unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO$_2$, —N—OH, N—OR$_c$, —CN, —(CH$_2$)$_z$—CN where z is an integer from 0 to 4, halogen, —OH, —O—R$_a$—O—, —OR$_b$, —CO—R$_c$, O—CO—R$_c$, CO—OR$_c$, —O—CO—OR$_c$, —O—CO—O—CO—R$_c$, —O—OR$_c$, =O, =S, SO$_2$R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, NR$_c$—CO—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, NR$_c$—CS—R$_d$, —SH, —S—R$_b$, and —PO$_2$—OR$_c$, where R$_a$ is selected from the group consisting of alkyl, heteroalkyl, alkenyl, and alkynyl, R$_b$ is selected from the group consisting of alkyl, heteroalkyl, haloalkyl, alkenyl, alkynyl, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$ are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —CN, —(CH$_2$)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above;

R$_4$ is hydrogen or an alkyl, alkenyl, cycloalkyl, heterocycloalkyl, aryl or heteroaryl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO$_2$, —N—OH, N—OR$_c$, —CN, —(CH$_2$)$_z$—CN where z is an integer from 0 to 4, halogen, —OH, —O—R$_a$—O—, —OR$_b$, —CO—R$_c$, O—CO—R$_c$, —CO—OR$_c$, —O—CO—OR$_c$, —O—CO—O—CO—R$_c$, —O—OR$_c$, =O, =S, SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, NR$_c$—CO—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, NR$_c$—CS—R$_d$, —SH, —S—R$_b$, and —PO$_2$—OR$_c$, where R$_a$ is selected from the group consisting of alkyl, heteroalkyl, alkenyl, aryl, heteroaryl, and alkynyl, R$_b$ is selected from the group consisting of alkyl, heteroalkyl, haloalkyl, alkenyl, alkynyl, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$ are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —CN, —(CH$_2$)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above;

R$_5$ is hydrogen or an alkyl, alkenyl, alkynyl, cycloalkyl, heterocycloalkyl, aryl or heteroaryl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO$_2$, —N—OH, N—OR$_c$, —CN, —(CH$_2$)$_z$—CN where z is an integer from 0 to 4, halogen, —OH, —O—R$_a$—O—, —OR$_b$, —CO—R$_c$, O—CO—R$_c$, —CO—OR$_c$, —O—CO—R$_c$, —CO—OR$_c$, —O—CO—OR$_c$, —O—CO—O—CO—R$_c$, —O—OR$_c$, =O, =S, SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, NR$_c$—CO—OR$_e$, —CO—NR$_c$—CO—R$_c$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, O—CSO$_2$—R$_c$, —SO$_2$—NR$_d$R$_e$, —SO—NR$_d$R$_e$, —S—NR$_d$R$_e$, —NR$_c$—CSO$_2$—R$_d$, —NR$_c$—CSO—R$_d$, NR$_c$—CS—R$_d$, —SH, —S—R$_b$, and —PO$_2$—OR$_c$, where R$_a$ is selected from the group consisting of alkyl, heteroalkyl, alkenyl, aryl, heteroaryl, and alkynyl, R$_b$ is selected from the group consisting of alkyl, heteroalkyl, haloalkyl, alkenyl, alkynyl, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$, are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —CN, —(CH$_2$)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above; and R$_7$ is hydrogen or a C$_1$–C$_3$ alkyl, hydroxy or C$_1$–C$_3$ alkoxy group;

or a pharmaceutically acceptable salt thereof.

2. A compound or pharmaceutically acceptable salt according to claim 1, wherein:

R is

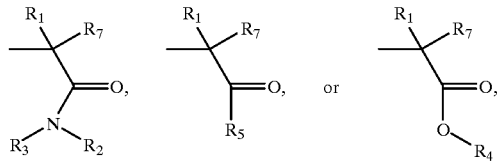

wherein:

R$_1$ is an aryl or heteroaryl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO$_2$, —N—OH, N—OR$_c$, —CN, —(CH$_2$)$_z$—CN where z is an integer from 0 to 4, halogen, —OH, —O—R$_a$—O—, —OR$_b$, —CO—R$_c$, O—CO—R$_c$, —CO—OR$_c$, —O—CO—OR$_c$, —O—CO—O—CO—R$_c$, —O—OR$_c$, =O, =S, SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, NR$_c$—CO—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, NR$_c$—CS—R$_d$, —SH, —S—R$_b$, and —PO$_2$—OR$_c$, where R$_a$ is selected from the group consisting of alkyl, heteroalkyl, alkenyl, aryl, heteroaryl, and alkynyl, R$_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;

$R_2$ and $R_3$ are each independently hydrogen or an alkyl, alkenyl, alkoxy, aryl, heteroaryl, cycloalkyl, or heterocycloalkyl group, or $R_2$ and $R_3$ together with the N atom to which they are attached form a 4- to 10-membered heterocycloalkyl or heteroaryl group containing at least one N, S or O heteroatom, where the alkyl, alkenyl, alkoxy, aryl, heteroaryl, cycloalkyl, or heterocycloalkyl group is unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—R, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;

$R_4$ is hydrogen or an alkyl, alkenyl, cycloalkyl, heterocycloalkyl, aryl or heteroaryl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—R, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —(CH$_2$)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above;

R$_5$ is hydrogen or an alkyl, alkenyl, alkynyl, cycloalkyl, heterocycloalkyl, aryl or heteroaryl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO$_2$, —N—OH, N—OR$_c$, —CN, —(CH$_2$)$_z$—CN where z is an integer from 0 to 4, halogen, —OH, —O—R$_a$—O—, —OR$_b$, —CO—R$_c$, O—CO—R$_c$, —CO—OR$_c$, —O—CO—OR$_c$, —O—CO—O—CO—R$_c$, —O—OR$_c$, =O, =S, SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, NR$_c$—CO—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, NR$_c$—CS—R$_d$, —SH, —S—R$_b$, and —PO$_2$—OR$_c$, where R$_a$ is selected from the group consisting of alkyl, heteroalkyl, alkenyl, aryl, heteroaryl, and alkynyl, R$_b$ is selected from the group consisting of alkyl, heteroalkyl, haloalkyl, alkenyl, alkynyl, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$ are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —CN, —(CH$_2$)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above; and R$_7$ is hydrogen or a C$_1$–C$_3$ alkyl, hydroxy or C$_1$–C$_3$ alkoxy group.

3. A compound or pharmaceutically acceptable salt according to claim 2, wherein R is

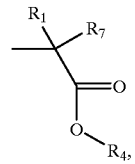

and wherein R$_4$ is hydrogen or an alkyl or cycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO$_2$, —N—OH, N—OR$_c$, —CN, —(CH$_2$)$_z$—CN where z is an integer from 0 to 4, halogen, —OH, —O—R$_a$—O—, —OR$_b$, —CO—R$_c$, O—CO—R$_c$, —CO—OR$_c$, —O—CO—OR$_c$, —O—CO—O—CO—R$_c$, —O—OR$_c$, =O, =S, SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, NR$_c$—CO—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, O—CSO$_2$—R$_c$, —SO$_2$—NR$_d$R$_e$—SO—NR$_d$R$_e$, —S—NR$_d$R$_e$, —NR$_d$—CSO$_2$—R$_d$, —NR$_c$—CSO—R$_d$, NR$_c$—CS—R$_d$, —SH, —S—R$_b$, and —PO$_2$—OR$_c$, where R$_a$ is selected from the group consisting of alkyl, heteroalkyl, alkenyl, aryl, heteroaryl, and alkynyl, R$_b$ is selected from the group consisting of alkyl, heteroalkyl, haloalkyl, alkenyl, alkynyl, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$ are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —CN, —(CH$_2$)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above.

4. A compound or pharmaceutically acceptable salt according to claim 2, wherein R is

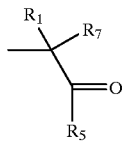

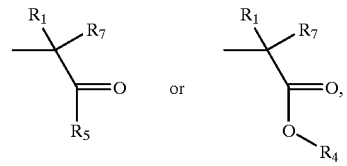

and wherein wherein $R_5$ is an alkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_d$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above.

5. A compound or pharmaceutically acceptable salt according to claim 2, wherein $R_7$ is hydrogen.

6. A compound or pharmaceutically acceptable salt according to claim 2, wherein R is and wherein $R_4$ is hydrogen or an alkyl or cycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;

$R_5$ is an alkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above; and $R_7$ is hydrogen.

7. A compound represented by the formula I:

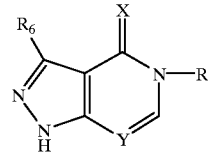

(I)

wherein:

X is O or S;

Y is N or CH;

$R_6$ is H or OH; and

R is

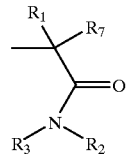

wherein:

$R_1$ is hydrogen or an alkyl, alkenyl, alkynyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;

$R_7$ is hydrogen, or a $C_1$–$C_3$ alkyl, hydroxy or $C_1$–$C_3$ alkoxy group; and $R_2$ and $R_3$ are each independently hydrogen or an alkyl, alkenyl, alkoxy, aryl, heteroaryl, cycloalkyl, or heterocycloalkyl group, or $R_2$ and $R_3$ together with the N atom to which they are attached form a 4- to 10-membered heterocycloalkyl or heteroaryl group containing at least one N, S or O heteroatom, where the alkyl, alkenyl, alkoxy, aryl, heteroaryl, cycloalkyl, or heterocycloalkyl group is unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—$CSO$—$R_d$, $NR_c$—CS—$R_d$, —SH, —S—$R_b$, and—$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above.

or a pharmaceutically acceptable salt thereof.

8. A compound or pharmaceutically acceptable salt according to claim 7, wherein $R_1$ is an aryl or heteroaryl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—$CSO$—$R_d$, $NR_c$—CS—$R_d$, —SH, —S—$R_b$, and—$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above.

9. A compound or pharmaceutically acceptable salt according to claim 7, wherein $R_7$ is hydrogen.

10. A compound or pharmaceutically acceptable salt according to claim 7, wherein $R_2$ and $R_3$ are each independently an alkyl, alkoxy or aryl group, or $R_2$ and $R_3$ together with the N atom to which they are attached form a 4- to 10-membered heterocycloalkyl or heteroaryl group containing at least one N, S or O heteroatom, where the alkyl, alkoxy, aryl or heterocycloalkyl group is unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—

$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, —O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, allynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above.

11. A compound or pharmaceutically acceptable salt according to claim 7, wherein $R_1$ is an aryl or heteroaryl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;

$R_7$ is hydrogen; and $R_2$ and $R_3$ are each independently an alkyl, alkoxy or aryl group, or $R_2$ and $R_3$ together with the N atom to which they are attached form a 4- to 10-membered heterocycloalkyl or heteroaryl group containing at least one N, S or O heteroatom, where the alkyl, alkoxy, aryl or heterocycloalkyl group is unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —(CH₂)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above.

12. A compound or pharmaceutically acceptable salt according to claim 10, wherein R$_2$ and R$_3$ together with the N atom to which they are attached form

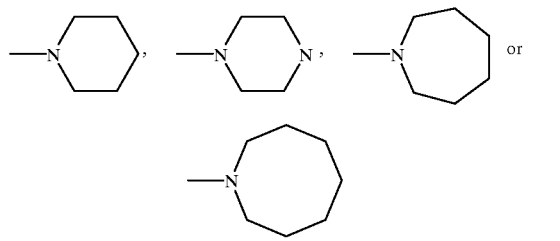

unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO₂, —N—OH, N—OR$_c$, —CN, —(CH₂)$_z$— CN where z is an integer from 0 to 4, halogen, —OH, —O—R$_a$—O—, —OR$_b$, —CO—R$_c$, O—CO—R$_c$, —CO— OR$_c$, —O—CO—OR$_c$, —O—CO—O—CO—R$_c$, —O—OR$_c$, =O, =S, SO₂—R$_c$, —SO—R$_c$, —NR$_d$R$_e$, —CO—NR$_d$R$_e$, —O—CO—NR$_d$R$_e$, —NR$_c$—CO— NR$_d$R$_e$, —NR$_c$—CO—R$_e$, NR$_c$—CO—OR$_e$, —CO— NR$_c$—CO—R$_d$, —O—SO₂—R$_c$, —O—SO—R$_c$, —O—S—R$_c$, —S—CO—R$_c$, —SO—CO—OR$_c$, —SO₂— CO—OR$_c$, —O—SO₃, —NR$_c$—SR$_d$, —NR$_c$—SO—R$_d$ NR$_c$—SO₂—R$_d$, —CO—SR$_c$, —CO—SO—R$_c$, CO—SO₂—R$_c$, —CS—R$_c$, —CSO—R$_c$, —CSO₂—R$_c$, —NR$_c$CS—R$_d$, —O—CS—R$_c$, —O—CSO—R$_c$, O—CSO₂—R$_c$, —SO₂—NR$_d$R$_e$, —SO—NR$_d$R$_e$, —S—NR$_d$R$_e$, —NR$_d$—CSO₂—R$_d$, —NR$_c$—CSO—R$_d$, NR$_c$—CS—R$_d$, —SH, —S—R$_b$, and —PO₂—OR$_c$, where R$_a$ is selected from the group consisting of alkyl, heteroalkyl, alkenyl, aryl, heteroaryl, and alkynyl, R$_b$ is selected from the group consisting of alkyl, heteroalkyl, haloalkyl, alkenyl, alkynyl, —CO—R$_c$, —CO—OR$_e$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$ are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO₂, —CN, —(CH₂)$_z$ —CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO— NR$_d$R$_e$, —C—CO—OR$_c$, —NR$_c$—CO—R$_d$, —O—CO— O—R$_c$, O—CO—NR$_d$R$_e$, —SH, —O—R$_b$, —O—R$_a$— O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above.

13. A compound or pharmaceutically acceptable salt according to claim 12, wherein the N-heterocycloalkyl group is substituted with one or more substituents independently selected from the group consisting of hydroxy, alkyl, —CO-alkyl, aryl, heteroaryl, cycloalkyl or heterocycloalkyl, and wherein the alkyl, aryl or heteroaryl group is unsubstituted or substituted with one or more substituents independently selected from the group consisting of halogen, hydroxy, alkoxy or allyloxy.

14. A compound represented by the formula I:

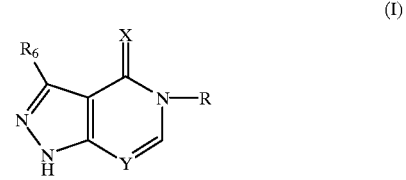

(I)

wherein:
X is O or S;
Y is N or CH;
R$_6$ is H or OH;
R is

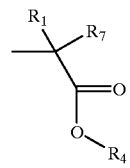

wherein:
R$_1$ is hydrogen or an alkyl, alkenyl, alkynyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO₂, —N—OH, N—OR$_c$, —CN, —(CH₂)$_z$—CN where z is an integer from 0 to 4, halogen, —OH, —O—R$_a$— O—, —OR$_b$, —CO—R$_c$, O—CO—R$_c$, —CO— OR$_c$, —O—CO—OR$_c$, —O—CO—O—CO—R$_c$, —O—OR$_c$, =O, =S, SO₂—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$CO—R$_e$, NR$_c$— CO—OR$_e$, —CO—NR$_c$—CO—R$_d$, —O—SO₂— R$_c$, —O—SO—R$_c$, —O—S—R$_c$, —S—CO—R$_c$, —SO—CO—OR$_c$, —SO₂—CO—OR$_c$, —O—SO₃, —NR$_c$—SR$_d$, —NR$_c$—SO—R$_d$, NR$_c$—SO₂—R$_d$, —CO—SR$_c$, —CO—SO—R$_c$, CO—SO₂—R$_c$, —CS—R$_c$, —CSO—R$_c$, —CSO₂—R$_c$, —NR$_c$CS—R$_d$, —O—CS—R$_c$, —O—CSO—R$_c$, O—CSO₂—R$_c$, —SO₂— NR$_d$R$_e$, —SO—NR$_d$R$_e$, —S—NR$_d$R$_e$, —NR$_d$— CSO₂—R$_d$, —NR$_c$—CSO—R$_d$, NR$_c$—CS—R$_d$, —SH, —S—R$_b$, and —PO₂—OR$_c$, where R$_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—O$R_c$, —O—CO—O—$R_c$, —O—CO—$R_c$, —NR$_c$—CO—$R_d$, —CO—NR$_d$R$_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —COR$_f$, —COOR$_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —(CH$_2$)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_c$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;

$R_7$ is hydrogen or a $C_1$–$C_3$ alkyl, hydroxy or $C_1$–$C_3$ alkoxy group; and $R_4$ is hydrogen or an alkyl, alkenyl, cycloalkyl, heterocycloalkyl, aryl or heteroaryl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO$_2$, —N—OH, N—OR$_c$, —CN, —(CH$_2$)$_z$—CN where z is an integer from 0 to 4, halogen, —OH, —O—R$_a$—O—, —OR$_b$, —CO—R$_c$, O—CO—R$_c$, —CO—OR$_c$, —O—CO—OR$_c$, —O—CO—O—CO—R$_c$, —O—OR$_c$, =O, =S, SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, NR$_c$—CO—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, NR$_c$—CS—R$_d$, —SH, —S—R$_b$, and—PO$_2$—OR$_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$ are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —CN, —(CH$_2$)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above; or a pharmaceutically acceptable salt thereof.

15. A compound or pharmaceutically acceptable salt according to claim 14, wherein $R_1$ is an aryl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO$_2$, —N—OH, N—OR$_c$, —CN, —(CH$_2$)$_z$—CN where z is an integer from 0 to 4, halogen, —OH, —O—R$_a$—O—, —OR$_b$, —CO—R$_c$, O—CO—R$_c$, —CO—OR$_c$, —O—CO—OR$_c$, —O—CO—O—CO—R$_c$, —O—OR$_c$, =O, =S, SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, NR$_c$—CO—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, NR$_c$—CS—R$_d$, —SH, —S—R$_b$, and—PO$_2$—OR$_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$ are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —CN, —(CH$_2$)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—

O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above.

16. A compound or pharmaceutically acceptable salt according to claim 14, wherein $R_7$ is hydrogen.

17. A compound or pharmaceutically acceptable salt according to claim 14, wherein $R_4$ is hydrogen or a cycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above.

18. A compound or pharmaceutically acceptable salt according to claim 14, wherein $R_1$ is an aryl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;

$R_7$ is hydrogen; and $R_4$ is hydrogen or a cycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above.

19. A compound represented by the formula I:

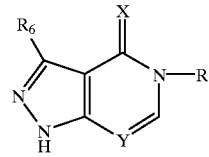

(I)

wherein:

X is O or S;

Y is CH;

$R_6$ is H or OH;

R is

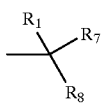

wherein:

$R_1$ is hydrogen or an alkyl, alkenyl, alkynyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$NR_dR_e$, —$NR_c$—CO—$R_e$, NR_c— CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;

$R_7$ is hydrogen or a $C_1$–$C_3$ alkyl, hydroxy or $C_1$–$C_3$ alkoxy group; and $R_8$ is hydrogen or an alkyl, alkenyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —PO₂—OR$_c$, where alkyl, heteroalkyl, alkenyl, and alkynyl, R$_b$ is selected from the group consisting of alkyl, heteroalkyl, haloalkyl, alkenyl, alkynyl, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$ are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO₂, —CN, —(CH₂)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above; or a pharmaceutically acceptable salt thereof.

20. A compound represented by the formula I:

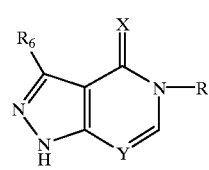

(I)

wherein:
X is O or S;
Y is N;
R$_6$ is OH;
R is

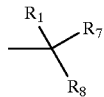

wherein:
R$_1$ is hydrogen or an alkyl, alkenyl, alkynyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO₂, —N—OH, N—OR$_c$, —CN, —(CH₂)$_z$—CN where z is an integer from 0 to 4, halogen, —OH, —O—R$_a$—O—, —OR$_b$, —CO—R$_c$, O—CO—R$_c$, —CO—OR$_c$, —O—CO—OR$_c$, —O—CO—O—CO—R$_c$, —O—OR$_c$, =O, =S, SO₂—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, NR$_c$—CO—OR$_e$, —CO—NR$_c$—CO—R$_d$, —O—SO₂—R$_c$, —O—SO—R$_c$, —O—S—R$_c$, —S—CO—R$_c$, —SO—CO—OR$_c$, —SO₂—CO—OR$_c$, —O—SO₃, —NR$_c$—SR$_d$, —NR$_c$—SO—R$_d$, NR$_c$—SO₂—R$_d$, —CO—SR$_d$, —CO—SO—R$_c$, CO—SO₂—R$_c$, —CS—R$_c$, —CSO—R$_c$, —CSO₂—R$_c$, —NR$_c$—CS—R$_d$, —O—CS—R$_c$, —O—CSO—R$_c$, O—CSO₂—R$_c$, —SO₂—NR$_d$R$_e$—SO—NR$_d$R$_e$, —S—NR$_d$R$_e$, —NR$_d$—CSO₂—R$_d$, —NR$_c$—CSO—R$_d$, NR$_c$—CS—R$_d$, —SH, —S—R$_b$, and —PO₂—OR$_d$, where R$_a$ is selected from the group consisting of alkyl, heteroalkyl, alkenyl, aryl, heteroaryl, and alkynyl, R$_b$ is selected from the group consisting of alkyl, heteroalkyl, haloalkyl, alkenyl, alkynyl, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$ are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be farther substituted with one or more substituents independently selected from the group consisting of NO₂, —CN, —(CH₂)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above;

R$_7$ is hydrogen or a C$_1$-C$_3$ alkyl, hydroxy or C$_1$-C$_3$ alkoxy group; and R$_8$ is hydrogen or an alkyl, alkenyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO₂, —N—OH, N—OR$_c$, —CN, —(CH₂)$_z$—CN where z is an integer from 0 to 4, halogen, —OH, —O—R$_a$—O—, —OR$_b$, —CO—R$_c$, O—CO—R$_c$, —CO—OR$_c$, —O—CO—OR$_c$, —O—CO—O—CO—R$_c$, —O—OR$_c$, =O, =S, SO₂—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, NR$_c$—CO—OR$_e$, —CO—NR$_c$—CO—R$_d$, —O—SO₂—R$_c$, —O—SO—R$_c$, —O—S—R$_c$, —S—CO—R$_c$, —SO—CO—OR$_c$, —SO₂—CO—OR$_c$, —O—SO₃, —NR$_c$—SR$_d$, —NR$_c$—SO—R$_d$, NR$_c$—SO₂—R$_d$, —CO—SR$_d$, —CO—SO—R$_c$, CO—SO₂—R$_c$, —CS—R$_c$, —CSO—R$_c$, —CSO₂—R$_c$, —NR$_c$—CS—R$_d$, —O—CS—R$_c$, —O—CSO—R$_c$, O—CSO₂—R$_c$, —SO₂—NR$_d$R$_e$, —SO—NR$_d$R$_e$, —S—NR$_d$R$_e$, —NR$_d$—CSO$_2$—R$_d$, —NR$_c$—CSO—R$_d$, NR$_c$—CS—R$_d$, —SH, —S—R$_b$, and —PO$_2$—OR$_c$, where alkyl, heteroalkyl, alkenyl, and alkynyl, R$_b$ is selected from the group consisting of alkyl, heteroalkyl, haloalkyl, alkenyl, alkynyl, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$ are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —CN, —(CH$_2$)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above; or a pharmaceutically acceptable salt thereof.

21. A compound represented by the formula I:

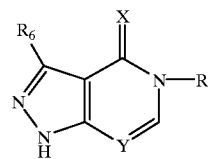

(I)

wherein:
X is S;
Y is N;
R$_6$ is H or OH;
R is

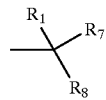

wherein:
R$_1$ is an alkyl, alkenyl, alkynyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO$_2$, —N—OH, N—OR$_c$, —CN, —(CH$_2$)$_z$—CN where z is an integer from 0 to 4, halogen, —OH, —O—R$_a$—O—, —OR$_b$, —CO—R$_c$, O—CO—R$_c$, —CO—OR$_c$, —O—CO—OR$_c$, —O—CO—O—CO—R$_c$, —O—OR$_c$, =O, =S, SO$_2$—R$_c$, —SO—R$_c$, —NR$_d$R$_e$, —CO—NR$_d$R$_e$, —O—CO—NR$_d$R$_e$, —NR—CO—NR$_d$R$_e$, —NR$_c$—CO—R$_e$, NR$_c$—CO—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, NR$_c$—CS—R$_d$, —SH, —S—R$_b$, and —PO$_2$—OR$_c$, where R$_a$ is selected from the group consisting of alkyl, heteroalkyl, alkenyl, aryl, heteroaryl, and alkynyl, R$_b$ is selected from the group consisting of alkyl, heteroalkyl, haloalkyl, alkenyl, alkynyl, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$ are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —CN, —(CH$_2$)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above;

R$_7$ is hydrogen or a C$_1$–C$_3$ alkyl, hydroxy or C$_1$–C$_3$ alkoxy group; and R$_8$ is hydrogen or an alkyl, alkenyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO$_2$, —N—OH, N—OR$_c$, —CN, —(CH$_2$)$_z$—CN where z is an integer from 0 to 4, halogen, —OH, —O—R$_a$—O—, —OR$_b$, —CO—R$_c$, O—CO—R$_c$, —CO—OR$_c$, —O—CO—OR$_c$, —O—CO—O—CO—R$_c$, —O—OR$_c$, =O, =S, SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, NR$_c$—CO—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, CO—SO$_2$—R$_c$, —CS—R$_c$, —CSO—R$_c$, —CSO$_2$—R$_c$, —NR$_c$—

CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where alkyl, heteroalkyl, alkenyl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$ and $R_e$ are defined above;

or a pharmaceutically acceptable salt thereof.

22. A compound represented by the formula I:

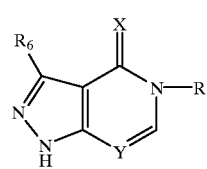

(I)

wherein:
X is O;
Y is N;
$R_6$ is H;
R is

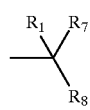

wherein:
$R_1$ is an alkyl, alkenyl, alkynyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, —CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, CO—$SO_2$—$R_c$, —CS—$R_c$, —CSO—$R_c$, —$CSO_2$—$R_c$, —$NR_c$CS—$R_d$, —O—CS—$R_c$, —O—CSO—$R_c$, O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, $NR_c$—CS—$R_d$, —SH, —S—$R_b$, and —$PO_2$—$OR_c$, where $R_a$ is selected from the group consisting of alkyl, heteroalkyl, alkenyl, aryl, heteroaryl, and alkynyl, $R_b$ is selected from the group consisting of alkyl, heteroalkyl, haloalkyl, alkenyl, alkynyl, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —CN, —$(CH_2)_z$—CN where z is an integer from 0 to 4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above;

$R_7$ is hydrogen or a $C_1$–$C_3$ alkyl, hydroxy or $C_1$–$C_3$ alkoxy group; and $R_8$ is an alkenyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —N—OH, N—$OR_c$, —CN, —$(CH_2)_z$—CN where z is an integer from 0 to 4, halogen, —OH, —O—$R_a$—O—, —$OR_b$, —CO—$R_c$, O—CO—$R_c$, CO—$OR_c$, —O—CO—$OR_c$, —O—CO—O—CO—$R_c$, —O—$OR_c$, =O, =S, $SO_2$—$R_c$, —SO—$R_c$, —$NR_dR_e$, —CO—$NR_dR_e$, —O—CO—$NR_dR_e$, $NR_c$—CO—$NR_dR_e$, —$NR_c$—CO—$R_e$, $NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—SR$_c$, —CO—SO—R$_c$, CO—SO$_2$—R$_c$, —CS—R$_c$, —CSO—R$_c$, —CSO$_2$—R$_c$, —NR$_c$CS—R$_d$, —O—CS—R$_c$, —O—CSO—R$_c$, O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, NR$_c$—CS—R$_d$, —SH, —S—R$_b$, and —PO$_2$—OR$_c$, where alkyl, heteroalkyl, alkenyl, and alkynyl, R$_b$ is selected from the group consisting of alkyl, heteroalkyl, haloalkyl, alkenyl, alkynyl, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$ are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —CN, —(CH$_2$)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above;

or a pharmaceutically acceptable salt thereof.

23. A compound represented by the formula I:

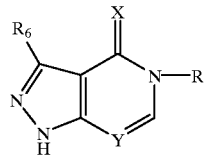

(I)

wherein:
X is O or S;
Y is N or CH;
R$_6$ is H or OH; and
R is

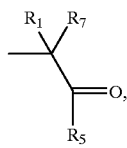

wherein:
R$_1$ is hydrogen or an alkyl, alkenyl, alkynyl, alkoxy, allyloxy, aryl, heteroaryl, cycloalkyl or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO$_2$, —N—OH, N—OR$_c$, —CN, —(CH$_2$)$_z$—CN where z is an integer from 0 to 4, halogen, —OH, —O—R$_a$—O—, —OR$_b$, —CO—R$_c$, O—CO—R$_c$, —CO—OR$_c$, —O—CO—OR$_c$, —O—CO—O—CO—R$_c$, —O—OR$_c$, =O, =S, SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, NR$_c$—CO—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, CO—SO$_2$—R$_c$, —CS—R$_c$, —CSO—R$_c$, —CSO$_2$—R$_c$, —NR$_c$—CS—R$_d$, —O—CS—R$_c$, —O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, NR$_c$—CS—R$_d$, —SH, —S—R$_b$, and —PO$_2$—OR$_c$, where R$_a$ is selected from the group consisting of alkyl, heteroalkyl, alkenyl, aryl, heteroaryl, and alkynyl, R$_b$ is selected from the group consisting of alkyl, heteroalkyl, haloalkyl, alkenyl, alkynyl, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$ are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —CN, —(CH$_2$)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above;

R$_5$ is hydrogen or an alkyl, alkenyl, alkynyl, cycloalkyl, heterocycloalkyl, aryl or heteroaryl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO$_2$, —N—OH, N—OR$_c$, —CN, —(CH$_2$)$_z$—CN where z is an integer from 0 to 4, halogen, —OH, —O—R$_a$—O—, —OR$_b$, —CO—R$_c$, O—CO—R$_c$, —CO—OR$_c$, —O—CO—OR$_c$, —O—CO—O—CO—R$_c$, —O—OR$_c$, =O, =S, SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, NR$_c$—CO—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, CO—SO$_2$—R$_d$, —CS—R$_c$, —CSO—R$_c$, —CSO$_2$—R$_c$, —NR$_c$—CS—R$_d$, —O—CS—R$_c$, —O—CSO—R$_c$, O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, NR$_c$—CS—R$_d$, —SH, —S—R$_b$, and —PO$_2$—OR$_c$, where R$_a$ is selected from the group consisting of alkyl, heteroalkyl, alkenyl, aryl, heteroaryl, and alkynyl, R$_b$ is selected from the group consisting of alkyl, heteroalkyl, haloalkyl, alkenyl, alkynyl, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$ are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —CN, —(CH$_2$)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$ and R$_e$ are defined above; and R$_7$ is hydrogen or a C$_1$–C$_3$ alkyl, hydroxy or C$_1$–C$_3$ alkoxy group;

or a pharmaceutically acceptable salt thereof.

24. A compound or pharmaceutically acceptable salt according to claim 23, wherein R$_5$ is a cycloalkyl, heterocycloalkyl, aryl or heteroaryl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —NO$_2$, —N—OH, N—OR$_c$, —CN, —(CH$_2$)$_z$—CN where z is an integer from 0 to 4, halogen, —OH, —O—R$_a$—O—, —OR$_b$, —CO—R$_c$, O—CO—R$_c$, —CO—OR$_c$, —O—CO—OR$_c$, —O—CO—O—CO—R$_c$, —O—OR$_c$, =O, =S, SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_c$, NR$_c$—CO—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, NR$_c$—CS—R$_d$, —SH, —S—R$_b$, and —PO$_2$—OR$_c$, where R$_a$ is selected from the group consisting of alkyl, heteroalkyl, alkenyl, aryl, heteroaryl, and alkynyl, R$_b$ is selected from the group consisting of alkyl, heteroalkyl, haloalkyl, alkenyl, alkynyl, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$, and R$_e$ are each independently selected from the group consisting of hydrogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —CN, —(CH$_2$)$_z$—CN where z is an integer from 0 to 4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above.

25. A compound or pharmaceutically acceptable salt according to claim 1, wherein Y is N; X is O; and R$_6$ is H.

26. A compound or pharmaceutically acceptable salt according to claim 1, wherein Y is N; X is S; and R$_6$ is H.

27. A compound or pharmaceutically acceptable salt according to claim 1, wherein Y is CH; X is O; and R$_6$ is H.

28. A compound or pharmaceutically acceptable salt according to claim 1, wherein Y is CH; X is S; and R$_6$ is H.

29. A compound or pharmaceutically acceptable salt according to claim 1, wherein Y is N; X is O; and R$_6$ is OH.

30. A compound or pharmaceutically acceptable salt according to claim 1, wherein Y is N; X is S; and R$_6$ is OH.

31. A compound or pharmaceutically acceptable salt according to claim 1, wherein Y is CH; X is O; and R$_6$ is OH.

32. A compound or pharmaceutically acceptable salt according to claim 1, wherein Y is CH; X is S; and R$_6$ is OH.

33. A compound selected from the group consisting of

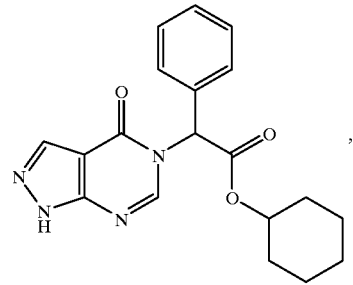

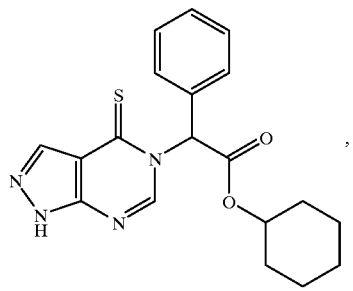
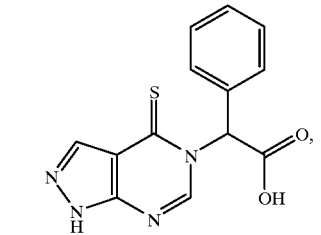
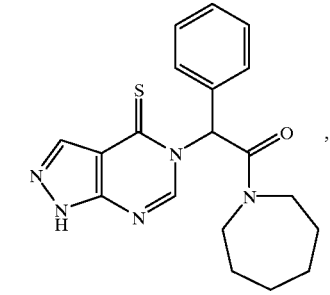
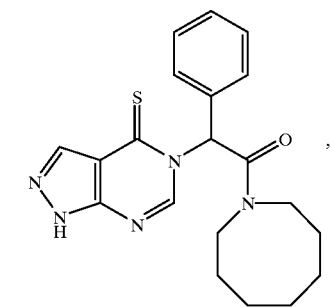
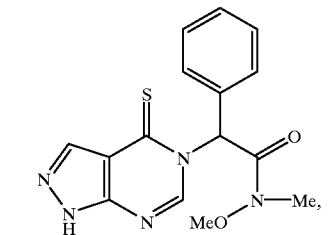
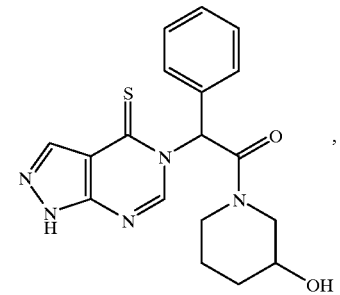
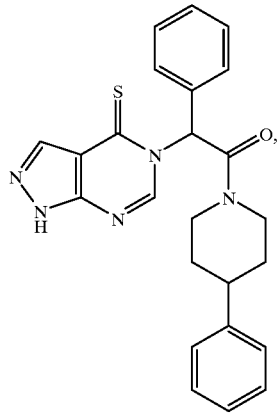
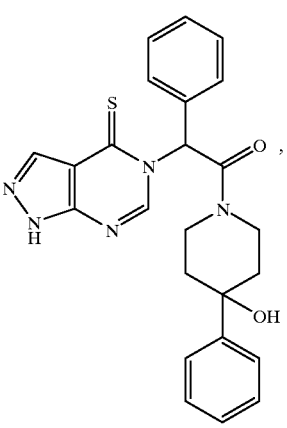
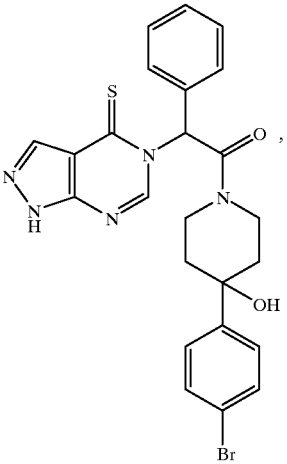

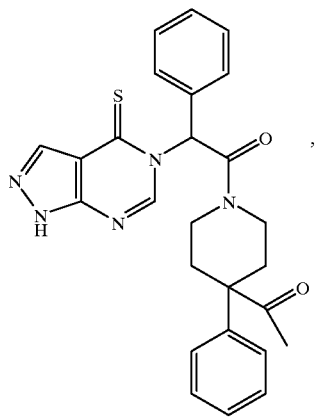
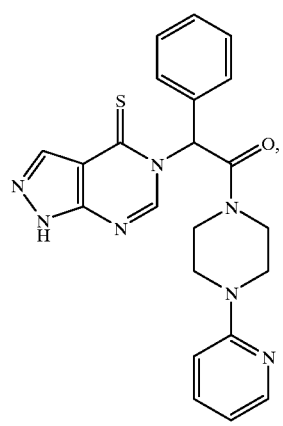
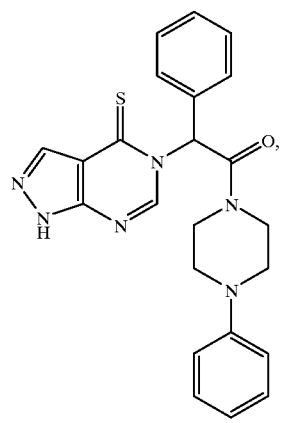
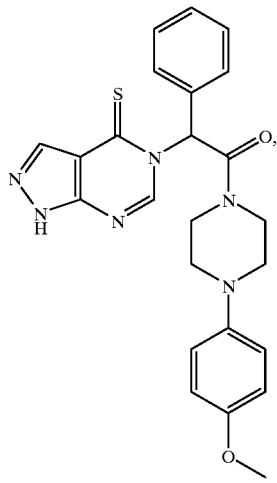
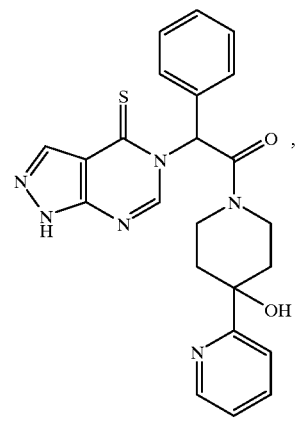
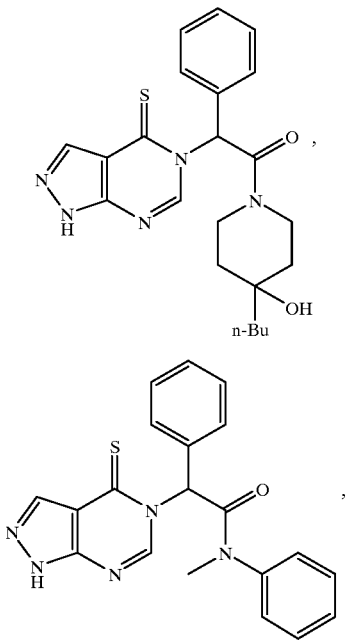

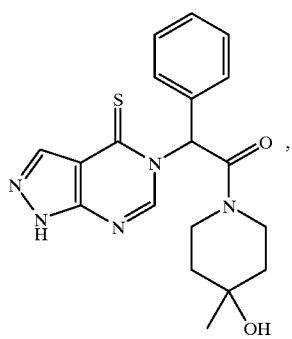
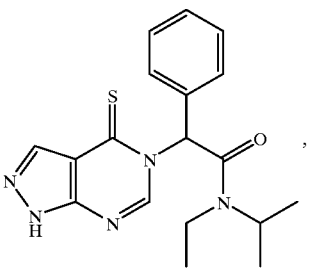
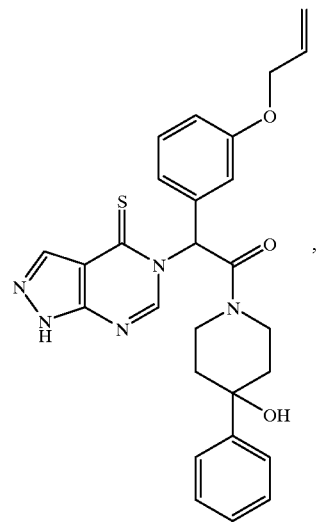
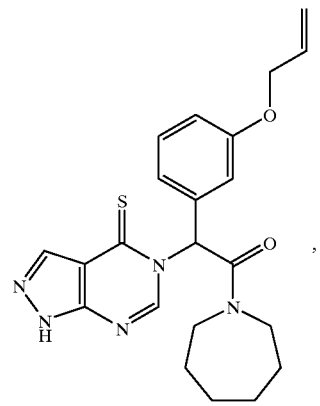
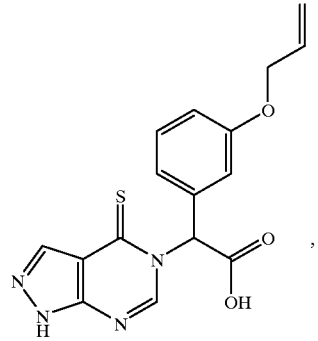
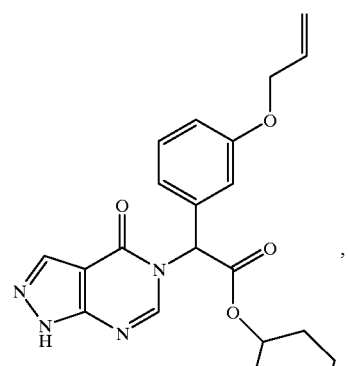
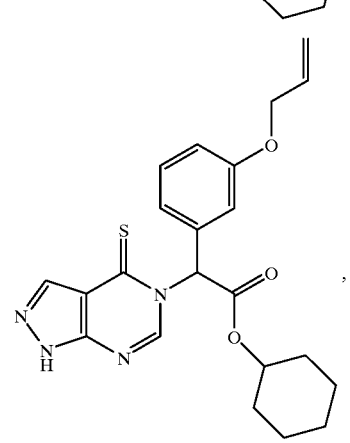
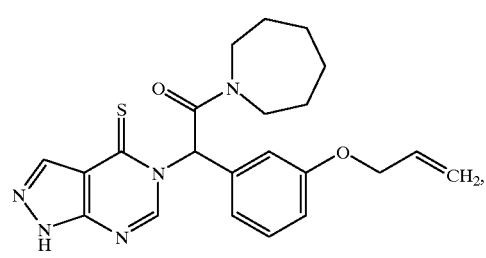
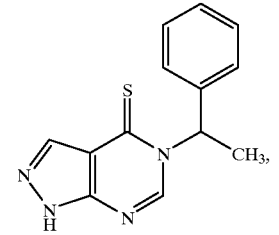

-continued
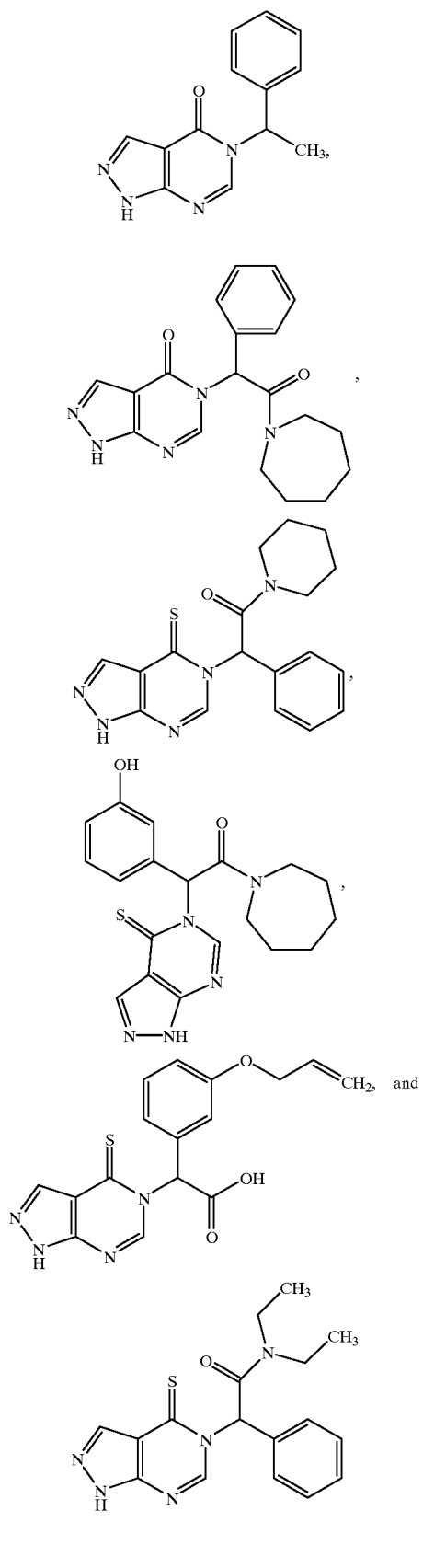
and pharmaceutically acceptable salts thereof.
34. A compound selected from the group consisting of
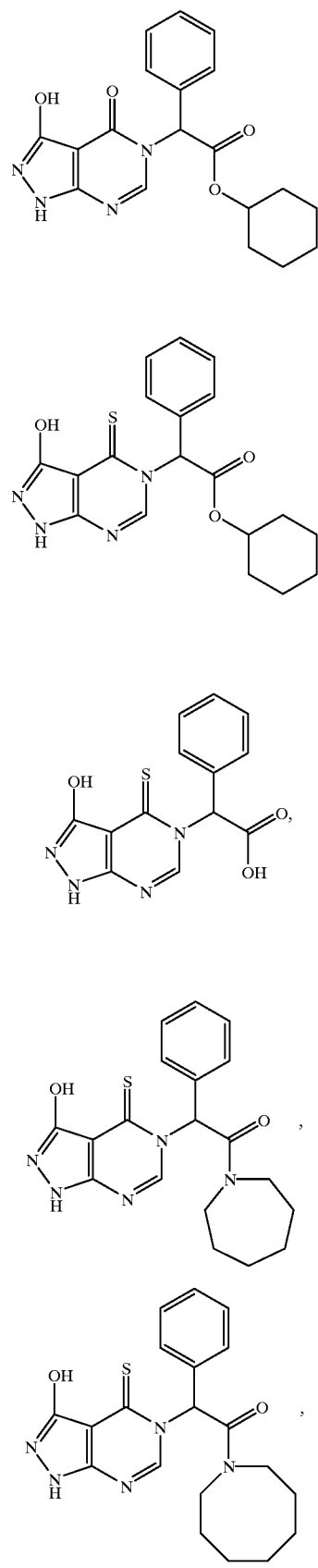

169
-continued
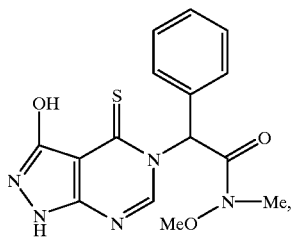
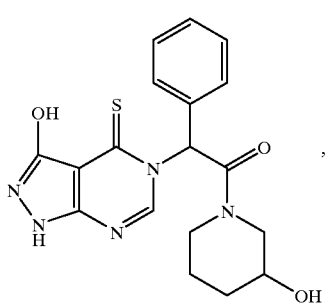
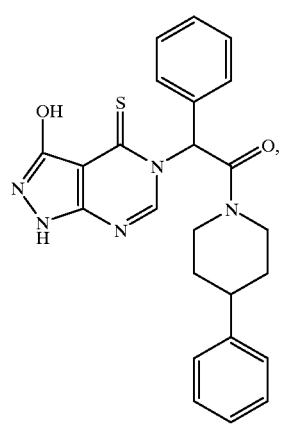
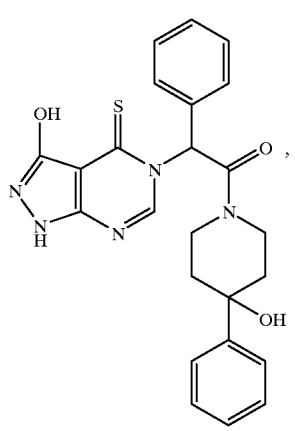
170
-continued
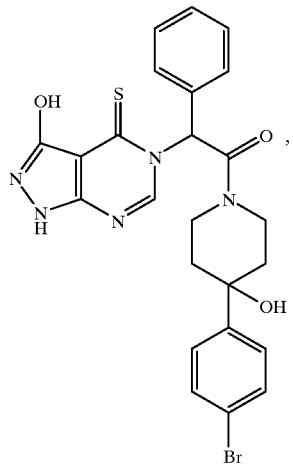
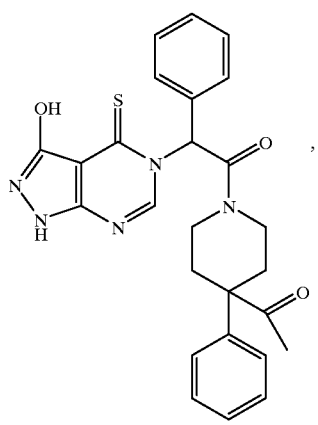
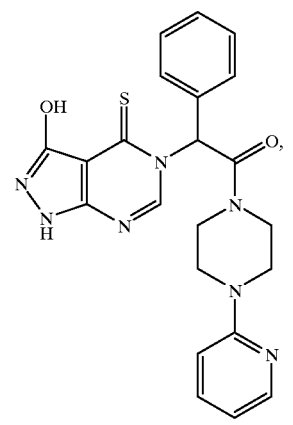

-continued
171
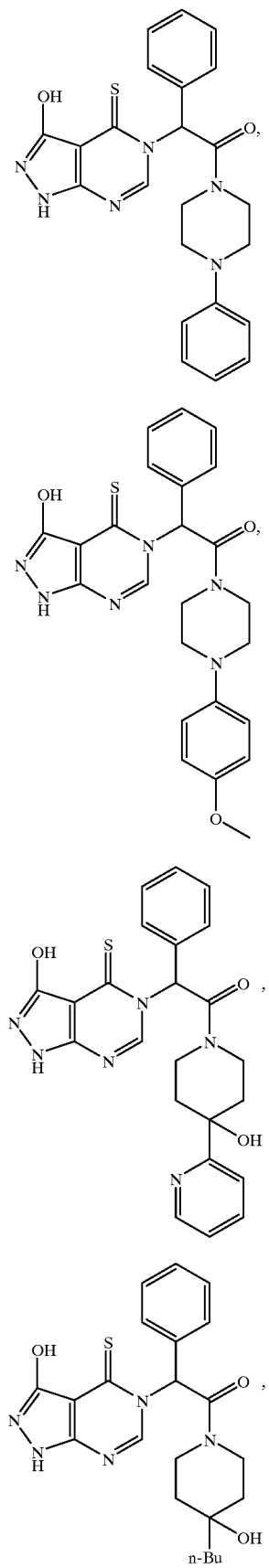
172
-continued
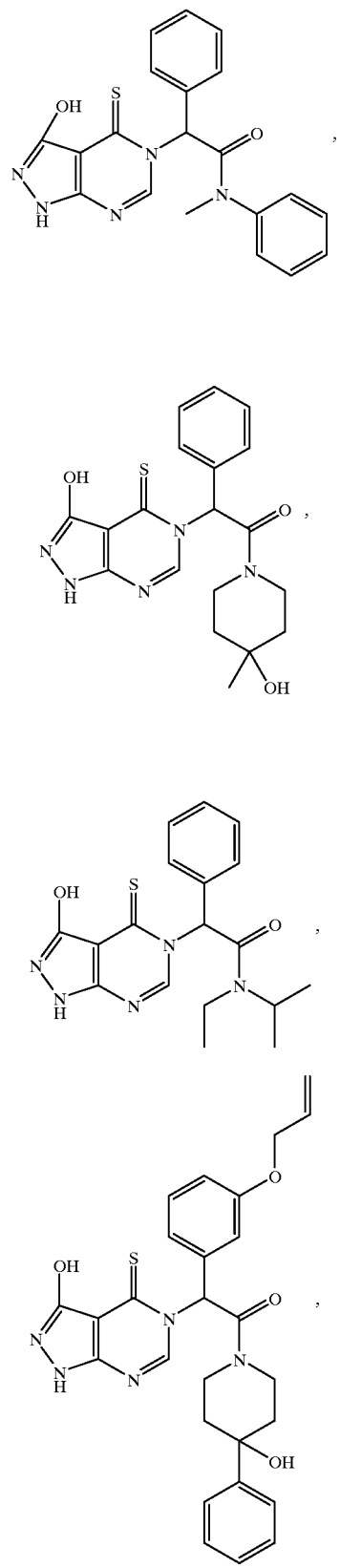

173
-continued
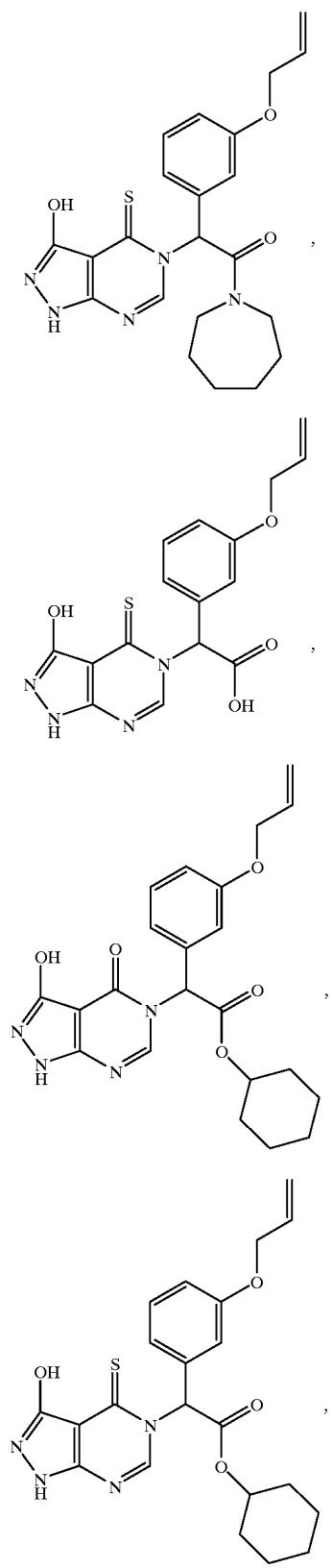
174
-continued
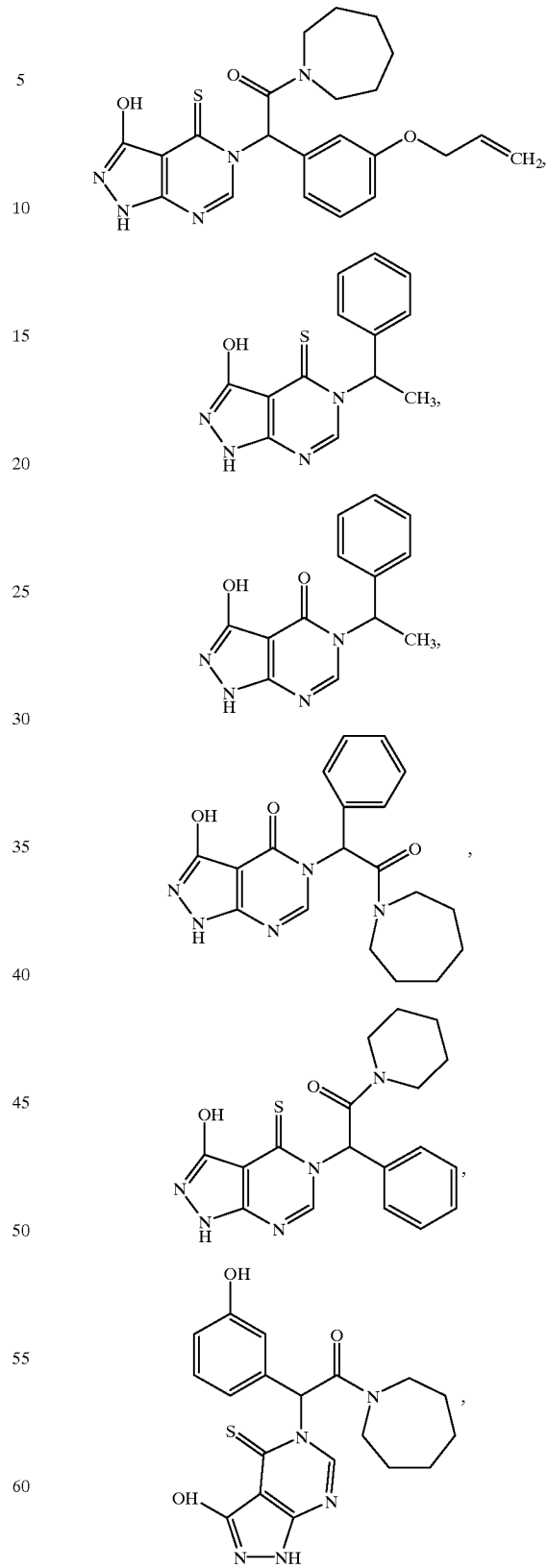

-continued
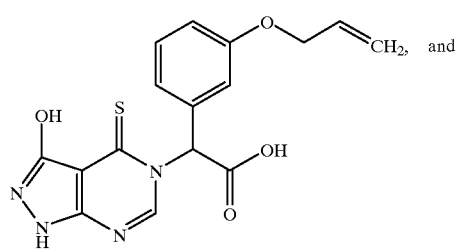
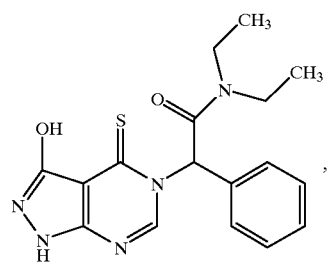
and pharmaceutically acceptable salts thereof.
35. A compound selected from the group consisting of
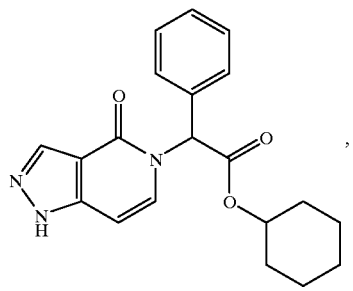
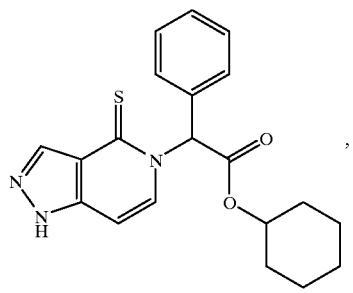
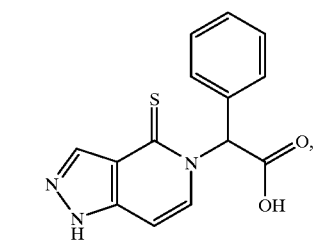
-continued
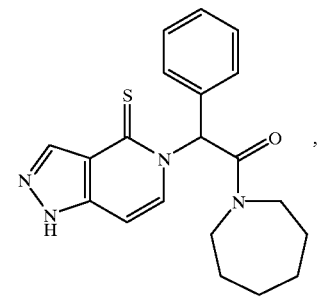
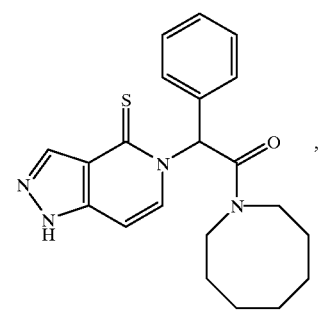
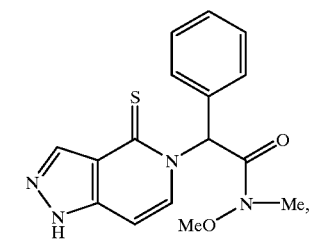
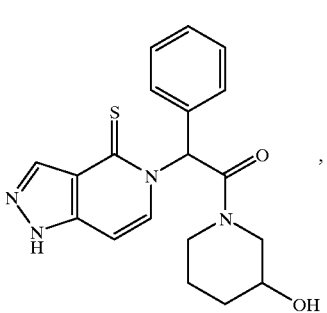
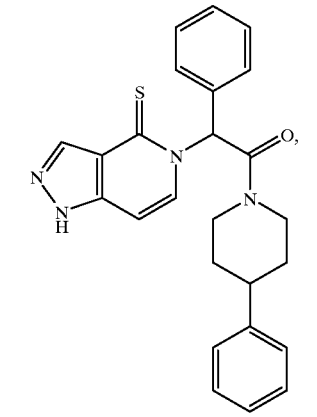

177
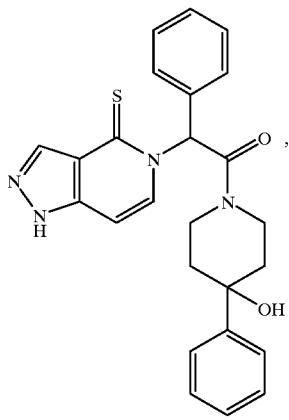
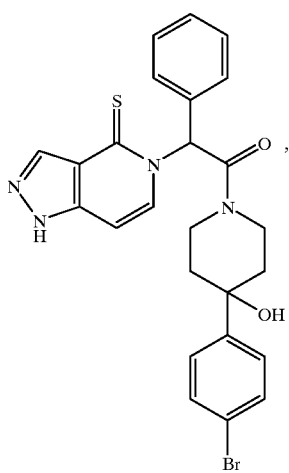
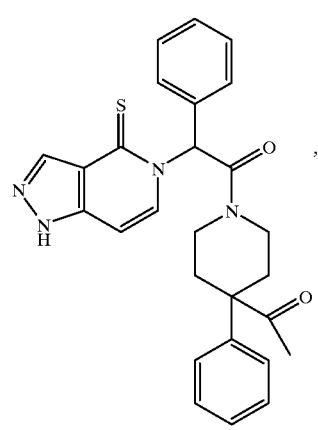
178
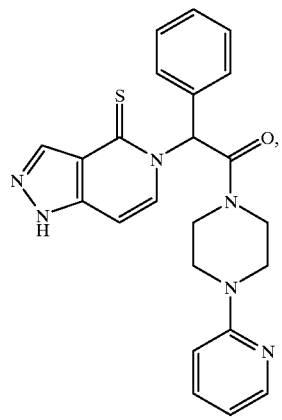
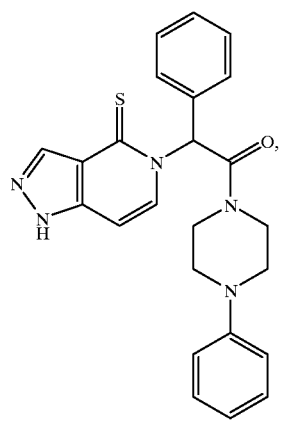
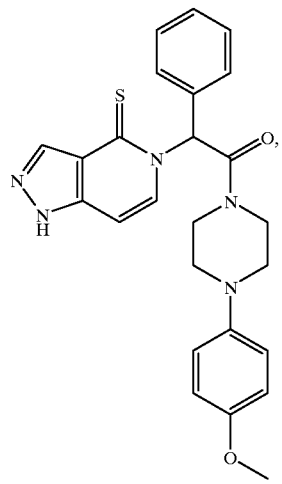

-continued
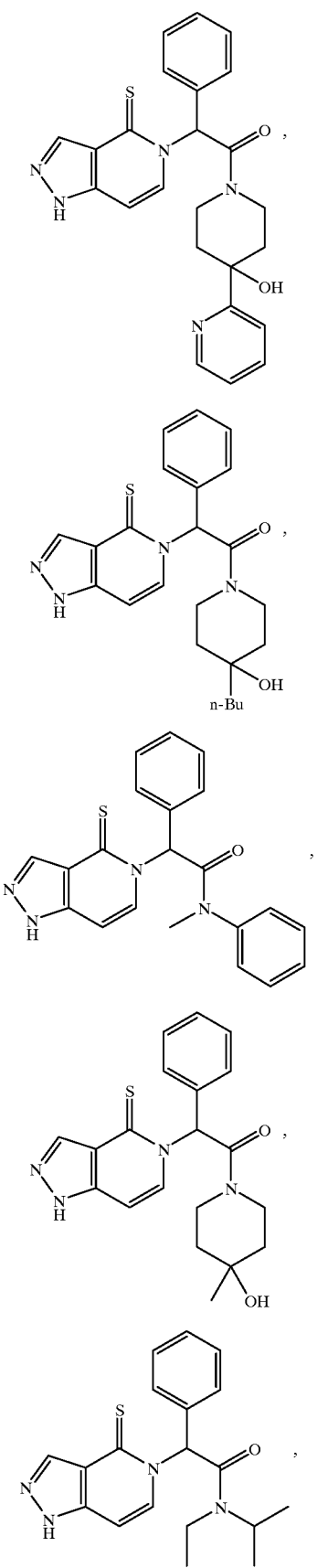
-continued
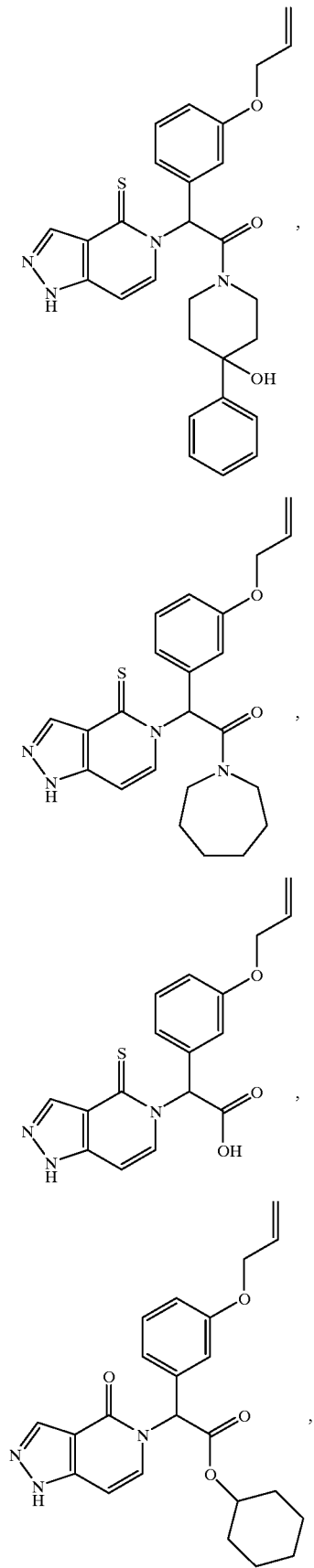

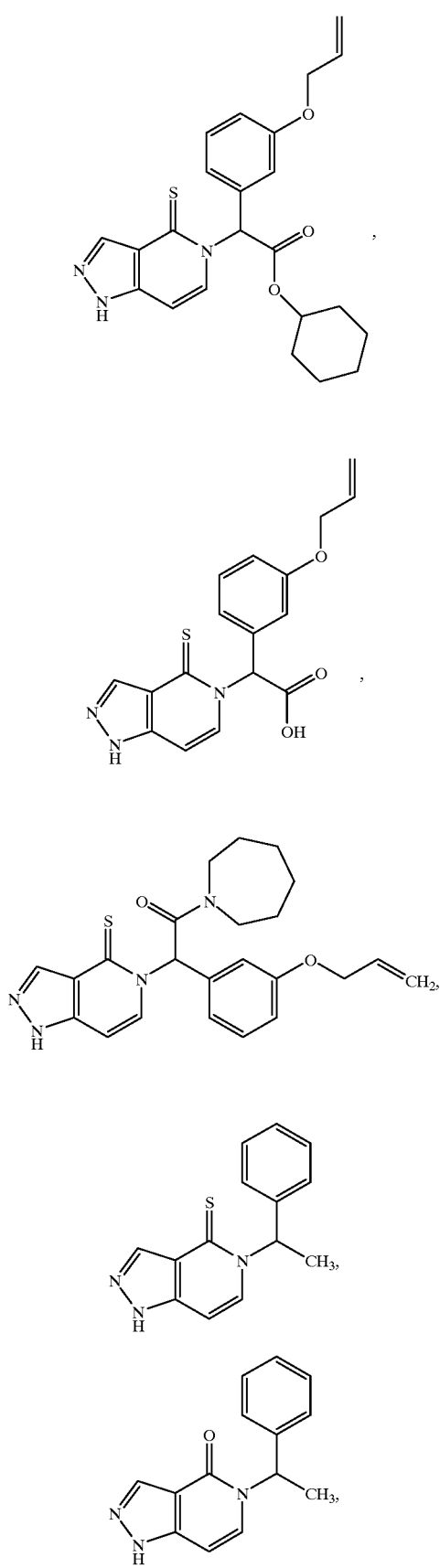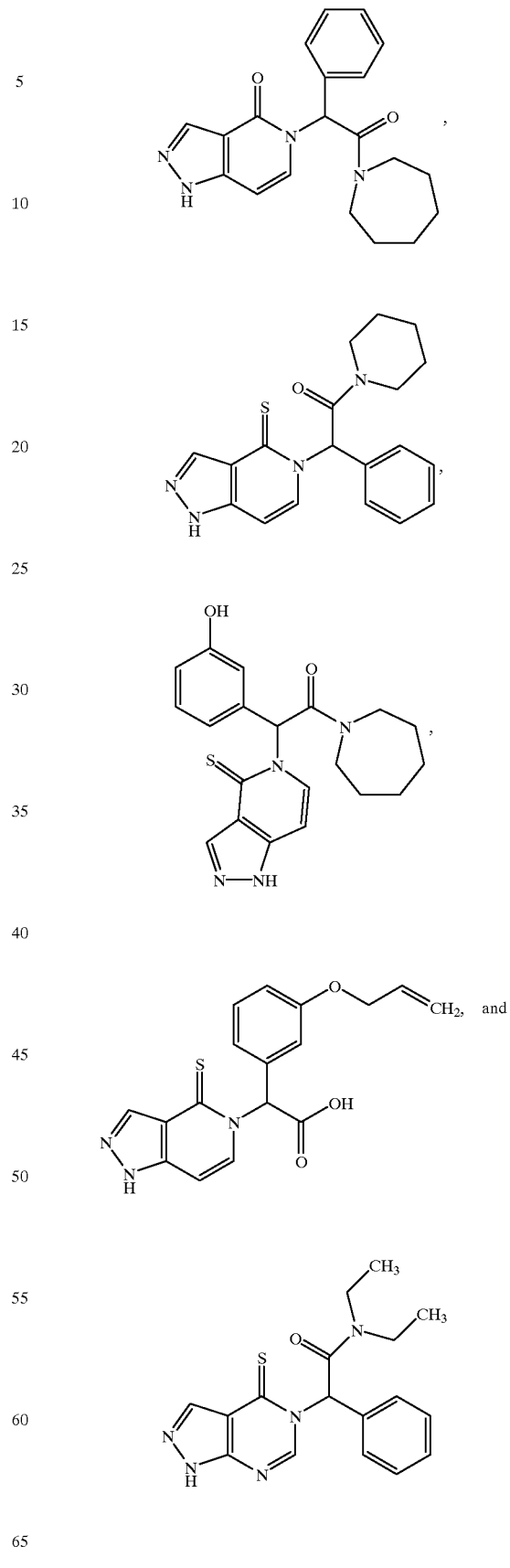
and pharmaceutically acceptable salts thereof.

36. A compound selected from the group consisting of
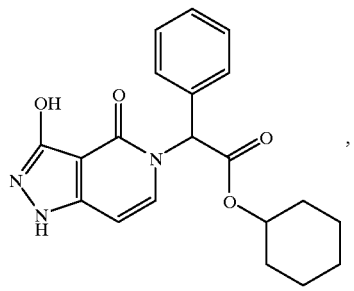,
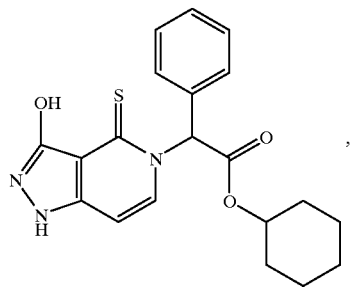,
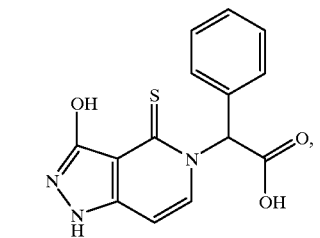,
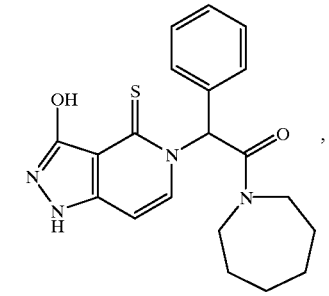,
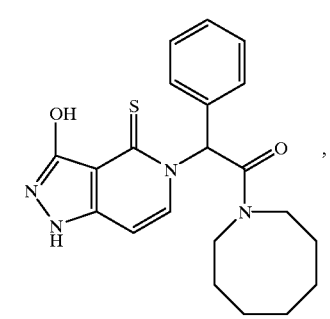,
-continued
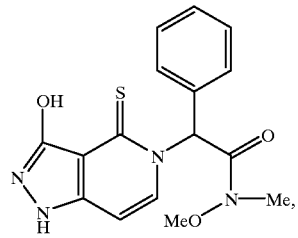,
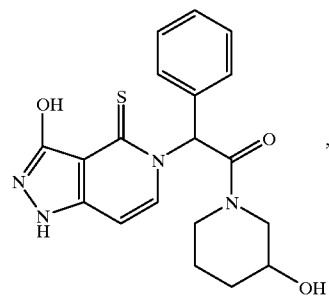,
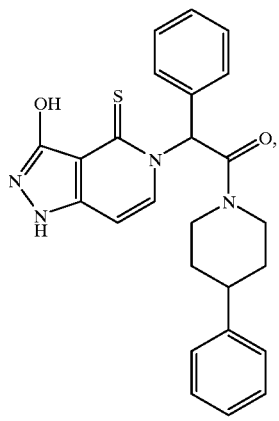,
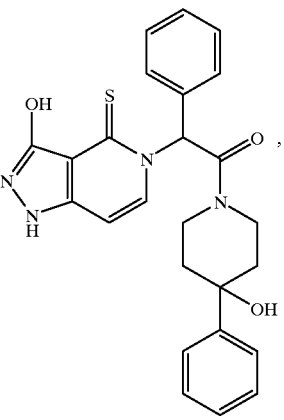,

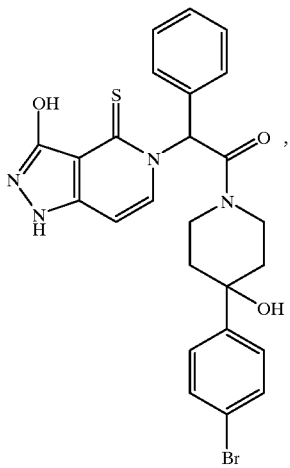
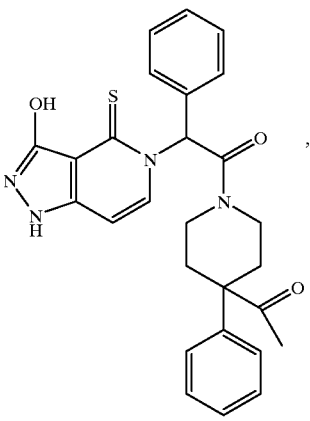
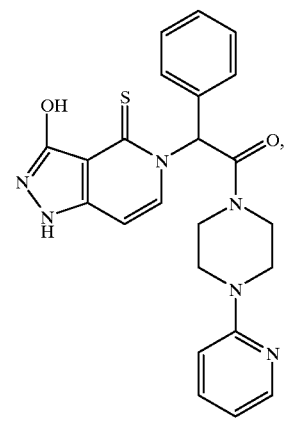
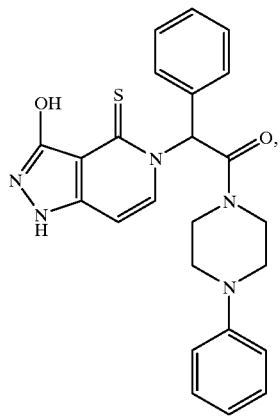
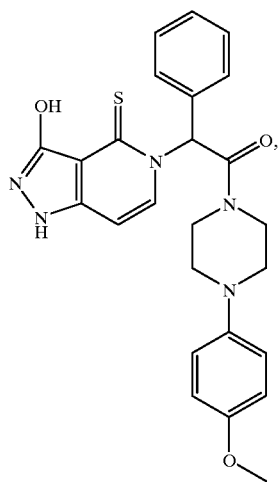
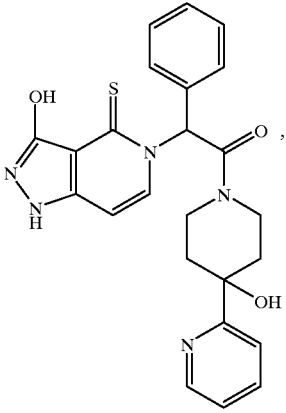
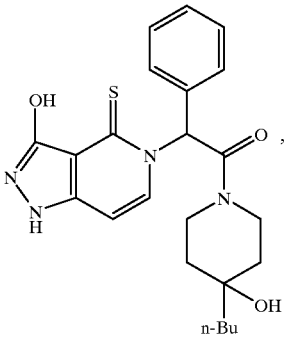

187
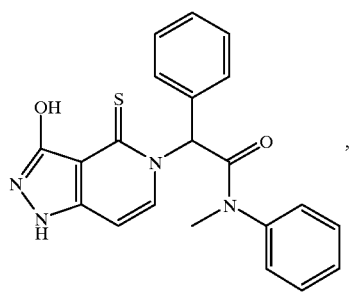
,
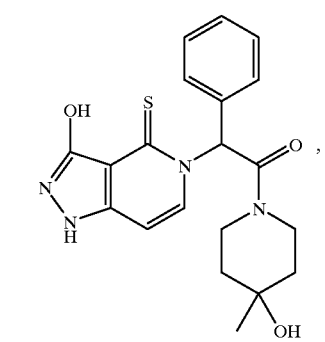
,
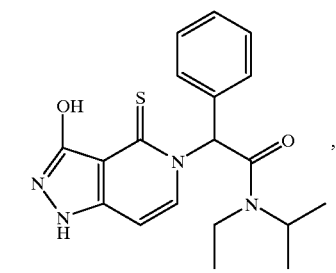
,
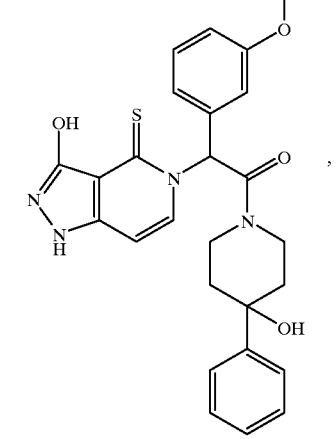
,
188
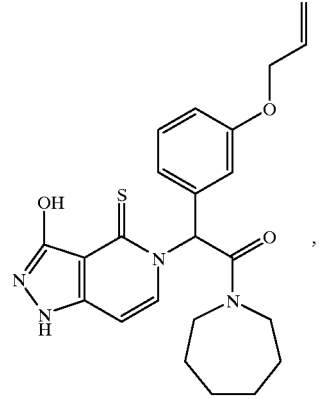
,
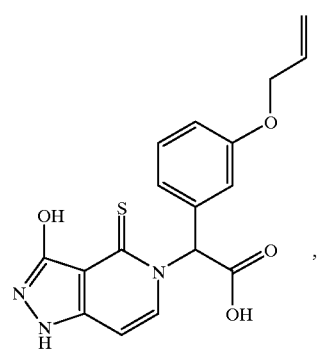
,
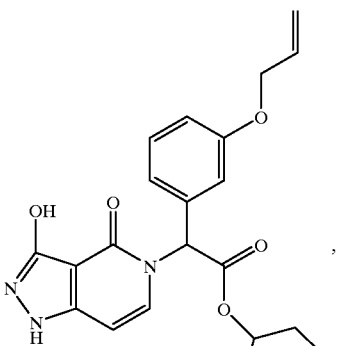
,
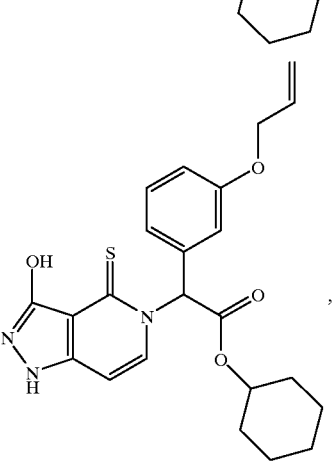
, -continued

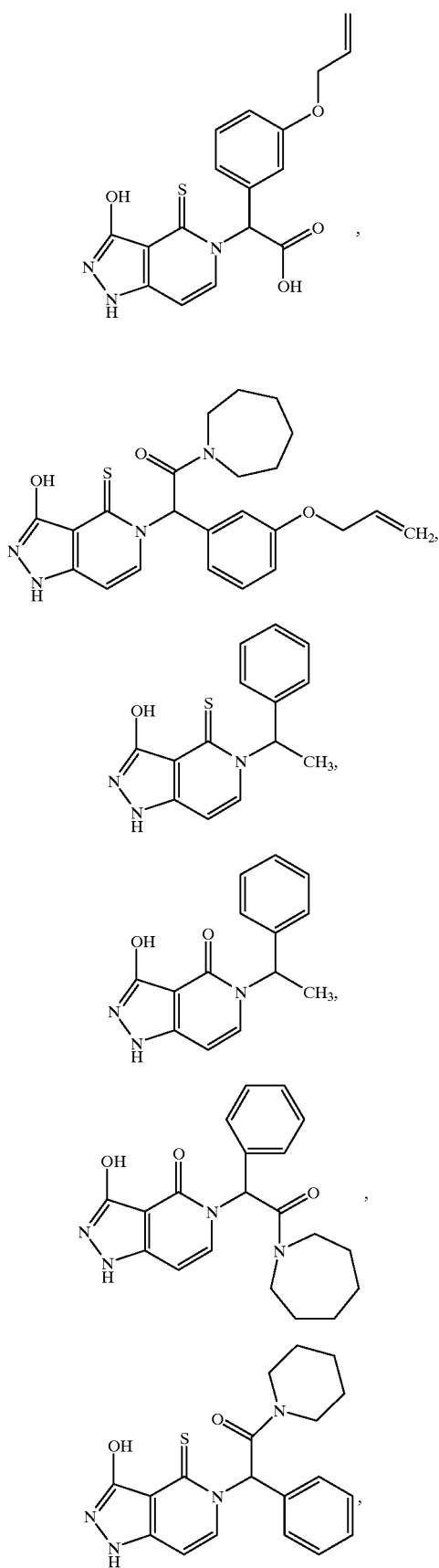

-continued

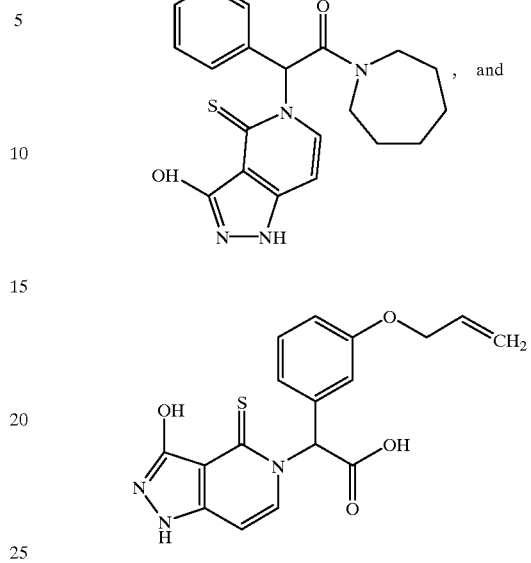

and pharmaceutically acceptable salts thereof.

37. A compound or pharmaceutically acceptable salt as defined in claim 1, wherein the compound or pharmaceutically acceptable salt has an $IC_{50}$ against ERAB activity of less than or equal to 600 μM.

38. A compound or pharmaceutically acceptable salt as defined in claim 37, wherein the compound or pharmaceutically acceptable salt has an $IC_{50}$ against ERAB activity of less than or equal to 50 μM.

39. A compound or pharmaceutically acceptable salt as defined in claim 37, wherein the compound or pharmaceutically acceptable salt has an $IC_{50}$ against ERAB activity of less than or equal to 3.0 μM.

40. A composition comprising:
   a therapeutically effective amount of a compound or pharmaceutically acceptable salt according to claim 1; and
   a pharmaceutically acceptable carrier, diluent, or vehicle therefore.

41. A composition comprising:
   a therapeutically effective amount of a compound or pharmaceutically acceptable salt according to claim 33; and
   a pharmaceutically acceptable carrier, diluent, or vehicle therefore.

42. A composition comprising:
   a therapeutically effective amount of a compound or pharmaceutically acceptable salt according to claim 34; and
   a pharmaceutically acceptable carrier, diluent, or vehicle therefore.

43. A composition comprising:
   a therapeutically effective amount of a compound or pharmaceutically acceptable salt according to claim 35; and
   a pharmaceutically acceptable carrier, diluent, or vehicle therefore.

44. A composition comprising:
   a therapeutically effective amount of a compound or pharmaceutically acceptable salt according to claim 36; and a pharmaceutically acceptable carrier, diluent, or vehicle therefore.

45. A method of inhibiting or modulating an enzyme activity of ERAB or HADH2, comprising contacting said enzyme with an effective amount of a compound or pharmaceutically acceptable salt defined in claim 1.

46. A method of inhibiting or modulating an enzyme activity of ERAB or HADH2, comprising contacting said enzyme with an effective amount of a compound or pharmaceutically acceptable salt defined in claim 33.

47. A method of inhibiting or modulating an enzyme activity of ERAB or HADH2, comprising contacting said enzyme with an effective amount of a compound or pharmaceutically acceptable salt defined in claim 34.

48. A method of inhibiting or modulating an enzyme activity of ERAB or HADH2, comprising contacting said enzyme with an effective amount of a compound or pharmaceutically acceptable salt defined in claim 35.

49. A method of inhibiting or modulating an enzyme activity of ERAB or HADH2, comprising contacting said enzyme with an effective amount of a compound or pharmaceutically acceptable salt defined in claim 36.

* * * * *